(12) United States Patent
Ben Khaled et al.

(10) Patent No.: US 12,037,593 B2
(45) Date of Patent: Jul. 16, 2024

(54) METHODS AND MEANS FOR MODIFYING THE ALKALOID CONTENT OF PLANTS

(71) Applicant: BRITISH AMERICAN TOBACCO (INVESTMENTS) LIMITED, London (GB)

(72) Inventors: Sara Ben Khaled, London (GB); Francisco Anastacio De Abreu E Lima, London (GB)

(73) Assignee: BRITISH AMERICAN TOBACCO (INVESTMENTS) LIMITED, London (GB)

( * ) Notice: Subject to any disclaimer, the term of this patent is extended or adjusted under 35 U.S.C. 154(b) by 262 days.

(21) Appl. No.: 17/309,285

(22) PCT Filed: Nov. 14, 2019

(86) PCT No.: PCT/GB2019/053226
§ 371 (c)(1),
(2) Date: May 14, 2021

(87) PCT Pub. No.: WO2020/099875
PCT Pub. Date: May 22, 2020

(65) Prior Publication Data
US 2022/0033837 A1    Feb. 3, 2022

(30) Foreign Application Priority Data
Nov. 16, 2018    (GB) ...................................... 1818715

(51) Int. Cl.
*C12N 15/82*    (2006.01)
*C07K 14/415*    (2006.01)
*A24B 15/10*    (2006.01)

(52) U.S. Cl.
CPC ........ *C12N 15/8243* (2013.01); *C07K 14/415* (2013.01); *C12N 15/8218* (2013.01); *A24B 15/10* (2013.01)

(58) Field of Classification Search
None
See application file for complete search history.

(56) References Cited

U.S. PATENT DOCUMENTS 7,798,153 B2 *   9/2010   Lawrence, Jr. ........ A24B 15/10
                                                            131/352
9,066,538 B2 *   6/2015   Chen ........................ A24B 3/12
(Continued)

FOREIGN PATENT DOCUMENTS

KR   20040111243 A   12/2004
WO   2016124932 A1   8/2016
(Continued)

OTHER PUBLICATIONS

Moldoveanu et al. 2016 "Nicotine Analysis in Several Non-Tobacco Plant Materials" Contributions to Tobacco & Nicotine Research (formerly Beitrage zur Tabakforschung International) 27(2):54-59 (Year: 2016).*

(Continued)

*Primary Examiner* — Matthew R Keogh
*Assistant Examiner* — Rebecca Stephens
(74) *Attorney, Agent, or Firm* — McKee, Voorhees & Sease, PLC

(57) ABSTRACT

The present invention provides a method for modulating (e.g. decreasing) the alkaloid content of a plant (e.g. a tobacco plant), the method comprising modifying said plant by modulating (e.g. decreasing) the expression of at least one armadillo repeat protein. The present invention also provides for the use of an armadillo repeat protein for modulating the alkaloid content of a plant, as well as tobacco (Continued)

cells, plants, plant propagation materials, harvested leaves, processed tobaccos, or tobacco products obtainable in accordance with the invention.

17 Claims, 7 Drawing Sheets

Specification includes a Sequence Listing.

(56) References Cited

U.S. PATENT DOCUMENTS

| | | |
|---|---|---|
| 2009/0241215 A1 | 9/2009 | Douchkov et al. |
| 2019/0203218 A1 | 7/2019 | Drake Stowe et al. |
| 2020/0131524 A1 | 4/2020 | Miller et al. |

FOREIGN PATENT DOCUMENTS

| | | |
|---|---|---|
| WO | 2017122015 A1 | 7/2017 |
| WO | 2018067985 A1 | 4/2018 |

OTHER PUBLICATIONS

UniProtKB Accession No. A0A1S4BNQ5 version 6 dated Feb. 28, 2018 entitled "U-box domain-containing protein 7-like" (Year: 2018).*

UniProtKB Accession No. A0A1S4BNQ5 Version 6 dated Feb. 28, 2018 (1 total page). (Year: 2018).*

Database Uniprot, "U-box domain-containing protein 7-like", EBI accession No. XP_016490526.1, 6 pages, Apr. 12, 2017.

International Searching Authority in connection with PCT/GB2019/053226 filed Nov. 14, 2019, "Written Opinion of the International Searching Authority", 5 pages, mailed May 22, 2020.

Amador et al., "Gibberellins Signal Nuclear Import of PHOR1, a Photoperiod-Responsive Protein with Homology to *Drosophila armadillo*", Cell, vol. 106, pp. 343-354, Aug. 10, 2001.

Coates, Juliet C., "Armadillo Repeat Proteins: Versatile Regulators of Plant Development and Signalling", Plant Cell Monographs, pp. 299-314, 2007.

Coates, Juliet C., "Armadillo repeat proteins: beyond the animal kingdom", Trends in Cell Biology, vol. 13, No. 9, pp. 463-471, Sep. 9, 2003.

Gális et al., "A novel R2R3 MYB transcription factor NIMYBJS1 is a methyl jasmonate-dependent regulator of phenylpropanoid-conjugate biosynthesis in tobacco", The Plant Journal, vol. 46, pp. 573-592, 2006.

González-Lamothe et al., "The U-Box Protein CMPG1 is Required for Efficient Activation of Defense Mechanisms Triggered by Multiple Resistance Genes in Tobacco and Tomato", The Plant Cell, vol. 18, pp. 1067-1083, Apr. 2006.

Huber et al., "Three-Dimensional Structure of the Armadillo Repeat Region of β-Catenin", Cell, vol. 90, pp. 871-882, Sep. 5, 1997.

Kim et al., "CHRK1, a chitinase-related receptor-like kinase, interacts with NtPUB4, an armadillo repeat protein, in tobacco", Biochimica et Biophysica Acta, vol. 1651, pp. 50-59, 2003.

Mandal et al., "Identification, characterization, expression profiling, and virus-induced gene silencing of armadillo repeat-containing proteins in tomato suggest their involvement in tomato leaf curl New Delhi virus resistance", Functional & Integrative Genomics, vol. 18, pp. 101-111, 2018.

Rushton et al., "Tobacco Transcription Factors: Novel Insights into Transcriptional Regulation in the Solanaceae1[C] [W][OA]", Plant Physiology, vol. 147, pp. 280-295, May 2008.

Saitoh et al., "The Alkaloid Contents of Sixty *Nicotiana* Species", Phytochemistry, vol. 24, No. 3, pp. 477-480, 1985.

Voelckel et al., "Anti-sense expression of putrescine N-methyltransferase confirms defensive role of nicotine in Nicotiana sylvestris against Manduca sexta", Chemoecology, vol. 11, pp. 121-126, 2001.

Yang et al., "The E3 Ubiquitin Ligase Activity of *Arabidopsis* Plant U-BOX17 and Its Functional Tobacco Homolog ACRE276 Are Required for Cell Death and Defense", The Plant Cell, vol. 18, pp. 1084-1098, Apr. 2006.

Bergler et al., "Plant U-box armadillo repeat proteins AtPUB18 and AtPUB19 are involved in salt inhibition of germination in *Arabidopsis*," Plant Biology, 2011, vol. 13, pp. 725-730.

NCBI Reference Sequence, "Predicted: U-box domain-containing protein 7 [Nicotiana sylvestris]," Genbank, Oct. 21, 2014, XP_009778314, 2 pages.

NCBI Reference Sequence, "Predicted: Nicotiana tabacum U-box domain-containing protein 7-like (LOC107810281), mRNA," Genbank, May 3, 2016, XM_016635040, 2 pages.

Wang et al., "Construction and expression of rat Armcx3 gene eukaryotic expression vector," Clinical Journal of Cellular and Molecular Immunology, 2015, vol. 31, No. 6, 4 pages.

* cited by examiner

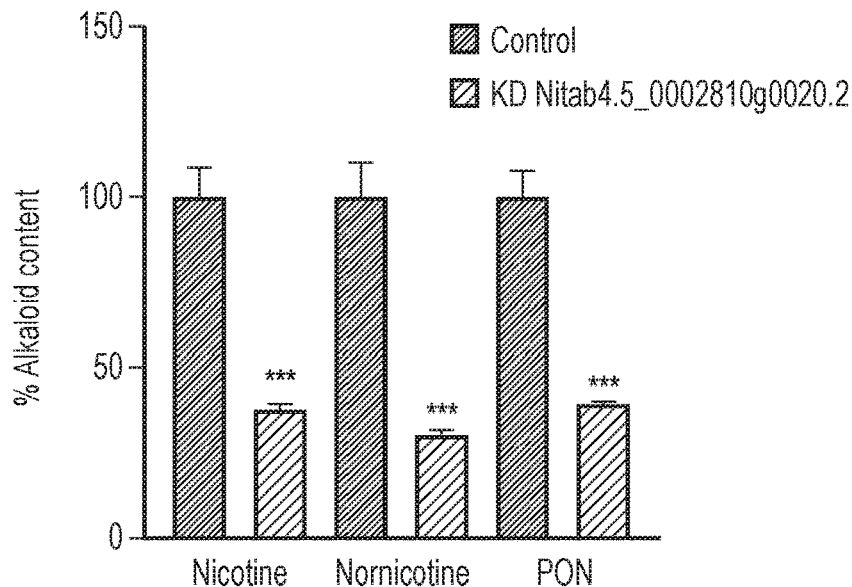

FIG. 7

Nitab4.5_0002810g0020.2 Protein:

SEQ ID NO: 1

MPNTSTTSNWYLTYIKLRFFTKVRRFLQLKAASKKPLKPSDQPREKSDTLIVIEEGEKGEKGIMGKESDIKDNGWMV
LQKSVKKLHFGSSEEKEVAAKEIKKLAKEDLKRRKLMAELGVIPPLVAMIGGSEVVLRRQRLAVQALVELANGSFTN
KALMVEAGILSRLPQKPDNLDGNTRQEFAELILSISSLANTQFSMDSSRIIPFVVSILDSSNSSVETKSTCLGTLYNLSSV
LENAAILATNGTMTTLFRLSSLKEVSEKALATLGNLVVTLMGKKAMEENPMVPESLIEIMTWEEKPKCQELSVYILM
ILAHQSSIQREKMAKAGIVPVLLEVALLSSPLAQKRALKLLQWFKDERQSKMGPHSGPQAGRIAIDSPPVSPRAVDE
SKKLMKKIVKQSLHKNMETITSRANGGSDCSRLKSLVVSSSSKSLPY

FIG. 8

Nitab4.5_0002810g0020.2 Genomic sequence:

SEQ ID NO: 2

CCGATGTAACTGACATATCGTGAATCTGCATGTGCTTTCTGCTCTTCTTGTTTTGTTGCCCTCAAAGTCTTCTTCT
CTCTTTGTCTGCTTCTTTTCCAACTAATTCTTTCTTTCACCAAAAGTCAGATATAAACACACTTAATTTAAAACCT
TTTAGAATTTCAATTAAACCACCCCTACCCCTACCCCTACCCCCACCACGGCCCCTACAAAACCGTTCTTCTTCAT
ATATGTCCTCTTCACGAGTAGTATATATCGAAACATGCCTAATACTTCAACAACTAGTAATTGGTATTTGACCTA
CATAAAGCTTAGGTTTTTCACAAAAGTCCGTCGGTTCCTTCAGCTCAAGGCAGCATCTAAAAAGCCATTGAAAC
CGTCTGATCAGCCGAGAGAAAAATCAGATACTTTGATCGTGATTGAAGAAGGTGAAAAGGGAGAAAAGGGT
ATAATGGGAAAGAGAGTGATATTAAAGATAATGGATGGATGGTTTTGCAAAAATCTGTGAAGAAACTTCAC
TTTGGGAGTTCGGAAGAAAAGAGGTGGCAGCCAAAGAGATAAAAAGTTGGCTAAAGAAGACTTAAAGAG
GAGGAAACTGATGGCGGAGCTGGGCGTAATTCCGCCGCTTGTGGCCATGATTGGTGGTTCTGAGGTGGTGCT
GCGGCGGCAGAGATTGGCTGTTCAAGCATTAGTTGAGCTTGCCAATGGCTCTTTCACGTAAGTTCATTTACTTA
TAATTTTATAAATCATAAATATTAATCACTCGTTTAAGTAAAATCCTTTTTTATTTTATTTTATCAATTAATCCACT
TTCTTCTTCATGCTTGGTTTTCTCCTCGGCTAATAGTTACGATCAAGTTTAAGTGCTAAGTTTGACGCTGCACTA
ATATATGTGTTTATCGTAAAAACGATAAGAACAAGAATCATGAATTTATAACAATTTGTAATTTTATAATAATG
TGAGATTTTTTCATCACATTAAGTAAGAAATTTGTAAAGGTGAAGTTCAAATTTTATCCCATATTCGTGAACTG
GAGAACTGATTTTAAAATTTAATTAAATCGCATTATCCATTTTGGAAAAGCAAATGGCATGTTAATTTTCTGTTT
CGTGATTTCTTTCAGTAAAGAACATCTATTATTGCCAAAATAGAAGAATGAATTTATAGTTTTTATTAATATCCT
ATAAACGTTAGATGTCAAGGTGATTGGCTTAATGGTTTAAAAAACTGAAGTGATAATCTTGCATATTAAGGTTA

FIG. 9

```
GAAACTAATAAAGGTAACTAAAGGTGAATTATATTTGGTAATCTAGTCAAGATGCATGCAAAAAACTCGACAA
TTACCGTCCTAGAAAAATTTAGCTAACATGTAGAATATAATATGATTTTTTATTGAGCTGAGATTTTGATAGTG
ATCTTATTTTAATAGCAATATAATACAAGGGGTTCCGTAGTACAAATTTCATCCTATTAAGCTAGTGGGTTTTA
GTGCGGTGGTATGACGTGGCGACTGATTATTAGATGTGTAACTAACTACATAAAGGGAAATGTACGAATACG
TGGAGCCCACTGACCACTTTCAGTGGCCAATATTTGACTTTAACACACTGTATGGCACGTGAGGTCTGGTTTAG
AGAATAATACCCCGTCTCTTGGCTCTTAAAGTGCCCAAGAAGTTCATGACTTTGTACCTCCCATCATAGATAGC
CATAAAAATAAAATATCCCTAGTGATTTTTATCCCAATAAAATTCAAATATGTTCCAATTACATCTTTGTTTTTCG
AGGATGTGTATGACCAAAATAAAAAATATTACTCTCTATTTCAATTTAGATGATGTAGTTTGACTCGACACGGA
GTTTAAGAGAAAATAGGACTTTTAAAACTTGTGGTCTTAAAAACTTAAAGAGTAAAAGCTTTGTAGGCTAATG
TCATTTGTGTGGCTATAAAAACTTCTCATTAATGATAAAAGAATTAAAATGAAGAGTTTAAAGTTAAATTATTT
CCAAACTTAAAAATGCGTCATCTATTTTGGAACAAACTAAAAAGAAAAGTACTTCGTCACCCTGAATTCTATAC
TATTTAAACGTCCAATTTTAATAACGGAATAAAAAACTGCAGCTATGCAAAAGAAAAACTCTAATATTCTATT
GCATCTACTAGTTTATTCTTTAATTTCCTCGTACTTTTCTCTTTGTACTTTTTGGTTAAGCGATTGGTAAGAACTT
TTTTACATAGACTTTTGTTGTGGTCTGTTTTTAACCATATGATATTTCGAAAATAGTCTTAAATCTCTTCTTCATT
TGAAAGCCTTTAAATAATGACTAAGAAAGCAAGTAGCAAATGGATTTTATCAACTTGACTTTCTTGCCATAGCA
TTTTCGAAGCCTTAAAATGGCAAATATAGGTTAGTTGAGTCAACTTGACCTTCTAGCCCATAACATTTTATCCG
AAAAGGACTTAGGCCTTTTTCTAAGCCTCGATTGGTCCTACAATACAAGTATGTGGTATGACCACATTGTTTTG
GTAATTATGAAGAGGGTTGAATCGACTCTATGATGATAGCGTACAGCTTTCACCTGATCTTTTAACATTTCAGT
TTCGATAAATATCTCTTGAAGGACAAAATAATTGATACGTTTCACCCAATCTTTTATTTTAGTCCTATTTTTATCT
ATGTATTTGGATTAATTTCATGAAAAAAGACGTCATTTTTCTCTTATGAGAGTAAAAAAAATATAATGATATAG
AAATTATTGTTATTGTAGTTAAAATTGTTGCCATAAAATGCGTTCACTGTCTAGTACAACCATGGTGGAATAAC
TAGCGGGTTGTTCATTTTACATGTTATTCTTACTTGTCTTTATTAATATTTGTGGCCGAAGTGATCAAAGTGGAG
TGGTTCACGTATTAATTATATGAAAACAATTAAGAAATATGGTAAAATCGACTTTGTTGACCTTCAGTTCTTGC
ACTGATCTGGTTTGCAGAATCTTATTGACTTCTCACTGTCAATAATGTTTTTAATTTCTATTGTTATTTATTTGGG
GACCCCTACTTGATTGGGCAATCCCCCAACTTCCTACCCATTTTTCTATATCATTTTCCAAGTTGCTGACCAATAA
ATATAACTAATGAAAGTCATAAAATTGGGTCCCTAATGCTTGGTTATTCTAATATTCTTTTTGGCCATATCATTG
GAGTAATTCATTTGTTTAACATTGTTCTTTTTTCTTGGTTCCCATTTTCAGGAACAAGGCTCTGATGGTAGAAGC
AGGAATCTTATCAAGATTACCCCAAAAACCAGACAATTTAGATGGAAACACAAGGCAAGAATTTGCAGAATTG
ATCTTGTCTATATCATCCCTAGCCAACACCCAATTCAGTATGGATTCCTCAAGAATTATTCCATTTGTAGTCAGC
ATTCTTGATTCATCCAACTCAAGTGTTGAAACAAAAAGTACATGTCTAGGAACATTGTACAATTTATCCTCAGT
GCTGGAAAATGCTGCCATTTTGGCAACTAATGGAACAATGACTACTCTCTTTAGATTGTCTTCATTGAAGGAAG
TATCAGAGAAAGCATTAGCCACATTGGGAAATCTAGTAGTTACCTTAATGGGGAAGAAGGCAATGGAAGAAA
ATCCTATGGTGCCCGAGAGCTTAATCGAAATAATGACATGGGAAGAGAAGCCAAAATGTCAAGAATTATCGG
TCTATATTTTGATGATTTTGGCTCACCAGAGTTCTATTCAAAGGGAGAAAATGGCTAAGGCTGGTATTGTTCCA
GTTCTACTTGAAGTGGCATTGTTGAGTAGTCCTTTGGCTCAAAAAGAGCATTGAAATTATTACAATGGTTTAA
GGATGAAAGGCAGAGCAAATGGGACCTCACTCTGGGCCACAAGCAGGAAGGATAGCAATTGATTCACCACC
AGTGAGTCCAAGAGCCGTTGATGAAAGCAAGAAACTGATGAAGAAAATTGTGAAACAAAGCCTTCATAAAAA
TATGGAAACAATTACTAGTAGAGCCAATGGTGGTAGTGATTGTTCAAGGCTTAAGTCCCTAGTTGTTAGCTCA
AGTTCTAAGAGTTTGCCTTACTAAGAATGATCTTTTAAGCATTTTATTAAGTCTCACCTTGCACTACTTGTGCAA
TGTTCTGCAAGAATTTTTGTATCATATGAAAATATTTGTCCTTCAAACAAAAAGGAGTGATCTTAACCAAATA
ACAATAATCTATTGATTCGTTCCATTTGTG
```

FIG. 9 (Continued)

Nitab4.5_0002810g0020.2 Transcript:

SEQ ID NO: 3

ATGCCTAATACTTCAACAACTAGTAATTGGTATTTGACCTACATAAAGCTTAGGTTTTTCACAAAAGTCCGTCG
GTTCCTTCAGCTCAAGGCAGCATCTAAAAAGCCATTGAAACCGTCTGATCAGCCGAGAGAAAAATCAGATACT
TTGATCGTGATTGAAGAAGGTGAAAAGGGAGAAAAGGGTATAATGGGAAAAGAGAGTGATATTAAAGATAA
TGGATGGATGGTTTTGCAAAAATCTGTGAAGAAACTTCACTTTGGGAGTTCGGAAGAAAAGAGGTGGCAGC
CAAAGAGATAAAAAAGTTGGCTAAAGAAGACTTAAAGAGGAGGAAACTGATGGCGGAGCTGGGCGTAATTC
CGCCGCTTGTGGCCATGATTGGTGGTTCTGAGGTGGTGCTGCGGCGGCAGAGATTGGCTGTTCAAGCATTAG
TTGAGCTTGCCAATGGCTCTTTCACGAACAAGGCTCTGATGGTAGAAGCAGGAATCTTATCAAGATTACCCCA
AAAACCAGACAATTTAGATGGAAACACAAGGCAAGAATTTGCAGAATTGATCTTGTCTATATCATCCCTAGCC
AACACCCAATTCAGTATGGATTCCTCAAGAATTATTCCATTTGTAGTCAGCATTCTTGATTCATCCAACTCAAGT
GTTGAAACAAAAAGTACATGTCTAGGAACATTGTACAATTTATCCTCAGTGCTGGAAAATGCTGCCATTTTGGC
AACTAATGGAACAATGACTACTCTCTTTAGATTGTCTTCATTGAAGGAAGTATCAGAGAAAGCATTAGCCACAT
TGGGAAATCTAGTAGTTACCTTAATGGGGAAGAAGGCAATGGAAGAAAATCCTATGGTGCCCGAGAGCTTAA
TCGAAATAATGACATGGGAAGAGAAGCCAAAATGTCAAGAATTATCGGTCTATATTTTGATGATTTTGGCTCA
CCAGAGTTCTATTCAAAGGGAGAAAATGGCTAAGGCTGGTATTGTTCCAGTTCTACTTGAAGTGGCATTGTTG
AGTAGTCCTTTGGCTCAAAAAAGAGCATTGAAATTATTACAATGGTTTAAGGATGAAAGGCAGAGCAAAATG
GGACCTCACTCTGGGCCACAAGCAGGAAGGATAGCAATTGATTCACCACCAGTGAGTCCAAGAGCCGTTGAT
GAAAGCAAGAAACTGATGAAGAAAATTGTGAAACAAAGCCTTCATAAAAATATGGAAACAATTACTAGTAGA
GCCAATGGTGGTAGTGATTGTTCAAGGCTTAAGTCCCTAGTTGTTAGCTCAAGTTCTAAGAGTTTGCCTTACTA
A

FIG. 10 miRNA sequence:

SEQ ID NO: 6

ACAAACACACGCTCGGACGCATATTACACATGTTCATACACTTAATACTCGCTGTTTTGAATTGATGTTTTAGG
AATATATATGTAGATACGCCCAGCTCCGCCATCACTTCACAGGTCGTGATATGATTCAATTAGCTTCCGACTCA
TTCATCCAAATACCGAGTCGCCAAAATTCAAACTAGACTCGTTAAATGAATGAATGATGCGGTAGACAAATTG
GATCATTGATTCTCTTTGATGATGGCGGCGCTGGGCGTACACTCTCTCTTTTGTATTCCAATTTTCTTGATTAAT
CTTTCCTGCACAAAAACATGCTTGATCCACTAAGTGACATATATGCTGCCTTCGTATATATAGTTCTGGTAAAAT
TAACATTTTGGGTTTATCTTTATTTAAGGCATCGCCATG

FIG. 11

SEQUENCE LISTING

<160> NUMBER OF SEQ ID NOS: 6

<210> SEQ ID NO 1
<211> LENGTH: 436
<212> TYPE: PRT
<213> ORGANISM: Nicotiana tabacum

<400> SEQUENCE: 1

```
Met Pro Asn Thr Ser Thr Thr Ser Asn Trp Tyr Leu Thr Tyr Ile Lys
1               5                   10                  15

Leu Arg Phe Phe Thr Lys Val Arg Arg Phe Leu Gln Leu Lys Ala Ala
            20                  25                  30

Ser Lys Lys Pro Leu Lys Pro Ser Asp Gln Pro Arg Glu Lys Ser Asp
        35                  40                  45

Thr Leu Ile Val Ile Glu Glu Gly Glu Lys Gly Glu Lys Gly Ile Met
    50                  55                  60

Gly Lys Glu Ser Asp Ile Lys Asp Asn Gly Trp Met Val Leu Gln Lys
65                  70                  75                  80

Ser Val Lys Lys Leu His Phe Gly Ser Ser Glu Glu Lys Glu Val Ala
                85                  90                  95

Ala Lys Glu Ile Lys Lys Leu Ala Lys Glu Asp Leu Lys Arg Arg Lys
            100                 105                 110

Leu Met Ala Glu Leu Gly Val Ile Pro Pro Leu Val Ala Met Ile Gly
        115                 120                 125

Gly Ser Glu Val Val Leu Arg Arg Gln Arg Leu Ala Val Gln Ala Leu
    130                 135                 140

Val Glu Leu Ala Asn Gly Ser Phe Thr Asn Lys Ala Leu Met Val Glu
145                 150                 155                 160

Ala Gly Ile Leu Ser Arg Leu Pro Gln Lys Pro Asp Asn Leu Asp Gly
                165                 170                 175

Asn Thr Arg Gln Glu Phe Ala Glu Leu Ile Leu Ser Ile Ser Ser Leu
            180                 185                 190
```

Ala Asn Thr Gln Phe Ser Met Asp Ser Ser Arg Ile Ile Pro Phe Val
            195                 200                 205

Val Ser Ile Leu Asp Ser Ser Asn Ser Ser Val Glu Thr Lys Ser Thr
210                 215                 220

Cys Leu Gly Thr Leu Tyr Asn Leu Ser Ser Val Leu Glu Asn Ala Ala
225                 230                 235                 240

Ile Leu Ala Thr Asn Gly Thr Met Thr Thr Leu Phe Arg Leu Ser Ser
            245                 250                 255

Leu Lys Glu Val Ser Glu Lys Ala Leu Ala Thr Leu Gly Asn Leu Val
            260                 265                 270

Val Thr Leu Met Gly Lys Lys Ala Met Glu Glu Asn Pro Met Val Pro
            275                 280                 285

Glu Ser Leu Ile Glu Ile Met Thr Trp Glu Gly Lys Pro Lys Cys Gln
290                 295                 300

Glu Leu Ser Val Tyr Ile Leu Met Ile Leu Ala His Gln Ser Ser Ile
305                 310                 315                 320

Gln Arg Glu Lys Met Ala Lys Ala Gly Ile Val Pro Val Leu Leu Glu
            325                 330                 335

Val Ala Leu Leu Ser Ser Pro Leu Ala Gln Lys Arg Ala Leu Lys Leu
            340                 345                 350

Leu Gln Trp Phe Lys Asp Glu Arg Gln Ser Lys Met Gly Pro His Ser
            355                 360                 365

Gly Pro Gln Ala Gly Arg Ile Ala Ile Asp Ser Pro Val Ser Pro
            370                 375                 380

Arg Ala Val Asp Glu Ser Lys Lys Leu Met Lys Ile Val Lys Gln
385                 390                 395                 400

Ser Leu His Lys Asn Met Glu Thr Ile Thr Ser Arg Ala Asn Gly Gly
            405                 410                 415

Ser Asp Cys Ser Arg Leu Lys Ser Leu Val Val Ser Ser Ser Lys
            420                 425                 430

Ser Leu Pro Tyr
            435

<210> SEQ ID NO 2
<211> LENGTH: 4253
<212> TYPE: DNA
<213> ORGANISM: Nicotiana tabacum

<400> SEQUENCE: 2

```
ccgatgtaac tgacatatcg tgaatctgca tgtgctttct gctcttcttg ttttgttgcc    60
ctcaaagtct tcttctctct tgtctgctt  cttttccaac taattctttc tttcaccaaa   120
agtcagatat aaacacactt aatttaaaac cttttagaat tcaattaaa  ccaccccctac  180
ccctacccct accccccacca cggccccctac aaaaccgttc ttcttcatat atgtcctctt  240
cacgagtagt atatatcgaa acatgcctaa tacttcaaca actagtaatt ggtatttgac   300
ctacataaag cttaggtttt tcacaaaagt ccgtcggttc cttcagctca aggcagcatc   360
taaaaagcca ttgaaaccgt ctgatcagcc gagagaaaaa tcagatactt tgatcgtgat   420
tgaagaaggt gaaagggag  aaagggtat  aatgggaaaa gagagtgata ttaaagataa   480
tggatggatg gttttgcaaa aatctgtgaa gaaacttcac tttgggagtt cggaagaaaa   540
agaggtggca gccaaagaga taaaaaagtt ggctaaagaa gacttaaaga ggaggaaact   600
gatggcggag ctgggcgtaa ttccgccgct tgtggccatg attggtggtt ctgaggtggt   660
```

```
gctgcggcgg cagagattgg ctgttcaagc attagttgag cttgccaatg gctctttcac      720
gtaagttcat ttacttataa ttttataaat cataaatatt aatcactcgt ttaagtaaaa      780
tccttttta ttttatttta tcaattaatc cactttcttc ttcatgcttg gttttctcct      840
cggctaatag ttacgatcaa gtttaagtgc taagtttgac gctgcactaa tatatgtgtt      900
tatcgtaaaa acgataagaa caagaatcat gaatttataa caatttgtaa ttttataata      960
atgtgagatt ttttcatcac attaagtaag aaatttgtaa aggtgaagtt caaattttat     1020
cccatattcg tgaactggag aactgatttt aaaatttaat taaatcgcat tatccatttt     1080
ggaaaagcaa atggcatgtt aattttctgt ttcgtgattt ctttcagtaa agaacatcta     1140
ttattgccaa aatagaagaa tgaatttata gttttttatta atatcctata aacgttagat     1200
gtcaaggtga ttggcttaat ggtttaaaaa ctgaagtgat aatcttgcat attaaggtta     1260
gaaactaata aaggtaacta aaggtgaatt atatttggta atctagtcaa gatgcatgca     1320
aaaaactcga caattaccgt cctagaaaaa tttagctaac atgtagaata taatatgatt     1380
ttttattgag ctgagatttt gatagtgatc ttatttaat agcaatataa tacaagggt     1440
tccgtagtac aaatttcatc ctattaagct agtgggtttt agtgcggtgg tatgacgtgg     1500
cgactgatta ttagatgtgt aactaactac ataaagggaa atgtacgaat acgtggagcc     1560
cactgaccac tttcagtggc caatatttga ctttaacaca ctgtatggca cgtgaggtct     1620
ggtttagaga ataatacccc gtctcttggc tcttaaagtg cccaagaagt tcatgacttt     1680
gtacctccca tcatagatag ccataaaaat aaaatatccc tagtgatttt tatcccaata     1740
aaattcaaat atgttccaat tacatctttg tttttcgagg atgtgtatga ccaaaataaa     1800
aaatattact ctctatttca atttagatga tgtagtttga ctcgacacgg agtttaagag     1860
aaaataggac ttttaaaact tgtggtctta aaaacttaaa gagtaaaagc tttgtaggct     1920
aatgtcattt gtgtggctat aaaaacttct cattaatgat aaaagaatta aaatgaagag     1980
tttaaagtta aattatttcc aaacttaaaa atgcgtcatc tattttggaa caaactaaaa     2040
agaaaagtac ttcgtcaccc tgaattctat actatttaaa cgtccaattt taataacgga     2100
ataaaaaact gcagctatgc aaaaagaaaa actctaatat tctattgcat ctactagttt     2160
attctttaat ttcctcgtac ttttctcttt gtactttttg gttaagcgat tggtaagaac     2220
tttttttacat agactttgt tgtggtctgt ttttaaccat atgatatttc gaaaatagtc     2280
ttaaatctct tcttcatttg aaagccttta ataatgact aagaaagcaa gtagcaaatg     2340
gattttatca acttgacttt cttgccatag cattttcgaa gccttaaaat ggcaaatata     2400
ggttagttga gtcaacttga ccttctagcc cataacattt tatccgaaaa ggacttaggc     2460
ctttttctaa gcctcgattg gtcctacaat acaagtatgt ggtatgacca cattgttttg     2520
gtaattatga agagggttga atcgactcta tgatgatagc gtacagcttt cacctgatct     2580
tttaacattt cagtttcgat aaatatctct tgaaggacaa ataattgat acgtttcacc     2640
caatcttta ttttagtcct atttttatct atgtatttgg attaatttca tgaaaaaga     2700
cgtcattttt ctcttatgag agtaaaaaaa ataatgat atagaaatta ttgttattgt     2760
agttaaaatt gttgccataa aatgcgttca ctgtctagta caaccatggt ggaataacta     2820
gcgggttgtt cattttacat gttattctta cttgtcttta ttaatatttg tggccgaagt     2880
gatcaaagtg gagtggttca cgtattaatt atatgaaaac aattaagaaa tatggtaaaa     2940
tcgactttgt tgaccttcag ttcttgcact gatctggttt gcagaatctt attgacttct     3000
cactgtcaat aatgttttta atttctattg ttatttattt ggggacccct acttgattgg     3060
```

```
gcaatccccc aacttcctac ccattttttct atatcattttt ccaagttgct gaccaataaa    3120
tataactaat gaaagtcata aaattgggtc cctaatgctt ggttattcta atattctttt    3180
tggccatatc attggagtaa ttcatttgtt taacattgtt cttttttctt ggttcccatt    3240
ttcaggaaca aggctctgat ggtagaagca ggaatcttat caagattacc ccaaaaacca    3300
gacaatttag atggaaacac aaggcaagaa tttgcagaat tgatcttgtc tatatcatcc    3360
ctagccaaca cccaattcag tatggattcc tcaagaatta ttccatttgt agtcagcatt    3420
cttgattcat ccaactcaag tgttgaaaca aaaagtacat gtctaggaac attgtacaat    3480
ttatcctcag tgctggaaaa tgctgccatt ttggcaacta atggaacaat gactactctc    3540
tttagattgt cttcattgaa ggaagtatca gagaaagcat tagccacatt gggaaatcta    3600
gtagttacct taatggggaa gaaggcaatg gaagaaaatc ctatggtgcc cgagagctta    3660
atcgaaataa tgacatggga agagaagcca aaatgtcaag aattatcggt ctatattttg    3720
atgattttgg ctcaccagag ttctattcaa agggagaaaa tggctaaggc tggtattgtt    3780
ccagttctac ttgaagtggc attgttgagt agtccttttgg ctcaaaaaag agcattgaaa    3840
ttattacaat ggtttaagga tgaaaggcag agcaaaatgg acctcactc tgggccacaa    3900 gcaggaagga tagcaattga ttcaccacca gtgagtccaa gagccgttga tgaaagcaag    3960
aaactgatga gaaaaattgt gaaacaaagc cttcataaaa atatgaaaac aattactagt    4020
agagccaatg gtggtagtga ttgttcaagg cttaagtccc tagttgttag ctcaagttct    4080
aagagtttgc cttactaaga atgatctttt aagcattttta ttaagtctca ccttgcacta    4140
cttgtgcaat gttctgcaag aattttttgta tcatatgaaa atatttgtcc ttcaaacaaa    4200
aaaggagtga tcttaaccaa ataacaataa tctattgatt cgttccattt gtg    4253

<210> SEQ ID NO 3
<211> LENGTH: 1311
<212> TYPE: DNA
<213> ORGANISM: Nicotiana tabacum

<400> SEQUENCE: 3
atgcctaata cttcaacaac tagtaattgg tatttgacct acataaagct taggtttttc     60
acaaaagtcc gtcggttcct tcagctcaag gcagcatcta aaaagccatt gaaaccgtct    120
gatcagccga gagaaaaatc agatactttg atcgtgattg aagaaggtga aaagggagaa    180
aagggtataa tggaaaagaa gagtgatatt aaagataatg gatggatggt tttgcaaaaa    240
tctgtgaaga aacttcactt tgggagttcg aagaaaaag aggtggcagc caagagata    300 aaaaagttgg ctaaagaaga cttaagagg aggaaactga tggcggagct gggcgtaatt    360
ccgccgcttg tggccatgat tggtggttct gaggtggtgc tgcggcggca gagattggct    420
gttcaagcat tagttgagct tgccaatggc tctttcacga caaggctct gatggtagaa    480 gcaggaatct tatcaagatt accccaaaaa ccagacaatt tagatggaaa acaaggcaa    540 gaatttgcag aattgatctt gtctatatca tccctagcca cacccaatt cagtatggat    600 tcctcaagaa ttattccatt tgtagtcagc attcttgatt catccaactc aagtgttgaa    660
acaaaaagta catgtctagg aacattgtac aattatcct cagtgctgga aaatgctgcc    720
attttggcaa ctaatggaac aatgactact ctctttagat tgtcttcatt gaaggaagta    780
tcagagaaag cattagccac attgggaaat ctagtagtta ccttaatggg gaagaaggca    840
atggaagaaa atcctatggt gcccgagagc ttaatcgaaa taatgacatg ggaagagaag    900
```

```
ccaaaatgtc aagaattatc ggtctatatt ttgatgattt tggctcacca gagttctatt    960
caaagggaga aaatggctaa ggctggtatt gttccagttc tacttgaagt ggcattgttg   1020
agtagtcctt tggctcaaaa aagagcattg aaattattac aatggtttaa ggatgaaagg   1080
cagagcaaaa tgggacctca ctctgggcca caagcaggaa ggatagcaat tgattcacca   1140
ccagtgagtc caagagccgt tgatgaaagc aagaaactga tgaagaaaat tgtgaaacaa   1200
agccttcata aaaatatgga aacaattact agtagagcca atggtggtag tgattgttca   1260
aggcttaagt ccctagttgt tagctcaagt tctaagagtt tgccttacta a            1311

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
tgagtaaggt taccgaattc                                                 20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ctcgaggccc gggcatgtcc                                                 20

<210> SEQ ID NO 6
<211> LENGTH: 410
<212> TYPE: DNA
<213> ORGANISM: Artificial Sequence
<220> FEATURE:
<223> OTHER INFORMATION: amiRNA sequence

<400> SEQUENCE: 6
acaaacacac gctcggacgc atattacaca tgttcataca cttaatactc gctgttttga     60
attgatgttt taggaatata tatgtagata cgcccagctc cgccatcact tcacaggtcg    120
tgatatgatt caattagctt ccgactcatt catccaaata ccgagtcgcc aaaattcaaa    180
ctagactcgt taaatgaatg aatgatgcgg tagacaaatt ggatcattga ttctctttga    240
tgatggcggc gctgggcgta cactctctct tttgtattcc aattttcttg attaatcttt    300
cctgcacaaa aacatgcttg atccactaag tgacatatat gctgccttcg tatatatagt    360
tctggtaaaa ttaacatttt gggtttatct ttatttaagg catcgccatg                410
```

METHODS AND MEANS FOR MODIFYING THE ALKALOID CONTENT OF PLANTS

CROSS REFERENCE TO RELATED APPLICATIONS

This is a U.S. National Phase application claiming priority to PCT/GB2019/053226, filed Nov. 14, 2019, the entire contents of which are hereby expressly incorporated by reference in its entirety including, without limitation, the specification, claims, and abstract, as well as any figures, tables, or drawings thereof.

FIELD OF THE INVENTION

The present invention relates to methods of modulating the alkaloid content e.g. nicotine content of a plant or part thereof. The invention also extends to methods of modulating the expression of polypeptides encoded by genes which modulate alkaloid content within plants. Alternatively, the invention provides methods of modulating the expression of genes which encode polypeptides which modulate alkaloid content within plants. The invention also extends to constructs, which can be used to modulate the polypeptides, plant cells transformed with such constructs, and to transgenic plants themselves. The invention also relates to the use of harvested leaves from such transgenic plants which have been transformed with a genetic construct for modulating alkaloid content, and smoking articles (e.g. combustible smoking articles) comprising such leaves.

BACKGROUND

Alkaloids are a group of naturally occurring compounds which mostly contain basic nitrogen atoms and are produced by a large variety of organisms including bacteria, fungi, plants and animals.

Alkaloids may be classified according to the similarity of the carbon skeleton e.g. indole-, isoquinoline- and pyridine-like. Pyridine derivatives are one class of monomeric alkaloids; this class includes simple derivatives of pyridine, polycyclic condensed and noncondensing pyridine derivatives and sesquiterpene pyridine derivatives. Examples are nicotine, nornicotine, anabasine, myosmine and anatabine.

Most of the known biological functions of alkaloids are related to protection. Neuroactive molecules, like caffeine, cocaine, morphine, and nicotine, act as defence compounds against invading predators. The accumulation of these alkaloids is the result of signal transduction cascades that monitor gene expression, enzyme activities, and alkaloid concentrations. The fine-tuning of alkaloid content in the plant involves negative feedback loops and degradative pathways.

Nicotine occurs naturally in several varieties of plant but is found at the highest level in the tobacco plant. Cultivated tobacco produce 2-4% alkaloids of total dry weight. Nicotine is produced in wild and cultivated *Nicotiana* species and it plays an important role in plant defence against herbivores and insects (Voelckel et al. 2001, incorporated herein by reference), accounting for ~90% of the total alkaloid content. The remaining 10% of the alkaloid pool is mostly constituted by the structurally related compounds nornicotine, anatabine, anabasine and pseudoxynicotine (PON).

The regulation of alkaloid content in tobacco is complex. Several factors including genotype, environment, fertilization and agronomic practices (e.g. topping) affect alkaloid levels in tobacco plants. Some key regulators of nicotine biosynthesis are well characterized, for example putrescine N-methyltransferase (PMT), which plays a pivotal role in this pathway, is activated by members of the ethylene responsive factor (ERF) superfamily, the largest transcription factor family in the tobacco genome (Rushton et al., 2008 incorporated herein by reference). Other transcription factors that induce alkaloid biosynthesis belong to the MYC2-like basic helix-loop-helix (bHLH) family. MYC2-like bHLHs regulate alkaloid levels directly, through the Gbox-mediated binding and activation of alkaloid structural genes, and indirectly, through the activation of ERFs.

Modifying alkaloid content in plants (e.g. tobacco) can have several commercial advantages. For example, decreasing total alkaloid content in plants can increase the value of said plant as a biomass resource. For example, modifying alkaloid content may comprise reducing the alkaloid content e.g. nicotine content of tobacco plants. Tobacco plants and products with reduced nicotine may be desirable in view of the potential regulation of "nicotine ceilings" i.e. average upper limits of nicotine in tobacco products. Alternatively, increasing alkaloid content in plants e.g. tobacco plants, can help to protect plants against insects and herbivores. There remains a need for plants with modulated alkaloid content, for example with modulated nicotine content, with improved commercially desirable traits and methods for making the same.

During the post-harvest leaf curing, reactions between pyridine alkaloids and nitrosating species leads to the formation of tobacco-specific nitrosamines (TSNAs). Nornicotine and PON are the precursors of the TSNAs NNN and NNK respectively. Reducing the production and accumulation of nornicotine and PON is of high importance. The CYP82E family of nicotine demethylase genes is the primary regulator of nicotine to nornicotine conversion, and altering their activity or accumulation results in a decrease in NNN levels. However, no enzymes or genes responsible for producing PON have been identified thus far.

As described in the Examples, the inventors sought to investigate genes responsible for alkaloid synthesis, with the aim of modulating alkaloid content in plants, e.g. decreasing nicotine content in tobacco plants.

SUMMARY OF THE INVENTION

It has been surprisingly found that by modulating the expression of an armadillo repeat protein or by modifying the nucleic acid sequence of at least one gene encoding an armadillo repeat protein as taught herein, the alkaloid content and/or TSNA content or precursor of TSNA content of plants can be modulated. The gene encoding an armadillo repeat protein as taught herein acts as a positive regulator of nicotine biosynthesis. Nitab4.5_0002810g0020.2 is taught herein as positive regulator of nicotine, nornicotine and PON in cultivated tobacco. Nitab4.5_0002810g0020.2 encodes an Armadillo (Arm) repeat protein. These proteins contain tandem copies of a degenerate protein sequence motif of approximately 40 amino acids that forms a conserved three-dimensional structure. The function of these proteins is usually determined by characteristic sequences outside the Arm domain.

According to the present invention, tobacco products with modulated alkaloid content and commercially desirable traits sought after by consumers of tobacco products can be produced. In some instances, consumers may desire a product with low levels of alkaloid content e.g. low levels of nicotine content.

The present invention may be particularly useful in the field of plant molecular farming, where plants (such as tobacco and other *Nicotiana* spp.) are used for the production of proteins, peptides, and metabolites e.g. for the production of therapeutics and pharmaceuticals such as antibiotics, virus like particles, or neutraceuticals or small molecules. Tobacco has been used for the development of an HIV-neutralising antibody in an EU-funded project called PharmPlant and Medicago Inc., Canada have worked on a tobacco-based platform for the production of virus-like particles for flu vaccine manufacture.

Thus a plant according to the present invention may be used for molecular farming to reduce or eliminate the presence of nicotine, nornicotine, PON and/or other nicotinic alkaloids. The use of a low nicotine plant or rootsock is beneficial in molecular farming and would reduce downstream processing costs associated with purification.

In other instances it may be desirable to produce plants with high alkaloid levels e.g. high levels of nicotine content so that nicotine may be purified from the tobacco plant to produce a pure nicotine product for example for use in devices which utilize liquid containing nicotine (e.g. e-cigarettes) or within tobacco heating devices. For example, the production of plants with leaves containing high levels of nicotine could reduce costs of nicotine extraction for the production of e-liquids for e-cigarettes.

The present inventors have surprisingly determined a method for modulating the alkaloid content, e.g. nicotine content, of a plant (e.g. a tobacco plant) by modulating the expression or nucleic acid sequence of gene encoding an armadillo repeat protein which acts as a positive regulator of nicotine in tobacco or by modifying the nucleic acid sequence of at least one gene encoding an armadillo repeat protein which acts as a positive regulator of nicotine in tobacco. The alkaloid content (e.g. nicotine content) of a plant (e.g. tobacco plant) may be decreased by decreasing the expression of gene encoding an armadillo repeat protein or by modifying the nucleic acid sequence of at least one gene encoding an armadillo repeat protein (for example by disrupting the armadillo repeat domain) or may be increased by increasing the expression of gene encoding an armadillo repeat protein or by modifying the nucleic acid sequence of at least one gene encoding an armadillo repeat protein (for example by increasing the binding affinity of the armadillo repeat domain). Prior to the present invention it had not been known that modulation of the expression of gene encoding an armadillo repeat protein or modification of the nucleic acid sequence of at least one gene encoding an armadillo repeat protein as described herein could be used to modulate alkaloid content.

In one aspect, there is provided a method of modulating (e.g. decreasing) the alkaloid content of a plant or a part thereof, or a cell culture, the method comprising modifying said plant or a cell culture by modulating the expression of at least one gene encoding an armadillo repeat protein or by modifying the nucleic acid sequence of at least one gene encoding an armadillo repeat protein.

In another aspect, there is provided a method of modulating (e.g. decreasing) the content of a tobacco specific nitrosamine (TSNA) or a precursor of a TSNA in a tobacco plant or plant part thereof, the method comprising modifying said plant or a cell culture by modulating the expression of at least one gene encoding an armadillo repeat protein or by modifying the nucleic acid sequence of at least one gene encoding an armadillo repeat protein.

In a further aspect there is provided the use of at least one gene encoding an armadillo repeat protein for modulating alkaloid content of a cell or plant or part thereof or a cell culture.

In yet another aspect, there is provided a method for producing a plant or part thereof, a cell culture, a plant propagation material, a leaf, a cut harvested leaf, a processed leaf or a cut and processed leaf which has modulated (e.g. decreased) alkaloid content, the method comprising: modifying said plant or cell culture to modulate the expression of at least one gene encoding an armadillo repeat protein; or modifying the nucleic acid sequence of at least one gene encoding an armadillo repeat protein.

In one aspect, the present invention provides a method of modulating (e.g. decreasing) the alkaloid content of a plant or a part thereof, or a cell culture, the method comprising modifying said plant or a cell culture: by modulating (e.g. decreasing) the expression of at least one armadillo repeat protein which:
a) comprises an amino acid sequence as set out in: SEQ ID No. 1 or a functional variant or functional fragment or orthologue thereof, or a sequence which has at least 80% identity to SEQ ID No. 1; or
b) is encoded by a nucleotide sequence as set out in SEQ ID No. 2 or 3; or a functional variant or functional fragment or orthologue of SEQ ID No. 2 or 3; or a nucleic acid sequence which has at least 80% identity to SEQ ID No. 2 or 3.

In a further aspect, the present invention provides a method of modulating (e.g. decreasing) the content of a tobacco specific nitrosamine (TSNA) or a precursor of a TSNA in a tobacco plant or plant part thereof, the method comprising modifying said plant or a cell culture: by modulating (e.g. decreasing) the expression of at least one armadillo repeat protein which:
a) comprises an amino acid sequence as set out in: SEQ ID No. 1 or a functional variant or functional fragment or orthologue thereof, or a sequence which has at least 80% identity to SEQ ID No. 1; or
b) is encoded by a nucleotide sequence as set out in SEQ ID No. 2 or 3; or a functional variant or functional fragment or orthologue of SEQ ID No. 2 or 3; or a nucleic acid sequence which has at least 80% identity to SEQ ID No. 2 or 3.

In another aspect the present invention provides the use of at least one gene encoding an armadillo repeat protein for modulating alkaloid content of a cell or plant or part thereof or a cell culture; wherein the armadillo repeat protein:
a) comprises an amino acid sequence as set out in: SEQ ID No. 1 or a functional variant or functional fragment or orthologue thereof, or a sequence which has at least 80% identity to SEQ ID No. 1; or
b) is encoded by a nucleotide sequence as set out in SEQ ID No. 2 or 3; or a functional variant or functional fragment or orthologue of SEQ ID No. 2 or 3; or a nucleic acid sequence which has at least 80% identity to SEQ ID No. 2 or 3.

Also provided by the present invention is a method for producing a plant or part thereof, a cell culture, a plant propagation material, a leaf, a cut harvested leaf, a processed leaf or a cut and processed leaf which has modulated (e.g. decreased) alkaloid content, the method comprising modifying said plant or cell culture to: modulate (e.g. decrease) the expression of at least one armadillo repeat protein which:
a) comprises an amino acid sequence as set out in: SEQ ID No. 1 or a functional variant or functional fragment or orthologue thereof, or a sequence which has at least 80% identity to SEQ ID No. 1; or b) is encoded by a nucleotide sequence as set out in SEQ ID No. 2 or 3; or a functional variant or functional fragment or orthologue of SEQ ID No. 2 or 3; or a nucleic acid sequence which has at least 80% identity to SEQ ID No. 2 or 3.

Suitably, the at least one gene encoding an armadillo repeat protein may encode an amino acid sequence as set out in: SEQ ID No. 1 or a functional variant or functional fragment or orthologue thereof, or a sequence which has at least 80% identity to SEQ ID No. 1; or wherein the at least one gene encoding an armadillo repeat protein comprises a nucleic acid sequence as set out in SEQ ID No. 2 or 3; or a functional variant or functional fragment or orthologue of SEQ ID No. 2 or 3 or a nucleic acid sequence which has at least 80% identity to SEQ ID No. 2 or 3.

Suitably, the alkaloid content may be modulated (e.g. decreased) in comparison to a plant or cell culture which has not been modified to: modulate the expression of the at least one armadillo repeat protein; or modify the nucleic acid sequence of at least one gene encoding an armadillo repeat protein.

In a further aspect, the present invention provides a plant or part thereof or a cell culture which has been modified to achieve a modulation (e.g. decrease) in alkaloid content in comparison to an unmodified plant or unmodified cell culture, wherein the modification is the modulation of the expression of at least one armadillo repeat protein which:

a) comprises an amino acid sequence as set out in: SEQ ID No. 1 or a functional variant or functional fragment or orthologue thereof, or a sequence which has at least 80% identity to SEQ ID No. 1; or b) is encoded by a nucleotide sequence as set out in SEQ ID No. 2 or 3; or a functional variant or functional fragment or orthologue of SEQ ID No. 2 or 3; or a nucleic acid sequence which has at least 80% identity to SEQ ID No. 2 or 3.

In one aspect, there is provided a plant or part thereof or a cell culture which has been modified to achieve a modulation (e.g. decrease) in alkaloid content in comparison to an unmodified plant or unmodified cell culture, wherein the modification is the modulation of the expression of at least one gene encoding an armadillo repeat protein the at least one gene encoding an armadillo repeat protein or the modification of the nucleic acid sequence of at least one gene encoding an armadillo repeat protein; wherein the armadillo repeat protein comprises an amino acid sequence as set out in: SEQ ID No. 1 or a functional variant or functional fragment or orthologue thereof, or a sequence which has at least 80% identity to SEQ ID No. 1; or wherein the at least one gene encoding an armadillo repeat protein comprises a nucleic acid sequence as set out in SEQ ID No. SEQ ID No. 2 or 3; or a functional variant or functional fragment or orthologue of SEQ ID No. 2 or 3 or a nucleic acid sequence which has at least 80% identity to SEQ ID No. 2 or 3.

In a further aspect, there is provided a plant propagation material obtainable (e.g. obtained) from a plant according to the present invention or from a plant or cell culture produced by the method according to the present invention.

In a further aspect, there is provided a method or use according to the present invention, or a plant or part thereof or cell culture according to the present invention, or a plant propagation material according to the present invention, wherein the alkaloid content of the plant is decreased in comparison to a plant or cell culture which has not been modified to modulate the expression of at least one gene encoding an armadillo repeat protein or to modify the nucleic acid sequence of at least one gene encoding an armadillo repeat protein.

Suitably, the expression of at least one gene encoding an armadillo repeat protein may be decreased in comparison to a plant or part thereof or cell or cell culture which has not been modified to modulate the expression of the at least one gene encoding an armadillo repeat protein.

Suitably, the alkaloid content of the plant or part thereof or cell or cell culture may be increased in comparison to a plant which has not been modified to modulate the expression of the at least one armadillo repeat protein or to modify the nucleic acid sequence of at least one gene encoding an armadillo repeat protein.

Suitably the plant may be modified to increase the expression of at least one gene encoding an armadillo repeat protein or to modify the nucleic acid sequence of at least one armadillo repeat protein; and the plant or cell culture exhibits increased alkaloid content in comparison to a plant or cell culture which has not been modified to modulate the expression of the at least one armadillo repeat protein.

Suitably, the total alkaloid content of the plant or cell culture may be modulated. Suitably, the content of one or more alkaloids selected from nicotine, nornicotine, PON, anabasine, myosmine and anatabine may be modulated (e.g. decreased), preferably the content of nicotine, nornicotine and/or PON is modulated (e.g. decreased).

In one aspect, the plant or plant cell is from the Solanaceae family.

Suitably, the plant or plant cell may be from the *Solanum* genus.

Suitably, the plant or plant cell may be from the *Nicotiana* genus.

Suitably, the nicotine content may be modulated. Suitably the nicotine content may be decreased.

In one aspect there is provided a method or use according to the present invention, a plant or part thereof or cell culture according to the present invention, or a plant propagation material according to the present invention wherein the at least one gene encoding an armadillo repeat protein comprises an amino acid sequence as set out in: SEQ ID No. 1 or a functional variant or functional fragment or orthologue thereof, or a sequence which has at least 80% identity to SEQ ID No. 1; or wherein the at least one gene encoding an armadillo repeat protein comprises a nucleic acid sequence as set out in SEQ ID No. SEQ ID No. 2 or 3; or a functional variant or functional fragment or orthologue of SEQ ID No. 2 or 3 or a nucleic acid sequence which has at least 80% identity to SEQ ID No. 2 or 3.

In a further aspect, there is provided a method or use according to the present invention, a plant or part thereof or cell culture according to the present invention, or a plant propagation material according to the present invention wherein an additional gene encoding an armadillo repeat protein is modulated wherein the additional gene comprises a nucleotide sequence as set forth in SEQ ID No. 2 or 3; or a functional variant or functional fragment or orthologue of SEQ ID No. 2 or 3 or a nucleic acid sequence which has at least 80% identity to SEQ ID No. 2 or 3.

In a further aspect, the present invention provides the use of a nucleotide sequence encoding an armadillo repeat protein which:

a) comprises an amino acid sequence as set out in: SEQ ID No. 1 or a functional variant or functional fragment or orthologue thereof, or a sequence which has at least 80% identity to SEQ ID No. 1; or b) is encoded by a nucleotide sequence as set out in SEQ ID No. 2 or 3; or a functional variant or functional fragment or orthologue of SEQ ID No. 2 or 3; or a nucleic acid sequence which has at least 80% identity to SEQ ID No. 2 or 3, to select a plant having modulated (e.g. reduced) alkaloid content and/or modulated (e.g. reduced) content of tobacco specific nitrosamine (TSNA) or a precursor of a TSNA.

In one aspect there is provided the use of a plant or part thereof or cell culture according to the present invention, or of a plant produced by the method to the present invention to breed a plant.

In another aspect, there is provided the use of a plant or part thereof or a cell culture according to the present invention, or of a plant produced by the method to the present invention for production of a product.

In yet another aspect, there is provided the use of a plant or part thereof according to the present invention, or of a plant produced by the method according to the present invention grow a crop.

In another aspect there is provided the use of a plant or part thereof according to the present invention, or of a plant produced according to the present invention produce a leaf.

In another aspect, there is provided a harvested leaf of a plant according to the present invention, or obtainable (e.g. obtained) (or obtained) from a plant propagated from a propagation material according to the present invention, or obtainable (e.g. obtained) (or obtained) from a plant obtained by a use according to the present invention, or obtainable (e.g. obtained) (or obtained) from a plant produced by the method according to the present invention.

In one aspect, the harvested leaf of a plant is a cut harvested leaf.

In another aspect, there is provided a processed leaf, preferably a processed tobacco leaf, preferably a non-viable processed tobacco leaf:
  obtainable (e.g. obtained) (or obtained) from a plant obtainable (e.g. obtained) from a use according to the present invention;
  obtainable (e.g. obtained) (or obtained) by processing a plant according to the present invention;
  obtainable (e.g. obtained) (or obtained) from a plant propagated from a plant propagation material according to the present invention; or
  obtainable (e.g. obtained) (or obtained) by processing a harvested leaf of a plant according to the present invention; or
  obtainable (e.g. obtained) (or obtained) from a plant produced by the method according to the present invention.

In one aspect, the leaf is processed by curing, fermenting, pasteurizing or a combination thereof.

Suitably, the processed leaf may be a cut processed leaf.

In another aspect, there is provided cured tobacco material made from a plant or a part thereof according to the present invention or an extract thereof.

In a further aspect, there is provided a tobacco blend comprising said cured tobacco material according to the present invention.

In another aspect, there is provided a tobacco industry product prepared from:
  a tobacco plant according to the present invention, or a part thereof or a tobacco cell culture according to the present invention;
  a tobacco plant or part thereof propagated from a tobacco plant propagation material according to the present invention;
  a harvested leaf of a plant according to the present invention, wherein the plant is tobacco;
  a processed leaf according to the present invention, wherein the plant is tobacco; or
  a plant produced by the method according to the present invention.

In one aspect, the tobacco product is a combustible smoking article.

In another aspect, the tobacco product is a smokeless tobacco product.

Suitably, the tobacco product may be a non-combustible aerosol provision system such as a tobacco heating device or an aerosol-generating device.

In one aspect, there is provided the use of a tobacco cell according the present invention, for modulating alkaloid content in cell cultures.

In one aspect, there is provided a combustible smoking article, non-combustible aerosol provisioning system, smokeless tobacco product or tobacco heating device comprising a plant or a part thereof according to the present invention or an extract (e.g. a tobacco extract) thereof or a tobacco cell culture according to the present invention; or a cured tobacco material according to the present invention; or a tobacco blend according to the present invention.

In a further aspect, there is provided the use of a nucleotide sequence of at least one gene encoding an armadillo repeat protein preferably where the sequence of the armadillo repeat protein is selected from: SEQ ID No. 1 or a functional variant or functional fragment or orthologue thereof, or a sequence which has at least 80% identity to SEQ ID No. 1; or wherein the at least one gene encoding an armadillo repeat protein comprises a nucleic acid sequence as set out in SEQ ID No. SEQ ID No. 2 or 3; or a functional variant or functional fragment or orthologue of SEQ ID No. 2 or 3 or a nucleic acid sequence which has at least 80% identity to SEQ ID No. 2 or 3, to select a plant having modulated (e.g. reduced) alkaloid content and/or modulated (e.g. reduced) content of tobacco specific nitrosamine (TSNA) or a precursor of a TSNA.

In another aspect, the present invention provides a mutant of a plant carrying a heritable mutation in a nucleotide sequence which:
  a) comprises an amino acid sequence as set out in: SEQ ID No. 1 or a functional variant or functional fragment or orthologue thereof, or a sequence which has at least 80% identity to SEQ ID No. 1; or
  b) is encoded by a nucleotide sequence as set out in SEQ ID No. 2 or 3; or a functional variant or functional fragment or orthologue of SEQ ID No. 2 or 3; or a nucleic acid sequence which has at least 80% identity to SEQ ID No. 2 or 3,
  wherein said heritable mutation modulates (e.g. decreases) the expression of the armadillo repeat protein and wherein the mutant plant has modulated (e.g. decreased) alkaloid content and/or modulated content of a tobacco specific nitrosamine (TSNA) or a precursor of a TSNA relative to a comparable plant which does not carry said heritable mutation.

In one aspect, there is provided a mutant of a plant carrying a heritable mutation in a nucleotide sequence of at least one gene encoding an armadillo repeat protein, preferably wherein the gene is selected from: SEQ ID No. 2 or 3; or a functional variant or functional fragment or orthologue thereof; or a nucleic acid sequence which has at least 80% identity to SEQ ID No. 2 or 3; wherein said heritable mutation modulates (e.g. decreases) the expression of the at least one gene encoding an armadillo repeat protein or modifies the nucleic acid sequence of at least one gene encoding an armadillo repeat protein; and wherein the mutant plant has modulated (e.g. decreased) alkaloid content and/or modulated content of a tobacco specific nitrosamine (TSNA) or a precursor of a TSNA relative to a comparable plant which does not carry said heritable mutation.

In a further aspect, there is provided progeny or seed of a mutant plant which carries the heritable mutation according to the present invention.

In a further aspect, the present invention provides a harvested leaf, a processed leaf or cured tobacco material produced from a plant comprising a modification in a nucleotide sequence which:
  a) comprises an amino acid sequence as set out in: SEQ ID No. 1 or a functional variant or functional fragment or orthologue thereof, or a sequence which has at least 80% identity to SEQ ID No. 1; or
  b) is encoded by a nucleotide sequence as set out in SEQ ID No. 2 or 3; or a functional variant or functional fragment or orthologue of SEQ ID No. 2 or 3; or a nucleic acid sequence which has at least 80% identity to SEQ ID No. 2 or 3;
  wherein said modification modulates (e.g. decreases) the expression of the at least one gene encoding an armadillo repeat protein and wherein said plant has modulated (e.g. decreased) alkaloid content and/or modulated content of a tobacco specific nitrosamine (TSNA) or a precursor of a TSNA relative to a comparable plant which does not carry said modification in the at least one gene encoding an armadillo repeat protein.

In one aspect, there is provided a harvested leaf, a processed leaf or cured tobacco material produced from a plant comprising a modification in a nucleotide sequence of at least one gene encoding an armadillo repeat protein, wherein the at least one gene is selected from SEQ ID No. 2 or 3; or a functional variant or functional fragment or orthologue thereof; or a nucleic acid sequence which has at least 80% identity to SEQ ID No. 2 or 3; wherein said modification modulates (e.g. decreases) the expression of the at least one gene encoding an armadillo repeat protein or modifies the nucleic acid sequence of at least one gene encoding an armadillo repeat protein; and wherein said plant has modulated (e.g. decreased) alkaloid content and/or modulated content of a tobacco specific nitrosamine (TSNA) or a precursor of a TSNA relative to a comparable plant which does not carry said modification in the at least one gene encoding an armadillo repeat protein.

In a furtherer aspect, there is provided a method, a leaf, a plant, a plant propagation material, a harvested leaf, a processed tobacco, a tobacco product, a use or a combination thereof as described herein with reference to the description and drawings.

BRIEF DESCRIPTION OF THE DRAWINGS

Embodiments of the invention will now be described, by way of example only, with reference to the accompanying drawings, in which:

FIG. 7 shows the alkaloid content of adult greenhouse-grown TN90 plants silenced for Nitab4.5_0002810g0020.2. Alkaloid content is represented relative to control and comprises three measurements of 20 plants/genotype analysed by one-way ANOVA and Tukey's multiple-comparison post-test. Values are shown as means±SEM. Asterisks indicate statistical significance of P value ≤0.001.

FIG. 8 shows the amino acid sequence of Nitab4.5_0002810g0020.2—SEQ ID No. 1—an armadillo repeat protein from *Nicotiana tabacum* according to the present invention.

FIG. 9 shows the genomic sequence of Nitab4.5_0002810g0020.2—SEQ ID No. 2—encoding an armadillo repeat protein from *Nicotiana tabacum* according to the present invention.

FIG. 10 shows the transcript sequence of Nitab4.5_0002810g0020.2—SEQ ID No. 3—encoding an armadillo repeat protein from *Nicotiana tabacum* according to the present invention.

FIG. 11 shows the miRNA sequence used in FIG. 5.

SEQUENCE LISTING

A summary of sequence identifiers used throughout the subject specification and the corresponding sequence listing is provided wherein:
    SEQ ID No. 1 corresponds to the amino acid sequence of Nitab4.5_0002810g0020.2.

SEQ ID No. 2 corresponds to the genomic sequence of Nitab4.5_0002810g0020.2.

SEQ ID No. 3 corresponds to the transcript sequence of Nitab4.5_0002810g0020.2.

SEQ ID No. 4 is sequence TRV1 used in Example 2.

SEQ ID No. 5 is sequence TRV2 used in Example 2.

Figure 5:
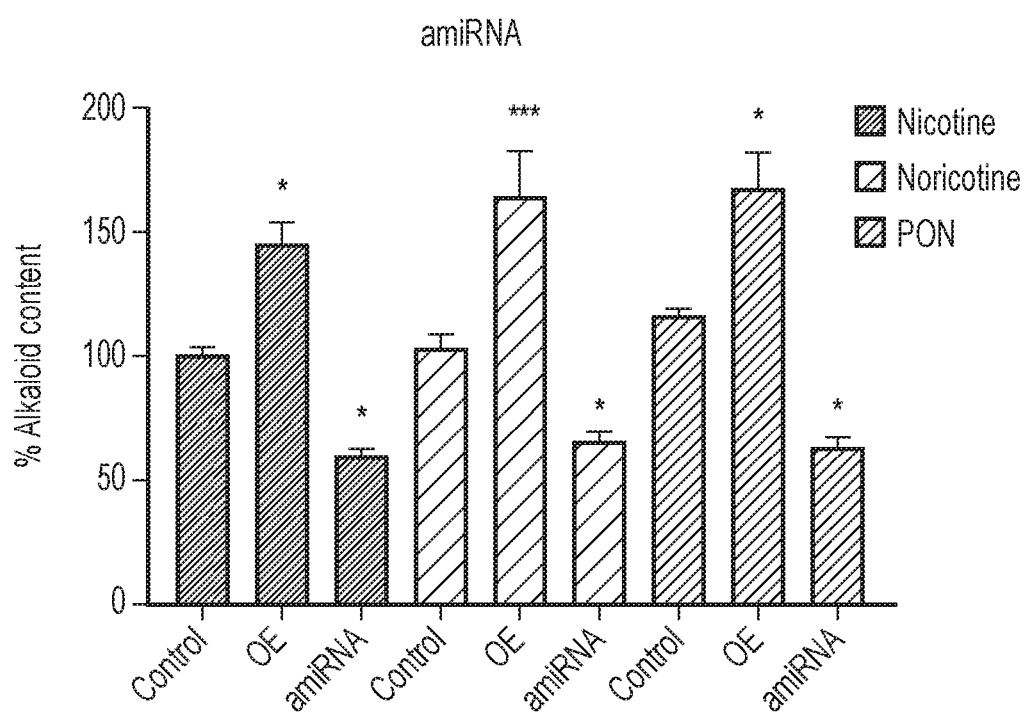
FIG. 5 shows the alkaloid content of 5-week-old TN90 leaves expressing the following constructs: OE=over expressing Nitab4.5_0002810g0020.2; amiRNA=the amiRNA sequence set forth in SEQ ID No. 6. Alkaloid content is represented relative to control and comprises three biological replicates analysed by one-way ANOVA and Tukey's multiple-comparison post-test. Values are shown as means±SEM. Asterisks indicate statistical significance of P value ≤0.001.

SEQ ID No. 6 is the amiRNA sequence used in FIG. 5.

Some sequences disclosed herein contain "X" or "N" in nucleotide sequences. "X" or "N" can be any nucleotide or a deletion or insertion of one or more nucleotides. For example, in some cases a string of "X"s or "N"s are shown. The number of "X"s or "N"s does not necessarily correlate with the actual number of nucleotides at that position. There may be more or fewer nucleotides than shown as "X" or "N" in the sequence.

DETAILED DESCRIPTION

For the first time the present inventors have shown that by modulating the expression of at least one gene encoding an armadillo repeat protein or by modifying the nucleic acid sequence of at least one gene encoding an armadillo repeat protein in a plant (e.g. a tobacco plant), the alkaloid and/or TSNA content of the plant can be modulated.

The present invention provides a method of modulating (e.g. decreasing) the alkaloid content of a plant or a part thereof, the method comprising modifying said plant by modulating (e.g. increasing) the expression of at least one gene encoding an armadillo repeat protein or by modifying the nucleic acid sequence of at least one gene encoding an armadillo repeat protein.

Also provided is a method of modulating (e.g. decreasing) the content of a tobacco specific nitrosamine (TSNA) or a precursor of a TSNA in a tobacco plant or plant part thereof, the method comprising modifying said plant by modulating (e.g. increasing) the expression of at least one gene encoding an armadillo repeat protein or by modifying the nucleic acid sequence of at least one gene encoding an armadillo repeat protein.

The at least one gene encoding an armadillo repeat protein may be selected from at least one gene encoding an armadillo repeat protein which comprises an amino acid sequence as set out in SEQ ID No. 1 or a functional variant or functional fragment or orthologue thereof, or a sequence which has at least 80% identity to SEQ ID No. 1; or wherein the at least one gene encoding an armadillo repeat protein comprises a nucleotide sequence as set out in SEQ ID No. 2 or 3 or a functional variant or functional fragment or orthologue of SEQ ID No. 2 or 3 or a nucleic acid sequence which has at least 80% identity to SEQ ID No. 2 or 3. Suitably, the armadillo repeat protein may comprise an armadillo repeat domain.

In one aspect, the at least one armadillo repeat protein gene encodes a polypeptide which comprises an amino acid sequence as set out in: SEQ ID No. 1 or a functional variant or functional fragment or orthologue thereof, or a sequence which has at least 80% identity to SEQ ID No. 1; or wherein the at least one gene encoding an armadillo repeat protein comprises a nucleotide sequence as set out in SEQ ID No. 2, or 3 or a functional variant or functional fragment or orthologue of SEQ ID No. 2 or 3; or a nucleic acid sequence which has at least 80% identity to SEQ ID No. 2 or 3. Suitably, the armadillo repeat protein may comprise an armadillo repeat domain.

The "expression" of gene encoding an armadillo repeat protein may refer to the level of transcription, translation i.e. protein expression.

Measurement of the level or amount of a gene product may be carried out by any suitable method, for example including comparison of mRNA transcript levels, protein or peptide levels, and/or phenotype of a plant, between a modified plant and comparable plant which has not been modified according to the present invention.

The term "a comparable product" as defined herein would be one derived from a plant (e.g. a tobacco plant) which had not been modified according to the present invention, but in which all other relevant features were the same (e.g. plant species, growing conditions, method of processing the plant, e.g. tobacco, etc.). The comparable product according to the present invention may mean a plant (e.g. a tobacco plant) or a part thereof, such as a leaf (e.g. a tobacco leaf), a harvested leaf (e.g. a harvested tobacco leaf), a cut harvested leaf (e.g. a cut harvested tobacco leaf), a processed leaf (e.g. a processed tobacco leaf) or plant propagation material (e.g. tobacco plant propagation material), or a product comprising said plant or part therefore, e.g. a tobacco product or combinations thereof obtainable (e.g. obtained) or obtained from a plant which has not been modified in accordance with the present invention, e.g. to modulate the expression of gene encoding an armadillo repeat protein or to modify the nucleic acid sequence of at least one gene encoding an armadillo repeat protein. In one embodiment a comparable product is one which does not comprise gene encoding an armadillo repeat protein whose expression has been modulated. In one embodiment, a comparable product is one which does not comprise a modified nucleic acid sequence which encodes at least one gene encoding an armadillo repeat protein The term "modifying" or "modified" as used herein means a plant (e.g. a tobacco plant) or nucleic acid sequence that has been altered or changed. The present invention comprises the modification of plants using techniques for genetic modification of plants or non-genetic modification of plants. Such methods are well known in the art and examples of genetic modification techniques include transformation, transgenics, cisgenics, and gene editing methods. Examples of non-genetic modification techniques include fast-neutron mutagenesis, chemical mutagenesis e.g. ethyl methanesulfonate (EMS) mutagenesis and modern population analysis approaches.

The term "unmodified plant" as defined herein would be a plant (e.g. a tobacco plant) which had not been modified according to the present invention, e.g. to modulate the expression of an armadillo repeat protein or to modify the nucleic acid sequence of at least one gene encoding an armadillo repeat protein; and in which all other relevant features were the same (e.g. plant species, growing conditions, method of processing tobacco, etc.). In one embodiment an unmodified plant is one which does not comprise gene encoding an armadillo repeat protein whose expression has been modulated. In one embodiment, an unmodified plant is one which does not comprise a modified nucleic acid sequence which encodes at least one gene encoding an armadillo repeat protein Armadillo Repeat Protein An "armadillo repeat protein" as used herein has its usual meaning in the art and refers to a protein which comprises armadillo repeats which are repetitive amino sequences of approximately 40 residues in length. Tandem armadillo repeats usually fold together to form an armadillo (ARM) domain.

The armadillo repeat protein comprises an armadillo repeat domain. In one embodiment, an armadillo repeat domain is sequence which corresponds to amino acid 118 to 162 of SEQ ID No. 1 on alignment (e.g. gap alignment) with SEQ ID No. 1.

Armadillo repeat proteins exert functions through interactions of their tandem armadillo repeats domain with a range of diverse binding partners. Armadillo repeat proteins have roles as cell-contact and cytoskeletal-associated proteins and signalling functions by generating and transducing signals affecting gene expression.

The three dimensional fold of an armadillo repeat is known from the crystal structure of β-catenin. The cylindrical structure of the protein comprises a positively charged grove which is thought to interact with the acidic surfaces of interaction partners of β-catenin (Huber et al., Cell. 1997 Sep. 5; 90(5):871-82).

A "gene encoding an armadillo repeat protein" as used herein refers to a gene which encodes an armadillo repeat protein.

In one embodiment an armadillo repeat protein comprises an amino acid sequence shown as SEQ ID No. 1 or a sequence which has at least 80% (such as at least 85%, at least 90%, at least 93%, at least 94%, at least 95%, at least 97%, at least 98%, at least 99%) identity to SEQ ID No. 1, or a homologue thereof. Suitably, the armadillo repeat protein may comprise an armadillo repeat domain such as a domain which corresponds to amino acid 118 to 162 of SEQ ID No. 1 on alignment (e.g. gap alignment) with SEQ ID No. 1.

In one embodiment the armadillo repeat protein according to the present invention comprises or consists of an amino acid sequence set forth in SEQ ID No. 1.

Suitably, the protein may be from *Nicotiana tabacum*.

In one embodiment the armadillo protein is encoded by a polynucleotide sequence wherein the gene (prior to mutation) comprises the sequence shown as SEQ ID No. 2 or 3; or a sequence which has at least 80% sequence identity thereto. Suitably, the armadillo repeat protein may comprise an armadillo repeat domain such as a domain which corresponds to amino acid 118 to 162 of SEQ ID No. 1 on alignment (e.g. gap alignment) with SEQ ID No. 1.

Suitably, the armadillo protein for use according to the present invention may be encoded by a polynucleotide sequence wherein the gene (prior to mutation) comprises the sequence shown as SEQ ID No. 2, or a sequence which has at least 80% sequence identity thereto (preferably at least 85%, preferably at least 90%, preferably at least 93%, preferably at least 94%, preferably at least 95%, at least 97%, or at least 99% identity thereto). Suitably, the armadillo repeat protein may comprise an armadillo repeat domain such as a domain which corresponds to amino acid 118 to 162 of SEQ ID No. 1 on alignment (e.g. gap alignment) with SEQ ID No. 1.

Suitably, the armadillo protein for use according to the present invention may be encoded by a polynucleotide sequence wherein the gene (prior to mutation) comprises the sequence shown as SEQ ID No. 3, or a sequence which has at least 80% sequence identity thereto (preferably at least 85%, preferably at least 90%, preferably at least 93%, preferably at least 94%, preferably at least 95%, at least 97%, or at least 99% identity thereto). Suitably, the armadillo repeat protein may comprise an armadillo repeat domain such as a domain which corresponds to amino acid 118 to 162 of SEQ ID No. 1 on alignment (e.g. gap alignment) with SEQ ID No. 1.

In one embodiment the armadillo protein is encoded by a polynucleotide sequence wherein the gene (prior to mutation) is selected from: SEQ ID No. 2 or 3.

Suitably, the wild type protein for use according to the present invention may be encoded by a polynucleotide sequence from *Nicotiana tabacum*.

In one aspect the present invention provides a method of decreasing the alkaloid content of a plant or part thereof or cell (e.g. plant cell), the method comprising modifying said plant by decreasing or inhibiting the expression of at least one armadillo repeat protein as defined herein.

In one aspect the present invention provides a method of decreasing the alkaloid content of a plant or part thereof or cell (e.g. plant cell), the method comprising modifying said plant by decreasing or inhibiting the expression of at least one gene encoding an armadillo repeat protein as defined herein.

In one aspect the present invention provides a method of decreasing the alkaloid content of a plant or part thereof or plant cell, the method comprising modifying said plant by decreasing or inhibiting the expression of at least one armadillo repeat protein: comprises the amino acid sequence shown as SEQ ID No. 1, or a sequence which has at least 80% identity thereto or a functional variant or functional fragment or orthologue of SEQ ID No. 1; or is encoded by a nucleotide sequence as set out in SEQ ID No. 2 or 3, or a functional variant or functional fragment or orthologue of SEQ ID No. 2 or 3, or a nucleic acid sequence which has at least 80% identity to SEQ ID No. 2 or 3. Suitably, the armadillo repeat protein may comprise an armadillo repeat domain.

In one aspect the present invention provides a method of decreasing the content of a tobacco specific nitrosamine (TSNA) or a precursor of a TSNA a plant or part thereof (e.g. leaf), the method comprising modifying said plant by decreasing or inhibiting the expression of at least one armadillo repeat protein as defined herein.

In one aspect the present invention provides a method of decreasing the content of a tobacco specific nitrosamine (TSNA) or a precursor of a TSNA a plant or part thereof (e.g. leaf), the method comprising modifying said plant by decreasing or inhibiting the expression of at least one gene encoding an armadillo repeat protein as defined herein.

In one aspect the present invention provides a method of decreasing the content of a tobacco specific nitrosamine (TSNA) or a precursor of a TSNA a plant or part thereof (e.g. leaf), the method comprising modifying said plant by decreasing or inhibiting the expression of at least one armadillo repeat protein which:
  a) comprises an amino acid sequence as set out in: SEQ ID No. 1 or a functional variant or functional fragment or orthologue thereof, or a sequence which has at least 80% identity to SEQ ID No. 1; or
  b) is encoded by a nucleotide sequence as set out in SEQ ID No. 2 or 3; or a functional variant or functional fragment or orthologue of SEQ ID No. 2 or 3; or a nucleic acid sequence which has at least 80% identity to SEQ ID No. 2 or 3.

The term "inhibiting" (e.g. inhibiting the expression of gene encoding an armadillo repeat protein) as used herein means that the expression of the gene encoding the armadillo repeat protein is lower or decreased compared with the gene expression of the gene in a comparable product.

The expression of specific genes encoding armadillo repeat proteins can be measured by measuring transcription and/or translation of the gene. Methods for measuring transcription are well known in the art and include, amongst others, northern blot, RNA-Seq, in situ hybridization, DNA microarrays and RT-PCR. Alternatively, the expression of a gene may be measured indirectly by measuring the level of the gene product for example the protein encoded by said gene.

In some embodiments the expression of gene encoding an armadillo repeat protein may be modulated (i.e. increased or decreased) by at least about 10% 20% 30%, or 40%, suitably at least about 50%, 60%, 70%, more suitably at least about 80%, 90%, 95% or 100% when compared to the expression of gene encoding an armadillo repeat protein in a plant (e.g. a tobacco plant) which has not been modified in accordance with the present invention.

Suitably, the expression of the armadillo repeat protein gene may be reduced, partly inactivated, inhibited, eliminated, knocked out or lost such that the protein expression or function of the armadillo repeat protein gene is not detectable.

In one aspect, the at least one armadillo repeat protein gene is knocked out. In other words, the armadillo repeat protein gene has been rendered completely inoperative.

Any method known in the art for reducing or preventing the expression of a protein may be used in the methods according to the present invention.

By way of example, the present method may comprise:
providing a mutation in a nucleic acid sequence which encodes a protein comprising the amino acid sequence shown as SEQ ID No. 1, or an amino acid sequence which has at least 80% (such as at least 85%, at least 90%, at least 93%, at least 94%, at least 95%, at least 97%, at least 98%, at least 99%) sequence identity thereto;
providing a mutation in a regulatory region (e.g. a promoter or an enhancer) which contributes to controlling the expression of a protein comprising the amino acid sequence shown as SEQ ID No. 1, or an amino acid sequence which has at least 80% (such as at least 85%, at least 90%, at least 93%, at least 94%, at least 95%, at least 97%, at least 98%, at least 99%) sequence identity thereto;
providing an antisense RNA, siRNA or miRNA which reduces the level of nucleic acid sequence encoding a protein comprising the amino acid sequence shown as SEQ ID No. 1, or an amino acid sequence which has at least 80% (such as at least 85%, at least 90%, at least 93%, at least 94%, at least 95%, at least 97%, at least 98%, at least 99%) sequence identity thereto.

Each of the above approaches results in the reduction or prevention of expression of: a protein comprising the amino acid sequence shown as SEQ ID No. 1; or an amino acid sequence which has at least 80% (such as at least 85%, at least 90%, at least 93%, at least 94%, at least 95%, at least 97%, at least 98%, at least 99%) sequence identity thereto or which comprises a nucleotide sequence as set out in SEQ ID No. 2 or 3 or a functional variant or functional fragment or orthologue of SEQ ID No. 2 or 3 or a nucleic acid sequence which has at least 80% (such as at least 85%, at least 90%, at least 93%, at least 94%, at least 95%, at least 97%, at least 98%, at least 99%) identity to SEQ ID No. 2 or 3.

In one aspect, a regulatory sequence of the armadillo repeat protein may be modified. The regulatory sequence may be, for example a promotor, enhancer or other regulatory signal. Suitably, modification of the regulatory sequence may result in decreased expression of the armadillo repeat protein. For example, modification such as mutation or deletion of a promoter may decrease expression of the armadillo repeat protein.

As used herein, the term "mutation" encompasses a natural genetic variant or an engineered variant. In particular, the term "mutation" refers to a variation in the nucleotide sequence encoding the amino acid sequence or in the amino acid sequence compared to the sequence shown as SEQ ID No 1, or an amino acid sequence which has at least 80% (preferably at least 85%, preferably at least 90%, preferably at least 93%, preferably at least 95%, preferably at least 98%, preferably at least 99%) sequence identity thereto.

In one embodiment the mutation decreases the alkaloid content of a plant. In another embodiment, the mutation decreases the content of at least one TSNA or a precursor of a TSNA in tobacco.

In one embodiment, a method according to the present invention may comprise providing a nucleic acid sequence to a plant or part thereof or plant cell, wherein said nucleic acid results in the reduction or elimination of the expression of at least one gene encoding an armadillo repeat protein.

In one embodiment, a method according to the present invention may comprise providing a nucleic acid sequence to a plant or part thereof or plant cell, wherein said nucleic acid results in the modification of the nucleic acid sequence of at least one gene encoding an armadillo repeat protein.

Suitably said nucleic acid sequence may be introduced to the plant or part thereof or cell. Suitably an endogenous nucleic acid sequence in the plant or part thereof or cell may be modified to encode the polypeptide according to the present invention (e.g. by gene editing). For example, an endogenous nucleotide sequence may be modified to decrease the expression of at least one gene encoding an armadillo repeat protein.

In a preferred embodiment, each copy of a nucleic acid sequence encoding a protein comprising a sequence shown as SEQ ID No. 1, or a sequence which has at least 80% (such as at least 85%, at least 90%, at least 93%, at least 94%, at least 95%, at least 97%, at least 98%, at least 99%) sequence identity thereto or wherein the at least one gene encoding an armadillo repeat protein comprises a nucleotide sequence as set out in SEQ ID No. 2 or 3, or a functional variant or functional fragment or orthologue of SEQ ID No. 2 or 3 or a nucleic acid sequence which has at least 80% (such as at least 85%, at least 90%, at least 93%, at least 94%, at least 95%, at least 97%, at least 98%, at least 99%) identity to SEQ ID No. 2 or 3 which is present in the plant is modified e.g. mutated as defined herein (e.g. each genomic copy of a gene encoding said protein in a plant is mutated). For example, each copy of the gene in the allotetraploid genome of N. tabacum may be mutated.

In a preferred embodiment the plant or plant cell according to the present invention is homozygous. Suitably, the plant or plant cell may be homozygous for the modification e.g. inhibition or mutation.

In one embodiment, the plant or plant cell according to the present invention expresses only the modified e.g. mutated nucleic acid encoding the armadillo repeat protein. In other words, in some embodiments no endogenous (or endogenous and functional protein) is present in the plant according to the present invention. In other words, if any endogenous protein is present it is preferably in an inactive form.

In one embodiment the present method may comprise providing a mutation in the nucleic acid sequence shown as SEQ ID No. 2 or 3, or a nucleic acid sequence which has at least 80% (such as at least 85%, at least 90%, at least 93%, at least 94%, at least 95%, at least 97%, at least 98%, at least 99%) identity thereto.

The mutation may alter the plant genome such that a nucleic acid sequence encoding a protein comprising the amino acid sequence shown as SEQ ID No. 1, or an amino acid sequence which has at least 80% (such as at least 85%, at least 90%, at least 93%, at least 94%, at least 95%, at least 97%, at least 98%, at least 99%) sequence identity thereto is completely or partially deleted or otherwise modified to prevent the armadillo repeat protein from forming protein: protein interactions.

The mutation may interrupt the nucleic acid sequence which encodes a protein comprising the amino acid sequence shown as SEQ ID No. 1, or an amino acid sequence which has at least 80% (such as at least 85%, at least 90%, at least 93%, at least 94%, at least 95%, at least 97%, at least 98%, at least 99%) sequence identity thereto.

The interruption may cause the nucleic acid sequence to not be transcribed and/or translated.

The nucleic acid sequence may be interrupted, for example, by deleting or otherwise modifying the ATG start codon of the nucleic acid sequence such that translation of the protein is reduced or prevented.

The nucleic acid sequence may comprise one or more nucleotide change(s) that reduce or prevent expression of the protein or affect protein trafficking. For example, expression of the protein may be reduced or prevented by introduction of one or more pre-mature stop codons, a frame shift, a splice mutant or a non-tolerated amino acid substitution in the open reading frame.

A premature stop codon refers to a mutation which introduces a stop codon into the open reading frame and prevents translation of the entire amino acid sequence. The premature stop codon may be a TAG ("amber"), TAA ("ochre"), or TGA ("opal" or "umber") codon.

A frame-shift mutation (also called a framing error or a reading frame shift) is a mutation caused by indels (insertions or deletions) of a number of nucleotides in a nucleic acid sequence that is not divisible by three. Due to the triplet nature of gene expression by codons, the insertion or deletion can change the reading frame, resulting in a completely different translation from the original. A frameshift mutation will often cause the reading of the codons after the mutation to code for different amino acids. The frameshift mutation will commonly result in the introduction of a premature stop codon.

A splice mutant inserts, deletes or changes a number of nucleotides in the specific site at which splicing takes place during the processing of precursor messenger RNA into mature messenger RNA. The deletion of the splicing site results in one or more introns remaining in mature mRNA and may lead to the production of abnormal proteins.

A non-tolerated amino acid substitution refers to a mutation which causes a non-synonymous amino acid substitution in the protein which results in reduced or ablated function of the protein.

Any method known in the art for providing a mutation in a nucleic acid sequence may be used in the method according to the present invention. For example, homologous recombination may be used, in which a vector is created in which the relevant nucleic acid sequence(s) are mutated and used to transform plants or plant cells. Recombinant plants or plant cells expressing the mutated sequence may then be selected.

In one embodiment the mutation introduces a non-tolerated amino acid substitution in a protein comprising an amino acid sequence shown as SEQ ID No. 1, or a sequence which has at least 80% (such as at least 85%, at least 90%, at least 93%, at least 94%, at least 95%, at least 97%, at least 98%, at least 99%) sequence identity thereto.

In one embodiment the mutation reduces, inhibits or eliminates the ability of the armadillo repeat protein to form protein-protein interactions in comparison with a protein shown as SEQ ID No. 1, or a sequence which has at least 80% (such as at least 85%, at least 90%, at least 93%, at least 94%, at least 95%, at least 97%, at least 98%, at least 99%) sequence identity thereto.

In one embodiment the mutation does not alter the level or expression of the protein but reduces inhibits or eliminates the ability of the armadillo repeat protein to form protein-protein interactions in comparison with a protein shown as SEQ ID No. 1, or a sequence which has at least 80% (such as at least 85%, at least 90%, at least 93%, at least 94%, at least 95%, at least 97%, at least 98%, at least 99%) sequence identity thereto. Suitably, the mutation may be in the armadillo repeat domain of the armadillo repeat protein. Suitably, the mutation may be in the protein-protein interaction domain of the armadillo repeat protein.

The expression of a protein may be determined by measuring the presence of the protein using an antibody specific for the armadillo repeat protein, for example antibodies specific for an armadillo repeat by western blot. The ability of a modulated or mutated armadillo repeat protein to form protein-protein interactions may be determined for example by performing co-immunoprecipitation experiments using a modulated or mutated armadillo repeat protein and a corresponding unmodified or unmutated armadillo repeat protein. If the modulation or mutation in the armadillo repeat protein reduces, inhibits or eliminates the ability of the armadillo repeat protein to form protein-protein interactions, the co-immunoprecipitation will show that the modulated or mutated armadillo repeat protein will have fewer protein: protein interactions.

In one embodiment, an armadillo repeat protein comprises an armadillo repeat domain.

As used herein the term "armadillo repeat domain" refers to a structurally conserved protein domain of about 40-45 amino acids which is involved in protein-protein interactions.

Armadillo repeat domains may be annotated or predicted by amino acid sequence comparison with known protein structures. For example, armadillo repeat proteins and armadillo repeat protein domains may be identified by sequence alignment against SEQ ID No. 1, wherein the presence of amino acid residues corresponding to those of from about amino acid 118 to about 162 of SEQ ID No. 1 indicate an armadillo repeat domain.

In one embodiment, an armadillo repeat domain is a region of a protein which corresponds to about amino acid 118 to 162 of SEQ ID No. 1.

In one embodiment, an armadillo repeat domain is sequence which corresponds to amino acid 118 to 162 of SEQ ID No. 1 on alignment (e.g. gap alignment) with SEQ ID No. 1.

In one embodiment, the armadillo repeat domain may contain a mutation which modulates the expression of the at least one gene encoding an armadillo repeat protein. In one embodiment, the armadillo repeat domain may contain a mutation which increases the expression of the at least one gene encoding an armadillo repeat protein. In one embodiment, the armadillo repeat protein domain may contain a mutation which decreases the expression of the at least one gene encoding an armadillo repeat protein.

The mutation may be a deletion, a splice mutant or codon encoding a non-tolerated amino acid substitution.

In one embodiment, the armadillo repeat domain may be mutated thereby modifying the ability of the armadillo repeat protein to form protein:protein interactions. In other words, the armadillo repeat domain may be mutated, resulting in a modification of the binding affinity of the armadillo repeat protein. In one embodiment, the mutation may be comprised in a region which corresponds to about amino acid 118-162 of SEQ ID No. 1. In one embodiment, the mutation may be comprised in a region which corresponds to amino acid 118-162 of SEQ ID No. 1.

Suitably the amino acid numbering corresponds to alignment with SEQ ID No. 1 e.g. gap alignment.

In one embodiment, the nucleic acid sequence encoding the armadillo repeat protein may be wholly or partially deleted. The deletion may be continuous, or may comprise a plurality of sections of sequence. The deletion preferably removes a sufficient amount of nucleotide sequence such that the nucleic acid sequence no longer encodes a functional armadillo repeat protein. The deletion may be total, in which case 100% of the coding portion of the nucleic acid sequence is absent, when compared to the corresponding genome of a comparable unmodified plant. The deletion may, for example, remove at least 50, 60, 70, 80 or 90% of the coding portion of the nucleic acid sequence. Suitably, at least part of the protein may be deleted. The deletion may, for example, remove at least 10, 20, 30, 40, 50, 60, 70, 80 or 90% of the coding portion of the protein.

The deletion may remove at least part of the armadillo repeat domain.

The deletion may, for example, remove at least 10, 20, 30, 40, 50, 60, 70, 80 or 90% of the armadillo repeat protein domain.

Suitably, the deletion may remove at least 5 amino acids, at least 10 amino acids, at least 15, at least 20, at least 25, at least 30 amino acids from the armadillo repeat protein domain. Suitably, the deletion may remove at least 5 amino acids, at least 10 amino acids, at least 15, at least 20, at least 25, at least 30 amino acids from the armadillo repeat protein domain, wherein said domain corresponds to about amino acid residue 118 to about amino acid residue 162 of SEQ ID No. 1.

In one embodiment, the deletion may remove at least 100 amino acids, at least 150, at least 200, at least 250, at least 300, at least 350, at least 400, at least 450, at least 500, at least 550 amino acids from the C terminus of the armadillo repeat protein.

Suitably, the mutated protein may be a truncated protein which lacks at least about 100 amino acids, at least about 150, at least about 200, at least about 250, at least about 300, at least about 350, at least about 400, at least about 450, at least about 500, at least about 550 amino acids corresponding to the amino acids from the C-terminal of SEQ ID No. 1 or a sequence which has at least 80% (preferably at least 85%, at least, at least 90%, at least 95%, at least 98%) sequence identity thereto to a truncated protein which lacks at least about 100 amino acids, at least about 150, at least about 200, at least about 250, at least about 300, at least about 350 at least about 400, at least about 450, at least about 500, at least about 550 amino acids corresponding to the amino acids from the C-terminal of SEQ ID No. 1.

Suitably, the mutated protein may be a truncated protein which lacks at least 100 amino acids, at least 150, at least 200, at least 250, at least 300, at least 350 at least about 400, at least about 450, at least about 500, at least about 550 amino acids corresponding to the amino acids from the C-terminal of SEQ ID No. 1 or a sequence which has at least 80% (preferably at least 85%, at least, at least 90%, at least 95%, at least 98%) sequence identity thereto to a truncated protein which lacks at least 100 amino acids, at least 150, at least 200, at least 250, at least 300, at least 350 at least about 400, at least about 450, at least about 500, at least about 550 amino acids corresponding to the amino acids from the C-terminal of SEQ ID No. 1.

Methods for deletion of nucleic acid sequences in plants are known in the art. For example, homologous recombination may be used, in which a vector is created in which the relevant nucleic acid sequence(s) are missing and used to transform plants or plant cells. Recombinant plants or plant cells expressing the new portion of sequence may then be selected.

Plant cells transformed with a vector as described herein may be grown and maintained in accordance with well-known tissue culturing methods such as by culturing the cells in a suitable culture medium supplied with the necessary growth factors such as amino acids, plant hormones, vitamins, etc.

Modification of the nucleic acid sequence may be performed using targeted mutagenesis methods (also referred to as targeted nucleotide exchange (TNE) or oligo-directed mutagenesis (ODM)). Targeted mutagenesis methods include, without limitation, those employing zinc finger nucleases, TALENs (see WO2011/072246 and WO2010/079430), Cas9-like, Cas9/crRNA/tracrRNA, Cas9/gRNA, or other CRISPR systems (see WO 2014/071006 and WO2014/093622), meganucleases (see WO2007/047859 and WO2009/059195), or targeted mutagenesis methods employing mutagenic oligonucleotides, possibly containing chemically modified nucleotides for enhancing mutagenesis with sequence complementarity to the gene, into plant protoplasts (e.g., KeyBase® or TALENs).

Alternatively, mutagenesis systems such as TILLING (Targeting Induced Local Lesions IN Genomics; McCallum et al., 2000, Nat Biotech 18:455, and McCallum et al. 2000, Plant Physiol. 123, 439-442, both incorporated herein by reference) may be used to generate plant lines which comprise a gene encoding a protein having a mutation. TILLING uses traditional chemical mutagenesis (e.g. ethyl methanesulfonate (EMS) mutagenesis, which produces random mutations) followed by high-throughput screening for mutations. Thus, plants, seeds, cells and tissues comprising a gene having the desired mutation may be obtained.

The method may comprise the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such modified plants. Seeds may, for example, be radiated or chemically treated and the plants may be screened for a modified phenotype.

Fast neutron deletion mutagenesis may be used in a reverse genetics sense (i.e. with PCR) to identify plant lines carrying a deletion in the endogenous gene. See for example Ohshima et al. (1998) Virology 213:472-481; Okubara et al. (1994) Genetics 137:867-874; and Quesada et al. (2000) Genetics 154:421-4315 which are incorporated herein by reference.

In another approach, dominant mutants may be used to trigger RNA silencing due to gene inversion and recombination of a duplicated gene locus. See for example Kusaba et al. (2003) Plant Cell 15:1455-1467 (incorporated herein by reference).

Modified plants may be distinguished from non-modified plants, i.e., wild type plants, by molecular methods, such as the mutation(s) present in the DNA, and by the modified phenotypic characteristics. The modified plants may be homozygous or heterozygous for the modification. Preferably modified plants are homozygous for the modification.

In one embodiment the method of reducing or preventing the expression of a protein comprising the amino acid sequence shown as SEQ ID No. 1, or an amino acid sequence which has at least 80% (such as at least 85%, at least 90%, at least 93%, at least 94%, at least 95%, at least 97%, at least 98%, at least 99%) sequence identity thereto does not comprise treating the plant with a chemical (e.g. an agrochemical).

Other ways of reducing or preventing the expression will be apparent to one skilled in the art and include the use of virus-induced gene silencing (VIGs), micro RNA silencing, RNAi, antisense, tDNA insertions, or dominant negative constructs (or antimorphic mutations).

In one embodiment the expression of a protein comprising the amino acid sequence shown as SEQ ID No. 1, or an amino acid sequence which has at least 80% (such as at least 85%, at least 90%, at least 93%, at least 94%, at least 95%, at least 97%, at least 98%, at least 99%) sequence identity thereto may be reduced or eliminated by virus-induced gene silencing.

In one embodiment the expression of a protein comprising the amino acid sequence shown as SEQ ID No. 1, SEQ ID No. 1, or an amino acid sequence which has at least 80% (such as at least 85%, at least 90%, at least 93%, at least 94%, at least 95%, at least 97%, at least 98%, at least 99%) sequence identity thereto may be reduced or eliminated by microRNAs.

In one embodiment the expression of a protein comprising the amino acid sequence shown as SEQ ID No. 1, SEQ ID No. 1, or an amino acid sequence which has at least 80% (such as at least 85%, at least 90%, at least 93%, at least 94%, at least 95%, at least 97%, at least 98%, at least 99%) sequence identity thereto may be reduced or eliminated by RNAi.

In one embodiment the expression of a protein comprising the amino acid sequence shown as SEQ ID No. 1, SEQ ID No. 1, or an amino acid sequence which has at least 80% (such as at least 85%, at least 90%, at least 93%, at least 94%, at least 95%, at least 97%, at least 98%, at least 99%) sequence identity thereto may be reduced or eliminated by antisense suppression.

In one embodiment the expression of a protein comprising the amino acid sequence shown as SEQ ID No. 1, SEQ ID No. 1, or an amino acid sequence which has at least 80% (such as at least 85%, at least 90%, at least 93%, at least 94%, at least 95%, at least 97%, at least 98%, at least 99%) sequence identity thereto may be reduced or eliminated by sense suppression.

In one embodiment the expression of a protein comprising the amino acid sequence shown as SEQ ID No. 1, SEQ ID No. 1, or an amino acid sequence which has at least 80% (such as at least 85%, at least 90%, at least 93%, at least 94%, at least 95%, at least 97%, at least 98%, at least 99%) sequence identity thereto may be reduced or eliminated by tDNA insertions.

In one embodiment the expression of a protein comprising the amino acid sequence shown as SEQ ID No. 1, SEQ ID No. 1, or an amino acid sequence which has at least 80% (such as at least 85%, at least 90%, at least 93%, at least 94%, at least 95%, at least 97%, at least 98%, at least 99%) sequence identity thereto may be reduced or eliminated by dominant negative constructs (or antimorphic mutations).

In one embodiment the expression of a protein comprising the amino acid sequence shown as SEQ ID No. 1, SEQ ID No. 1, or an amino acid sequence which has at least 80% (such as at least 85%, at least 90%, at least 93%, at least 94%, at least 95%, at least 97%, at least 98%, at least 99%) sequence identity thereto may be reduced or eliminated by a targeted mutagenesis based system.

In one embodiment the expression of a protein comprising the amino acid sequence shown as SEQ ID No. 1, SEQ ID No. 1, or an amino acid sequence which has at least 80% (such as at least 85%, at least 90%, at least 93%, at least 94%, at least 95%, at least 97%, at least 98%, at least 99%) sequence identity thereto may be reduced or eliminated by CRISPR based system.

In one embodiment the expression of a protein comprising the amino acid sequence shown as SEQ ID No. 1, or an amino acid sequence which has at least 80% (such as at least 85%, at least 90%, at least 93%, at least 94%, at least 95%, at least 97%, at least 98%, at least 99%) sequence identity thereto may be reduced or eliminated by zinc finger nuclease, TALENs, meganucleases, mutagenic oligonucleotides or TILLING.

In one aspect the present invention provides a method of increasing the alkaloid content of a plant or part thereof or plant cell, the method comprising modifying said plant by increasing the expression of at least one gene encoding an armadillo repeat protein.

In one aspect the present invention provides a method of increasing the alkaloid content of a plant or part thereof or plant cell, the method comprising modifying said plant by increasing the expression of at least one gene encoding an armadillo repeat protein comprising the amino acid sequence shown as SEQ ID No. 1, or an amino acid sequence which has at least 80% (such as at least 85%, at least 90%, at least 93%, at least 94%, at least 95%, at least 97%, at least 98%, at least 99%), or a functional variant or functional fragment or orthologue of an amino acid sequence as set out in SEQ ID No. 1, or wherein the at least one gene encoding an armadillo repeat protein comprises a nucleotide sequence as set out in SEQ ID No. 2 or 3, or a functional variant or functional fragment or orthologue of SEQ ID No. 2 or 3, or a nucleic acid sequence which has at least 80% (such as at least 85%, at least 90%, at least 93%, at least 94%, at least 95%, at least 97%, at least 98%, at least 99%) identity to SEQ ID No. 2 or 3.

In one aspect the present invention provides a method of decreasing the content of a tobacco specific nitrosamine (TSNA) or a precursor of a TSNA a plant or part thereof (e.g. leaf), the method comprising modifying said plant by decreasing the expression of at least one armadillo repeat protein.

In one aspect the present invention provides a method of decreasing the content of a tobacco specific nitrosamine (TSNA) or a precursor of a TSNA a plant or part thereof (e.g. leaf), the method comprising modifying said plant by decreasing the expression of at least one gene encoding an armadillo repeat protein comprising the sequence shown as SEQ ID No. 1, or a sequence which has at least 80% identity to an amino acid sequence as set out in SEQ ID No. 1, or a functional variant or functional fragment or orthologue of SEQ ID No. 1, or wherein the at least one gene encoding an armadillo repeat protein comprises a nucleotide sequence as set out in SEQ ID No. 2 or 3, or a functional variant or functional fragment or orthologue of SEQ ID No. 2 or 3, or a nucleic acid sequence which has at least 80% identity to SEQ ID No. 2 or 3.

The term "increasing" (e.g. increasing the expression of gene encoding an armadillo repeat protein) as used herein means that the expression of the armadillo repeat protein gene is higher compared with the gene expression of the unmodified gene in a comparable product.

In some embodiments a modification which increases the expression of at least one armadillo repeat protein gene and thereby increases alkaloid content and/or TSNA content (or precursor thereof) is selected from the group consisting of:

increasing, promoting or augmenting transcription, translation or expression of the at least one armadillo repeat protein;

increasing synthesis of the polypeptide encoded by at least one armadillo repeat protein; or its release from intracellular stores; or decreasing the rate of degradation of the polypeptide encoded by at least one armadillo repeat protein gene.

Suitably the method may comprise transforming a cell of a plant (e.g. a tobacco plant) with a genetic construct which encodes at least one armadillo repeat protein comprising an amino acid sequence as set out in SEQ ID No. 1, or a functional variant or functional fragment or orthologue thereof, or a sequence which has at least 80% identity to SEQ ID No. 1; or which comprises a nucleotide sequence as set out in SEQ ID No. 2 or 3 or a functional variant or functional fragment or orthologue of SEQ ID No. 2 or 3, or a nucleic acid sequence which has at least 80% identity to SEQ ID No. 2 or 3; or which comprises a nucleotide sequence which encodes a protein which is capable of promoting or augmenting at least one endogenous armadillo repeat protein gene.

It will be appreciated that each of these options would result in an increased activity and expression of the polypeptide encoded by the at least one armadillo repeat protein gene. The method may comprise regenerating the plant from the transformed cell. There is provided use of genetic construct which is capable of increasing the expression of a polypeptide encoded by at least one armadillo repeat protein gene for increasing the alkaloid content (e.g. nicotine content) and or TSNA content (or precursor thereto) in a plant or part there of or cell transformed with the construct.

The genetic construct may encode a polypeptide comprising the amino acid SEQ ID No. 1, or a functional variant or functional fragment or orthologue thereof, or a sequence which has at least 80% identity to SEQ ID No. 1; or which comprises a nucleotide sequence as set out in SEQ ID No. 2 or 3, or a functional variant or functional fragment or orthologue of SEQ ID No. 2 or 3, or a nucleic acid sequence which has at least 80% identity to SEQ ID No. 2 or 3.

In another embodiment, the invention relates to a method of increasing the alkaloid content of a plant or part thereof and/or TSNA content (or precursor thereto) in a plant or plant part thereof, comprising modifying said plant by increasing the activity of at least one gene encoding an armadillo repeat protein.

In one embodiment the activity of at least one gene encoding an armadillo repeat protein may be increased by introducing (or providing) a mutation to at least one gene encoding an armadillo repeat protein.

Suitably, the expression of at least one gene encoding an armadillo repeat protein may be increased by introducing a mutation to:

a) at least one gene encoding an armadillo repeat protein which comprises an amino acid sequence as set out in SEQ ID No. 1; or a functional variant or functional fragment or orthologue thereof, or a sequence which has at least 80% identity to SEQ ID No. 1; or b) a nucleotide sequence as set out in SEQ ID No. 2 or 3, or a functional variant or functional fragment or orthologue of SEQ ID No. 2 or 3, or a nucleic acid sequence which has at least 80% identity to SEQ ID No. 2 or 3.

In one embodiment, the armadillo repeat protein for use according to the present invention exhibits increased activity compared to an unmodified armadillo repeat protein. The armadillo repeat protein for use according to the present invention may exhibit at least about 1%, at least about 3%, at least about 5%, at least about 10%, at least about 20%, at least about 30%, at least about 40%, at least about 50%, at least about 60%, at least about 70%, at least about 80% or at least about 90% increased binding compared to an unmodified armadillo repeat protein.

Alkaloid Content

In one embodiment the present invention provides a method of modulating the alkaloid content of a plant (e.g. a tobacco plant) or a part thereof, the method comprising modifying said plant by modulating the expression of at least one armadillo repeat protein.

In one embodiment the present invention provides a method of modulating the alkaloid content of a plant (e.g. a tobacco plant) or a part thereof, the method comprising modifying the nucleic acid sequence of at least one gene encoding an armadillo repeat protein.

The term "modulating" is used herein to mean either increasing or decreasing.

The term "increasing alkaloid content" is used herein to mean that the concentration and/or total alkaloid content in the product of the present invention (e.g. plant, part thereof (e.g. leaf), processed leaf or a product made from the plant (e.g. a tobacco product)) is higher compared with a comparable product which has not been modified in accordance with the present invention.

The term "decreasing alkaloid content" is used herein to mean that the concentration and/or total alkaloid content in the product of the present invention (e.g. plant, part thereof (e.g. leaf), processed leaf or a product made from the plant (e.g. a tobacco product)) is lower compared with a comparable product which has not be modified in accordance with the present invention.

In some embodiments, the modulation of alkaloid content refers to an increase in alkaloid content wherein the expression of at least one armadillo repeat protein gene is decreased (or inhibited).

In some embodiments, the modulation of alkaloid content refers to an increase in alkaloid content wherein the nucleic acid sequence of at least one gene encoding an armadillo repeat protein has been modified.

In some embodiments, the modulation of alkaloid content refers to a decrease in alkaloid content wherein the expression of at least one armadillo repeat protein is decreased or inhibited or eliminated. In some embodiments, the modulation of alkaloid content refers to a decrease in alkaloid content wherein the expression of at least one gene encoding an armadillo repeat protein is decreased or inhibited or eliminated.

In some embodiments, the modulation of alkaloid content refers to a decrease in alkaloid content wherein the nucleic acid sequence of at least one gene encoding an armadillo repeat protein has been modified.

In a further aspect, the alkaloid content is measured from leaves. In one aspect the alkaloid content is measured from green leaves. In a further aspect, the alkaloid content is measured from cured leaves, e.g. air-cured, flue-cured, fire-cured or sun-cured leaves. In a further aspect, the alkaloid content is measured from flue-cured leaves. In a further aspect, the alkaloid content is measured from air-cured leaves.

The term "alkaloid content" is used herein to mean the concentration and/or total amount of the entire group of compounds classified as alkaloids. Alkaloids typically present in tobacco include nicotine, nornicotine, PON, anatabine, anabasine and myosmine. In one embodiment the content of one or more alkaloids selected from nicotine, nornicotine, PON, anatabine, anabasine and myosmine is modulated. In one embodiment the content of one or more alkaloids selected from nicotine, nornicotine, PON, anatabine, anabasine and myosmine is reduced. In one embodiment the content of one or more alkaloids selected from nicotine, nornicotine, PON, anatabine, anabasine and myosmine is increased. Suitably nicotine content may be modulated.

In one embodiment, the nicotine content is reduced. In another embodiment, the nicotine content is increased.

Any method known in the art for determining the concentration and/or total content of alkaloids may be used. One preferred method for analysing alkaloid content involves the analysis by gas chromatography-flame ionization detection method (GC-FID).

In one embodiment there is provided a method for producing a plant (e.g. a tobacco plant) or part thereof, a plant propagation material (e.g. a tobacco plant propagation material), a cell (e.g. a tobacco cell), a leaf (e.g. a tobacco leaf), a harvested leaf (e.g. a harvested tobacco leaf), a cut harvested leaf (e.g. a cut harvested tobacco leaf), a processed leaf (e.g. a processed tobacco leaf), a cut and processed leaf (e.g. a cut and processed tobacco leaf), a product comprising said plant or part thereof (e.g. a tobacco product) or combinations thereof obtainable (e.g. obtained) or obtained by a plant of the invention which has modulated alkaloid content, the method comprising: modifying said plant to modulate the expression of gene encoding an armadillo repeat protein; or modifying the nucleic acid sequence of at least one gene encoding an armadillo repeat protein. The modulated alkaloid content may be determined by comparing the alkaloid content in the plant (e.g. tobacco plant) or part thereof, plant propagation material (e.g. tobacco plant propagation material), a cell (e.g. a tobacco cell), leaf (e.g. tobacco leaf), harvested leaf (e.g. a harvested tobacco leaf), cut harvested leaf (e.g. a cut harvested tobacco leaf), processed leaf (e.g. processed tobacco leaf), cut and processed leaf (e.g. cut and processed tobacco leaf), a product comprising a plant or part thereof of the present invention, e.g. a tobacco product, or combinations thereof with a comparable product.

Suitably the alkaloid content may be modulated in a plant, e.g. a tobacco plant e.g. modified tobacco plant. Suitably the alkaloid content may be modulated in a leaf (e.g. a tobacco leaf e.g. a tobacco leaf from a modified tobacco plant). Suitably the alkaloid content may be modulated in a harvested leaf (e.g. a harvested tobacco leaf from a modified tobacco plant). Suitably the alkaloid content may be modulated in a cut harvested leaf (e.g. a cut harvested tobacco leaf from a modified tobacco plant). Suitably the alkaloid content may be modulated in a processed leaf (e.g. a processed tobacco leaf e.g. a processed tobacco leaf from a modified tobacco plant). Suitably the alkaloid content may be modulated in a cut and processed leaf (e.g. a cut and processed tobacco leaf e.g. a cut and processed tobacco leaf from a modified tobacco plant). Suitably the alkaloid content may be modulated in a cured leaf (e.g. cured a tobacco leaf from a modified tobacco plant). Suitably the alkaloid content may be modulated in an extract of a green leaf (e.g. a green tobacco leaf from a modified tobacco plant). Suitably the alkaloid content may be modulated in a product comprising the plant of the present invention or part thereof (e.g. a tobacco product, for example a tobacco product produced from a modified tobacco plant or part thereof). Suitably the alkaloid content may be modulated in any one of the above products or combinations thereof. Suitably the modulation of alkaloid content described above may be an increase in alkaloid content. Suitably the modulation of alkaloid content described above may be a decrease in alkaloid content (e.g. a decrease in nicotine content).

In one embodiment the content of one or more alkaloids selected from nicotine, nornicotine, PON, anatabine, anabasine and myosmine is decreased.

Suitably the modulation of alkaloid content described above may be a decrease in nicotine content. Suitably the modulation of alkaloid content described above may be an increase in nicotine content.

In one embodiment the nicotine content of a modified plant (e.g. tobacco plant), plant propagation material (e.g. tobacco plant propagation material), leaf (e.g. tobacco leaf), harvested leaf (e.g. harvested tobacco leaf), cut harvested leaf (e.g. cut harvested tobacco leaf), processed leaf (e.g. processed tobacco leaf), cut and processed leaf (e.g. cut and processed tobacco leaf) or tobacco product from a modified tobacco plant is decreased.

In one embodiment the alkaloid content of a plant (e.g. tobacco plant) or part thereof may be modulated by at least 2, 3, 4, 5, 6, 7, 8, 9 or 10, fold when compared to the alkaloid content of a plant (e.g. tobacco plant) or part thereof, respectively, which has not been modified to: modulate the expression of at least one gene encoding an armadillo repeat protein; or to modify the nucleic acid sequence of at least one gene encoding an armadillo repeat protein; which has been grown under similar growth conditions. Suitably the alkaloid content may be modulated by about 2 fold to about 10 fold, preferably about 3 fold to about 10 fold, suitably about 3 fold to about 5 fold. Suitably the modification may be an increase or a decrease in alkaloid content. Suitably the modulation may be of one or more alkaloids selected from nicotine, nornicotine, PON, anatabine, anabasine and myosmine. Suitably, the nicotine content is modulated.

In one embodiment of the invention the alkaloid content of a plant (e.g. a tobacco plant) or part thereof may be modulated by 1%, 2%, 5%, 8%, 10%, 12%, 15%, 20%, 25%, 30%, 40%, 50%, 60%, 70%, 80% or 90% in comparison to a plant (e.g. a tobacco plant) or part thereof which has not been modified according to the present invention. The modulation may be an increase or a decrease in alkaloid content when compared to an unmodified plant (e.g. a tobacco plant) or part thereof. Suitably the modulation may be of total alkaloid content. Suitably the modulation may be of one or more alkaloids selected from nicotine, nornicotine, PON, anatabine, anabasine and myosmine. Suitably the modulation is of nicotine content, such as decrease in nicotine content. Suitably the modulation is of nornicotine content, such as decrease in nornicotine content. Suitably the modulation is of PON content, such as decrease in PON content.

Tobacco-Specific Nitrosamine (TSNA) Content

In one embodiment the present invention provides a method of modulating (i.e. increasing or reducing) the content of tobacco-specific nitrosamine (TSNA) or a precursor of a TSNA in a plant (e.g. a tobacco plant) or a part thereof. Suitably, the method may comprise modifying said plant by modulating the expression of at least one armadillo repeat protein. Suitably, the method may comprise modifying said plant by modifying the nucleic acid sequence of at least one gene encoding an armadillo repeat protein. Suitably, the content of TSNA or a precursor of a TSNA may be reduced.

The TSNA may be measured in a processed tobacco, e.g. cured tobacco or reconstituted tobacco. In one embodiment the TSNA content is measured and/or modified (e.g. reduced) in a cured tobacco plant or part thereof (e.g. in cured tobacco leaf).

The term "tobacco-specific nitrosamine" or "TSNA" as used herein has its usual meaning in the art, namely a nitrosamine which is found only in tobacco products or other nicotine-containing products. Suitably the at least one tobacco-specific nitrosamine may be 4-(methylnitrosamino)-1-(3-pyridyl)-1-butanone (NNK), N'-nitrosonornicotine (NNN), N'-nitrosoanatabine (NAT) or N-nitrosoanabasine (NAB).

The term "precursor thereto" when used in relation to at least one tobacco-specific nitrosamine refers to one or more chemicals or compounds of a tobacco plant that give rise to the formation of a tobacco-specific nitrosamine or are involved in the nitrosation reaction leading to tobacco-specific nitrosamine production. Suitably the term "precursor thereto" may refer to nitrate, nitrite or nitric oxide.

The term "modulating" is used herein to mean either increasing or decreasing.

In one embodiment the TSNA is N'nitrosonornicotine (NNN) and/or the precursor is nornicotine.

In one embodiment the TSNA may be one or more of group selected from: N'-nitrosonornicotine (NNN), N'-nitrosoanatabine (NAT), N'-nitrosoanabasine (NAB) and 4-(methyl nitrosamino)-1-(3-pyridyl)-1-butanone (NNK). Suitably the at least one tobacco-specific nitrosamine may be NNK or NNN. In one embodiment the tobacco-specific nitrosamine is NNN.

In one embodiment the precursor of the TSNA is one or more of the group selected from nornicotine, anabasine, anatabine, and an oxidised derivative of nicotine such as pseudooxynicotine (PON).

In a preferred embodiment the precursor of the TSNA is nornicotine.

In one embodiment, the precursor of the TSNA may be PON. The precursor of the TSNA (e.g. NNN, NNK, NAB and/or NAT) may be measured in green tobacco leaf, e.g. prior to processing, e.g. prior to curing. In one embodiment the precursor of the TSNA (e.g. NNN, NNK, NAB and/or NAT) is measured and/or modified (e.g. reduced) in a green tobacco leaf, e.g. prior to processing, e.g. prior to curing.

In one embodiment carrying out a method and or use of the invention results in a reduction of at least one TSNA or a precursor thereto in the modified tobacco plant (or part thereof) when compared to a tobacco plant (or part thereof) which has not been modified in accordance with the present invention.

The terms "reducing at least one TSNA or precursor thereto" or "reduction of at least one TSNA or precursor thereto" are used herein to mean that the concentration and/or total content of the at least one TSNA or precursor thereto in the product, method or use of the invention is lower in relation to a comparable product, method or use. For example, a comparable tobacco industry product would be derived from a tobacco plant which had not been modified according to the present invention, but in which all other relevant features were the same (e.g. plant species, growing conditions, method of processing tobacco, etc.).

Any method known in the art for determining the concentration and/or levels of at least one TSNA or precursor thereto may be used. In particular a method such may comprise the addition of deuterium labelled internal standard, an aqueous extraction and filtration, followed by analysis using reversed phase high performance liquid chromatography with tandem mass spectrometry (LC-MS/MS) may be used. Other examples for determining the concentration and/or level of a precursor to a tobacco-specific nitrosamine include a method such as the one detailed in CORESTA recommended method CRM-72: Determination of Tobacco Specific Nitrosamines in Tobacco and Tobacco Products by LC-MS/MS; CRM being developed into ISO/DIS 21766 or Wagner et al. Analytical Chemistry (2005), 77(4), 1001-1006 all of which are incorporated herein by reference.

Suitably the concentration and/or total content of the at least one tobacco-specific nitrosamine or precursor thereto may be reduced by carrying out a method and/or use of the present invention. Suitably the concentration and/or level of the at least one tobacco-specific nitrosamine or precursor thereto may be reduced in a tobacco plant of the invention (e.g. obtainable (e.g. obtained) or obtained by a method and/or use of the invention) when compared to the concentration and/or level of the at least one tobacco-specific nitrosamine(s) or precursor thereto in a tobacco plant which has not been modified in accordance with present invention.

The concentration and/or total content of the at least one tobacco-specific nitrosamine(s) or precursor thereto may be reduced in a tobacco leaf, harvested leaf, processed tobacco leaf, tobacco industry product or combinations thereof obtainable (e.g. obtained) or obtained from a tobacco plant (or part of a tobacco plant or a tobacco cell culture) of the invention when compared with a tobacco leaf, harvested leaf, processed tobacco leaf, tobacco industry product or combinations thereof obtainable (e.g. obtained) or obtained from a tobacco plant (or part of a tobacco plant or a tobacco cell culture) which has not been modified in accordance with the present invention.

Suitably the concentration and/or total content of the at least one tobacco-specific nitrosamine or precursor thereto may be reduced in a processed tobacco leaf.

Suitably the concentration and/or level of the at least one tobacco-specific nitrosamine or precursor thereto may be reduced in a tobacco industry product.

In one embodiment the at least one tobacco-specific nitrosamine or precursor thereto may be reduced by at least about 1%, at least about 3%, at least about 5%, at least about 10%, at least about 20%, at least about 30%, at least about 40%, at least about 50%, at least about 60%, at least about 70%, at least about 80% or at least about 90%. In some embodiments the at least one tobacco-specific nitrosamine or precursor thereto may be reduced by between about 5% and about 95%, by between about 10% and about 90%, by between 20% and about 80%, by between 30% and about 70%, or by between about 40% and 60%.

In relation to processed (e.g. cured) tobacco leaf (e.g. cured or reconstituted), the at least one tobacco-specific nitrosamine or precursor thereto may be reduced by between about 5000 ng/g and about 50 ng/g, by between about 4000 ng/g and about 100 ng/g, by between about 3000 ng/g and 500 ng/g or by between 2000 ng/g and 1000 ng/g. In some embodiments the at least one tobacco-specific nitrosamine or precursor thereto may be reduced by at least about 5000 ng/g, at least about 4000 ng/g, at least about 3000 ng/g, at least about 2000 ng/g, at least about 1000 ng/g, at least about 500 ng/g, at least about 100 ng/g or at least about 50 ng/g.

Biomass Production

In one aspect, the present invention provides a method of producing a biomass comprising: growing a cell which has been engineered to modulate (e.g. increase) the expression of a gene encoding an armadillo repeat protein as defined herein under conditions to produce a biomass.

In another aspect, the present invention provides a method of producing a biomass comprising: growing a cell which has been engineered to modify the nucleic acid sequence of a gene encoding an armadillo repeat protein as defined herein under conditions to produce a biomass.

In one embodiment, the present invention provides a method of producing a biomass having modified (e.g. increased) concentration and/or total content of nicotine, comprising growing a cell which has been engineered to:
increase the expression of at least armadillo repeat protein comprising an amino acid sequence as set out in SEQ ID No. 1, or a functional variant or functional fragment or orthologue thereof, or a sequence which has at least 80% identity to SEQ ID No. 1; or
increase the expression of a nucleotide sequence as set out in SEQ ID No. 2 or 3, or a functional variant or functional fragment or orthologue of SEQ ID No. 2 or 3 or a nucleic acid sequence which has at least 80% identity to SEQ ID No. 2 or 3.

In one embodiment, the present invention provides a method of producing a biomass having modified (e.g. increased) concentration and/or total content of nicotine, comprising growing a cell which has been engineered to modify:
the nucleic acid sequence of at least one gene encoding an armadillo repeat protein comprising an amino acid sequence as set out in SEQ ID No. 1 or a functional variant or functional fragment or orthologue thereof, or a sequence which has at least 80% identity to SEQ ID No. 1; or
a nucleotide sequence as set out in SEQ ID No. 2 or 3, or a functional variant or functional fragment or orthologue of SEQ ID No. 2 or 3 or a nucleic acid sequence which has at least 80% identity to SEQ ID No. 2 or 3.

Suitably, the armadillo repeat protein comprises an armadillo repeat domain.

Suitably the nucleic acid sequence may comprise a modification (such as a mutation or deletion) in the armadillo repeat domain.

The cell may be engineered by any method known in the art to increase the expression of at least one gene encoding an armadillo repeat protein. Suitably, the cell may be engineered to express an exogenous gene encoding an armadillo repeat protein. Suitably, the cell may be engineered to overexpress a gene encoding an armadillo repeat protein.

Suitably, the biomass may contain a higher concentration and/or total content of nicotine compared with the biomass produced by a comparable cell which has not been modified in accordance with the present invention.

Suitably the cell for use in biomass production may be a plant cell, such as a tobacco cell.

Suitably the cell for use in biomass production may be a yeast cell.

In one embodiment the cell (e.g. yeast cell) may be further modified to comprise one or more sequences that increases nicotinic alkaloid biosynthesis. Suitably these one or more sequences may be incorporated into a nucleic acid construct that is suitable for cell (e.g. yeast cell) transformation. The one or more sequences may be overexpressed in the cell (e.g. yeast cell). The sequences may be selected from one or more of the following genes: MPO (or Methylputrescine Oxidase or MPO1 or MPO2); A622 (or Isoflavone reductase-like protein or Isoflavone reductase homolog or Isoflavone reductase-like protein); BBL (or Berberine bridge enzyme or Berberine bridge enzyme-like or BBE or NBB1); PMT (or Putrescine N-Methyltransferase or putrescine methyltransferase or S-adenosyl-L-methionine:putrescine N-methyltransferase or PMT or PMT1 or PMT2 or PMT3 or PMT4) and QPT (or quinolinate phosphoribosyltransferase). In one embodiment the sequences may be selected from one or more of the following genes: BBL, A622, PMT and MPO (MPO1 or MPO2). Genes suitable for modification of in this way may be taught in US2016032299 for example, which is incorporated herein by reference.

Commercially Desirable Traits

In one embodiment the plants of the present invention have modified (i.e. increased or decreased) total alkaloid content and/or modified (i.e. increased or decreased) content of one or more alkaloids selected from nicotine, nornicotine, anabasine, myosmine and anatabine and/or reduced nicotine, whilst the flavour characteristics and/or other commercially desirable traits are at least maintained. In one embodiment the plants of the present invention produce leaves of a similar grade and/or quality to plants which have not been modified according to the invention.

In one embodiment the plants of the present invention have reduced nicotine content without a significant change in the flavour characteristics of the plant (e.g. compared with the same plant which has not been modified in accordance with the present invention).

In one embodiment the plants of the present invention have modified (i.e. increased or decreased) alkaloid and/or TSNA content without a significant change (e.g. decrease) in other commercially desirable traits of the plant (e.g. compared with the same plant which has not been modified in accordance with the present invention). In particular the yield of the modified plant is preferably not reduced compared with the same plant which has not been modified in accordance with the present invention.

Therefore in one embodiment the methods and uses of the present invention relate to modifying (i.e. increasing or reducing) total alkaloid content and/or modifying (i.e. increasing or reducing) one or more alkaloids selected from nicotine, nornicotine, anabasine and anatabine and/or modifying (i.e. increasing or reducing) nicotine content and/or TSNA content, whilst maintaining the flavour characteristics and/or other commercially desirable traits (e.g. yield).

The term "commercially desirable traits" as used herein will include traits such as yield, mature plant height, harvestable leaf number, average node length, cutter leaf length, cutter leaf width, quality (e.g. leaf quality, suitably cured leaf quality), abiotic (for instance drought) stress tolerance, herbicide tolerance and/or biotic (for instance insect, bacteria or fungus) stress tolerance.

Leaf quality may be measured based on colour, texture and aroma of the cured leaf, for example according to United States Department of Agriculture (USDA) grades and standards.

Tobacco grades are evaluated based on factors including, but not limited to, the leaf stalk position, leaf size, leaf colour, leaf uniformity and integrity, ripeness, texture, elasticity, sheen (related with the intensity and the depth of coloration of the leaf as well as the shine), hygroscopicity (the faculty of the tobacco leaves to absorb and to retain the ambient moisture), and green nuance or cast.

Leaf grade can be determined using standard methods known in the art, for example, using an Official Standard Grade published by the Agricultural Marketing Service of the US Department of Agriculture (7 U.S.C. § 511). See, e.g., Official Standard Grades for Burley Tobacco (U.S. Type 31 and Foreign Type 93), effective Nov. 5, 1990 (55 F.R. 40645);
Official Standard Grades for Flue-Cured Tobacco (U.S. Types 11, 12, 13, 14 and Foreign Type 92), effective Mar. 27, 1989 (54 F.R. 7925); Official Standard Grades for Pennsylvania SeedleafTobacco (U.S. Type 41), effective Jan. 8, 1965 (29 F.R. 16854); Official Standard Grades for Ohio Cigar-Leaf Tobacco (U.S. Types 42, 43, and 44), effective Dec. 8, 1963 (28 F.R. 11719 and 28 F.R. 11926); Official Standard Grades for Wisconsin Cigar-Binder Tobacco (U.S. Types 54 and 55), effective Nov. 20, 1969 (34 F.R. 17061); Official Standard Grades for Wisconsin Cigar-Binder Tobacco (U.S. Types 54 and 55), effective Nov. 20, 1969 (34 F.R. 17061); Official Standard Grades for Georgia and Florida Shade-Grown Cigar-Wrapper Tobacco (U.S. Type 62), Effective April 1971. A USDA grade index value can be determined according to an industry accepted grade index. See, e.g., Bowman et al, Tobacco Science, 32:39-40 (1988); Legacy Tobacco Document Library (Bates Document #523267826-523267833, Jul. 1, 1988, Memorandum on the Proposed Burley Tobacco Grade Index); and Miller et al., 1990, Tobacco Intern., 192:55-57 (all foregoing references are incorporated herein in their entirety).

In one aspect, a USDA grade index is a 0-100 numerical representation of federal grade received and is a weighted average of all stalk positions. A higher grade index indicates higher quality. Alternatively, leaf grade may be determined via hyper-spectral imaging. See e.g., WO 2011/027315 (which is incorporated herein by reference).

In one embodiment, a tobacco plant of the present invention provides tobacco of commercially acceptable grade.

Suitably, the tobacco plant of the present invention provides cured tobacco of commercially acceptable grade.

In one embodiment, a tobacco plant of the present invention is capable of producing leaves having a USDA grade index value of at least about 70% of the USDA grade index value of leaves of a comparable plant when grown in similar growth conditions. Suitably, tobacco plants disclosed herein may be capable of producing leaves having a USDA grade index value of at least about 65%, at least about 70%, at least about 75%, at least about 80%, at least about 85%, at least about 90%, at least about 95%, or at least about 98% of the USDA grade index value of a control plant when grown in similar growth conditions. Suitably, tobacco plants disclosed herein may be capable of producing leaves having a USDA grade index value of between 65% and 130%, between 70% and 130%, between 75% and 130%, between 80% and 130%, between 85% and 130%, between 90% and 130%, between 95% and 130%, between 100% and 130%, between 105% and 130%, between 110% and 130%, between 115% and 130%, or between 120% and 130% of the USDA grade index value of a comparable plant.

In one aspect, the tobacco plant of the present invention is capable of producing leaves having a USDA grade index value of at least 50. Suitably, tobacco plants disclosed herein may be capable of producing leaves having a USDA grade index value of 55 or more, 60 or more, 65 or more, 70 or more, 75 or more, 80 or more, 85 or more, 90 or more, and 95 or more.

Unless specified otherwise, used herein, tobacco yield refers to cured leaf yield which is calculated based on the weight of cured tobacco leaves per acre under standard field conditions following standard agronomic and curing practice.

In one aspect, a plant (e.g. a tobacco plant) of the present invention has a yield between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, between 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the yield of a comparable plant when grown in similar field conditions.

In another aspect, the plant (e.g. a tobacco plant) yield of the present invention is approximately 1.5, 1.6, 1.7, 1.8, 1.9, 2.0, 2.1, 2.2, 2.3, 2.4, 2.5, 2.6, 2.7, 2.8, 2.9, or 3.0 times of the yield of a comparable plant when grown in similar field conditions.

In another aspect, the yield of a tobacco plant of the present invention is comparable to the yield of the flue cured comparable plant when grown in similar field conditions.

In one aspect, a tobacco plant of the present invention provides a yield selected from the group consisting of about between 1200 and 3500, between 1300 and 3400, between 1400 and 3300, between 1500 and 3200, between 1600 and 3100, between 1700 and 3000, between 1800 and 2900, between 1900 and 2800, between 2000 and 2700, between 2100 and 2600, between 2200 and 2500, and between 2300 and 2400 lbs/acre.

In another aspect, a tobacco plant of the present invention provides a yield selected from the group consisting of about between 1200 and 3500, between 1300 and 3500, between 1400 and 3500, between 1500 and 3500, between 1600 and 3500, between 1700 and 3500, between 1800 and 3500, between 1900 and 3500, between 2000 and 3500, between 2100 and 3500, between 2200 and 3500, between 2300 and 3500, between 2400 and 3500, between 2500 and 3500, between 2600 and 3500, between 2700 and 3500, between 2800 and 3500, between 2900 and 3500, between 3000 and 3500, and between 3100 and 3500 lbs/acre.

In a further aspect, a tobacco plant of the present invention provides a yield selected from the group consisting of about between 1200 and 3500, between 1200 and 3400, between 1200 and 3300, between 1200 and 3200, between 1200 and 3100, between 1200 and 3000, between 1200 and 2900, between 1200 and 2800, between 1200 and 2700, between 1200 and 2600, between 1200 and 2500, between 1200 and 2400, between 1200 and 2300, between 1200 and 2200, between 1200 and 2100, between 1200 and 2000, between 1200 and 1900, between 1200 and 1800, between 1200 and 1700, between 1200 and 1600, between 1200 and 1500, and between 1200 and 1400 lbs/acre.

Plant Breeding

In one embodiment the present invention provides a method of producing a plant having a modified alkaloid content and/or modified content of a tobacco specific nitrosamine (TSNA) or a precursor of a TSNA, comprising:

a. crossing a donor plant having modified nicotine content and/or modified content of a tobacco specific nitrosamine (TSNA) or a precursor of a TSNA and wherein the expression of at least one gene encoding an armadillo repeat protein has been modulated in the donor plant in accordance with the present invention with a recipient tobacco plant that does not have modified nicotine content or modified content of a tobacco specific nitrosamine (TSNA) or a precursor of a TSNA and possesses commercially desirable traits;

b. isolating genetic material from a progeny of said donor plant crossed with said recipient plant; and c. performing molecular marker-assisted selection with a molecular marker comprising:

i. identifying an introgressed region comprising a mutation in a polynucleotide sequence encoding a protein defined in a.

In another embodiment the present invention provides a method of producing a plant having a modified alkaloid content and/or modified content of a tobacco specific nitrosamine (TSNA) or a precursor of a TSNA, comprising:

ii. crossing a donor plant having modified nicotine content and/or modified content of a tobacco specific nitrosamine (TSNA) or a precursor of a TSNA; wherein the nucleic acid sequence of at least one gene encoding an armadillo repeat protein has been modified in the donor plant in accordance with the present invention with a recipient tobacco plant that does not have modified nicotine content or modified content of a tobacco specific nitrosamine (TSNA) or a precursor of a TSNA and possesses commercially desirable traits;

iii. isolating genetic material from a progeny of said donor plant crossed with said recipient plant; and iv. performing molecular marker-assisted selection with a molecular marker comprising:

v. identifying an introgressed region comprising a mutation in a polynucleotide sequence encoding a protein defined in a.

vi.

The expression of an armadillo repeat protein which:

a) comprises an amino acid sequence as set out in: SEQ ID No. 1 or a functional variant or functional fragment or orthologue thereof, or a sequence which has at least 80% identity to SEQ ID No. 1; or b) is encoded by a nucleotide sequence as set out in SEQ ID No. 2 or 3; or a functional variant or functional fragment or orthologue of SEQ ID No. 2 or 3; or a nucleic acid sequence which has at least 80% identity to SEQ ID No. 2 or 3;

is modulated in the donor plant when compared to a comparable plant. Suitably, the armadillo repeat protein comprises an armadillo repeat domain.

The molecular marker assisted selection may comprise performing PCR to identify an introgressed nucleic acid sequence comprising a mutation which modulates the expression of a protein comprising the amino acid sequence shown as SEQ ID No. 1 or an amino acid sequence which has at least 80% identity thereto.

Plants

Suitable plants according to the invention include the Solanaceae family of plants which include, for example jimson weed, eggplant, mandrake, deadly nightshade (belladonna), capsicum (paprika, chili pepper), potato and tobacco.

In one embodiment a suitable genus of Solanaceae is *Solanum*, e.g. *Solanum lycopersicum*.

In one embodiment a suitable genus of Solanaceae is *Nicotiana*, e.g. *Nicotiana tabacum* or *Nicotiana rustica*.

A suitable species of *Nicotiana* may be *Nicotiana tabacum*. Species of *Nicotiana* may be referred to herein as a tobacco plant, or simply tobacco.

Tobacco Plants

The present invention provides methods, uses directed to plants (e.g. tobacco plants) as well as a cell (e.g. a tobacco cell), a plant (e.g. a tobacco plant) and a plant propagation material.

The term "tobacco plant" as used herein refers to a plant in the genus *Nicotiana* that is used in the production of tobacco products. Non-limiting examples of suitable "tobacco" plants include *N. tabacum* and *N. rustica* (for example, *N. tabacum* L., LA B21, LN KY171, TI 1406, Basma, Galpao, Perique, Beinhart 1000-1, and Petico).

The tobacco material can be derived or obtained from varieties of *Nicotiana tabacum* types, commonly known as Burley varieties, flue or bright varieties and dark varieties. In some embodiments, the tobacco material is derived from a Burley, Virginia or a dark tobacco plant. The tobacco plant may be selected from Burley tobacco, rare tobacco, specialty tobacco, expanded tobacco or the like.

The use of tobacco cultivars and elite tobacco cultivars is also contemplated herein. The tobacco plant for use herein may therefore be a tobacco variety or elite tobacco cultivar. Particularly useful *Nicotiana tabacum* varieties include Flue-cured Virginia type, Burley type, and Oriental type.

In some embodiments, the tobacco plant may be, for example, selected from one or more of the following varieties: L. cultivar T.I. 1068, AA 37-1, B 13P, Xanthi (Mitchell-Mor), KT D #3 Hybrid 107, Bel-W3, 79-615, Samsun Holmes NN, F4 from cross BU21 x Hoja Parado, line 97, KTRDC #2 Hybrid 49, KTRDC #4 Hybrid 1 10, Burley 21, PM016, KTRDC #5 KY 160 SI, KTRDC #7 FCA, KTRDC #6 TN 86 SI, PM021, K 149, K 326, K 346, K 358, K 394, K 399, K 730, KY 10, KY 14, KY 160, KY 17, KY 8959, KY 9, KY 907, MD 609, McNair 373, NC 2000, PG 01, PG 04, P01, P02, P03, RG 11, RG 17, RG 8, Speight G-28, TN 86, TN 90, VA 509, AS44, Banket A1, Basma Drama B84/31, Basma I Zichna ZP4/B, Basma Xanthi BX 2A, Batek, Besuki Jember, C104, Coker 319, Coker 347, Criollo Misionero, PM092, Delcrest, Djebel 81, DVH 405, Galpao Comum, HBO4P, Hicks Broadleaf, Kabakulak Elassona, PM102, Kutsage E1, KY 14 x L8, KY 171, LA BU 21, McNair 944, NC 2326, NC 71, NC 297, NC 3, PVH 03, PVH 09, PVH 19, PVH 21 10, Red Russian, Samsun, Saplak, Simmaba, Talgar 28, PM132, Wislica, Yayaldag, NC 4, TR Madole, Prilep HC-72, Prilep P23, Prilep PB 156/1, Prilep P12-2/1, Yaka JK-48, Yaka JB 125/3, TI-1068, KDH-960, TI-1070, TW136, PM204, PM205, Basma, TKF 4028, L8, TKF 2002, TN 90, GR141, Basma xanthi, GR149, GR153, and Petit Havana.

Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF91 1, DT 538 LC, Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KTY14xL8 LC, Little Crittenden, McNair 373, McNair 944, msKY 14xL8, Narrow Leaf Madole, Narrow Leaf Madole LC, NBH 98, N-126, N-777LC, N-7371 LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC 'Periq'e' tobacco, PVH03, PVH09, PVH19, PVH50, PVH51, R 610, R 630, R 7-1 1, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, VA359, AA 37-1, B 13P, Xanthi (Mitchell-Mor), Bel-W3, 79-615, Samsun Holmes NN, KTRDC number 2 Hybrid 49, Burley 21, KY 8959, KY 9, MD 609, PG 01, PG 04, P01, P02, P03, RG 1 1, RG 8, VA 509, AS44, Banket A1, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpao Comum, HBO4P, Hicks Broadleaf, Kabakulak Elassona, Kutsage E1, LA BU 21, NC 2326, NC 297, PVH 21 10, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, Basma xanthi, GR149, GR153, Petit Havana. Low converter subvarieties of the above, even if not specifically identified herein, are also contemplated.

The tobacco plant may be a Burley, Flue-cured Virginia, or Oriental.

In one embodiment the plant propagation material may be obtainable (e.g. obtained) from a plant (e.g. a tobacco plant) of the invention.

A "plant propagation material" as used herein refers to any plant matter taken from a plant from which further plants may be produced. Suitably, a plant propagation material may be selected from a seed, plant calli and plant clumps. Suitably the plant propagation material may be a seed. Suitably, the plant propagation material may be plant calli. Suitably the plant propagation material may be plant clumps.

In one embodiment the cell (e.g. tobacco cell), tobacco plant and/or plant propagation material may be obtainable (e.g. obtained) (e.g. obtained) by a method according to the invention.

Suitably a tobacco plant according to the present invention may have modulated (e.g. decreased) nicotine content when compared to an unmodified tobacco plant, wherein the tobacco plant has been modified to modulate (e.g. increase) the expression of at least one armadillo repeat protein which:
  a) comprises an amino acid sequence as set out in: SEQ ID No. 1 or a functional variant or functional fragment or orthologue thereof, or a sequence which has at least 80% identity to SEQ ID No. 1; or
  b) is encoded by a nucleotide sequence as set out in SEQ ID No. 2 or 3; or a functional variant or functional fragment or orthologue of SEQ ID No. 2 or 3; or a nucleic acid sequence which has at least 80% identity to SEQ ID No. 2 or 3.

Suitably a tobacco plant according to the present invention may have modulated (e.g. reduced) content of a tobacco specific nitrosamine (TSNA) or a precursor of a TSNA when compared to an unmodified tobacco plant, wherein the tobacco plant has been modified to modulate (e.g. increase) the expression of at least one armadillo repeat protein which:
  a) comprises an amino acid sequence as set out in: SEQ ID No. 1 or a functional variant or functional fragment or orthologue thereof, or a sequence which has at least 80% identity to SEQ ID No. 1; or
  b) is encoded by a nucleotide sequence as set out in SEQ ID No. 2 or 3; or a functional variant or functional fragment or orthologue of SEQ ID No. 2 or 3; or a nucleic acid sequence which has at least 80% identity to SEQ ID No. 2 or 3.

In one embodiment the tobacco plant in accordance with the present invention comprises a tobacco cell of the invention.

In another embodiment the plant propagation material may be obtainable (e.g. obtained) (e.g. obtained) from a tobacco plant of the invention.

In one embodiment there is provided the use of a tobacco plant as described herein to breed a tobacco plant.

The present invention also provides in another embodiment the use of a tobacco plant of the foregoing embodiments for the production of a tobacco industry product.

In another embodiment there is provided the use of a tobacco plant of the invention to grow a crop.

In one embodiment there is provided the use of a cell as provided for in the foregoing embodiments for production of a tobacco industry product.

In one embodiment the present invention provides a cell culture (e.g. in in vitro culture).

The tobacco cell culture may be a cell suspension culture. These cells cultured in vitro may be incorporated into a tobacco industry product, e.g. as a substitute for conventional tobacco particles, shreds, fine cut or long cut tobacco lamina, as an additive ingredient or as both a substitute and an additive. Suitably, the cell culture may produce nicotine.

In one embodiment there is provided the use of a cell culture, e.g. a harvested and/or processed cell culture according to the present invention for the production of a tobacco industry product.

The tobacco cells harvested from an in vitro culture may be dried, e.g. freeze-dried, for example to produce a powder.

In one embodiment, the cell culture is a tobacco cell culture. The skilled person will be aware of known methods for establishing in vitro cultures of tobacco cells. By way of example only the following method may be used: collecting seeds form a tobacco plant of interest and sterilising their exterior to eliminate unwanted organisms, planting said seeds to grown a tobacco plant of interest, removing tissue from the tobacco plant (for example, from the tobacco stem) for use as an explant, establishing a callus culture form the tobacco explant, establishing a cell suspension culture from the callus culture, and harvesting culture material (e.g. including tobacco cells) to produce a tobacco cell culture.

The tobacco cells can be harvested by various methods, including filtration, e.g. vacuum filtration. The sample may be washed in the filter by adding water and the remaining liquid removed with the filtration, e.g. vacuum filtration.

The harvested tobacco cell culture may be further processed, e.g. dried, such as air-dried and/or freeze-dried. The harvested tobacco cell culture or dried harvested tobacco cell culture or an extract therefrom may be incorporated into tobacco industry products according to the present invention.

In one embodiment, the present invention provides a plant (e.g. tobacco plant) or part thereof for use in molecular farming. Suitably, a plant or part thereof modified in accordance with the present invention may be used in the manufacture of proteins such as therapeutics e.g. antibiotics, virus like particles, neutraceuticals or small molecules.

In one embodiment, the present invention provides a method for the production of proteins (e.g. therapeutic proteins); the method comprising modifying a plant or part thereof capable of producing said protein (e.g. therapeutic protein) by modulating the expression of an armadillo repeat protein which:
  a) comprises an amino acid sequence as set out in: SEQ ID No. 1 or a functional variant or functional fragment or orthologue thereof, or a sequence which has at least 80% identity to SEQ ID No. 1; or b) is encoded by a nucleotide sequence as set out in SEQ ID No. 2 or 3; or a functional variant or functional fragment or orthologue of SEQ ID No. 2 or 3; or a nucleic acid sequence which has at least 80% identity to SEQ ID No. 2 or 3;

and culturing the plant under conditions sufficient to allow the production of said protein (e.g. therapeutic protein). Suitably, the armadillo repeat protein comprises an armadillo repeat domain.

Products

The present invention also provides for products obtainable (e.g. obtained) or obtained from plants according to the present invention. Products are provided which are obtainable (e.g. obtained) or obtained from a plant in which the expression of gene encoding an armadillo repeat protein has been modulated. Products are provided which are obtainable (e.g. obtained) or obtained from a plant in which the nucleic acid sequence of at least one armadillo repeat protein has been modified. Suitably, the nucleic acid sequence encoding an armadillo repeat domain has been modified.

In one embodiment, the product may comprise a construct of the invention which modulates the expression of at least one gene encoding an armadillo repeat protein as defined herein. In one embodiment, the product may comprise a construct of the invention which modifies the nucleic acid sequence of at least one gene encoding an armadillo repeat protein as defined herein.

The present invention also provides for products obtainable (e.g. obtained) or obtained from tobacco according to the present invention.

In one embodiment there is provided the use of a tobacco plant of the invention to produce a tobacco leaf.

Suitably the tobacco leaf may be subjected to downstream applications such as processing.

Thus in one embodiment the use of the foregoing embodiment may provide a processed tobacco leaf. Suitably the tobacco leaf may be subjected to curing, fermenting, pasteurizing or combinations thereof. In another embodiment the tobacco leaf may be cut. In some embodiments the tobacco leaf may be cut before or after being subjected to curing, fermenting, pasteurizing or combinations thereof.

In one embodiment the present invention provides a harvested leaf of a tobacco plant of the invention.

In a further embodiment the harvested leaf may be obtainable (e.g. obtained) (e.g. obtained) from a tobacco plant propagated from a propagation material of the present invention.

In another embodiment there is provided a harvest leaf obtainable (e.g. obtained) from a method or use of the present invention.

Suitably the harvested leaf may be a cut harvested leaf.

In some embodiments the harvested leaf may comprise viable tobacco cells. In other embodiments the harvested leaf may be subjected to further processing.

There is also provided a processed tobacco leaf.

The processed tobacco leaf may be obtainable (e.g. obtained) from a tobacco plant of the invention. Suitably the processed tobacco leaf may be obtainable (e.g. obtained) from a tobacco plant obtained in accordance with any of the methods and/or uses of the present invention.

In another embodiment the processed tobacco leaf may be obtainable (e.g. obtained) from a tobacco plant propagated form a tobacco plant propagation material according to the present invention.

The processed tobacco leaf of the present invention may be obtainable (e.g. obtained) by processing a harvested leaf of the invention.

The term "processed tobacco leaf" as used herein refers to a tobacco leaf that has undergone one or more processing steps to which tobacco is subjected to in the art. A "processed tobacco leaf" comprises no or substantially no viable cells.

The term "viable cells" refers to cells which are able to grow and/or are metabolically active. Thus, if a cell is said to not be viable, also referred to as "non-viable" then a cell does not display the characteristics of a viable cell.

The term "substantially no viable cells" means that less than about 5% of the total cells are viable. Preferably, less than about 3%, more preferably less than about 1%, even more preferably less than about 0.1% of the total cells are viable.

In one embodiment the processed tobacco leaf may be processed by one or more of: curing, fermenting and/or pasteurizing.

Suitably the processed tobacco leaf may be processed by curing.

Tobacco leaf may be cured by any method known in the art. In one embodiment tobacco leaf may be cured by one or more of the curing methods selected from the group consisting of: air curing, fire curing, flue curing and sun curing.

Suitably the tobacco leaf may be air cured.

Typically air curing is achieved by hanging tobacco leaf in well-ventilated barns and allowing to dry. This is usually carried out over a period of four to eight weeks. Air curing is especially suitable for burley tobacco.

Suitably the tobacco leaf may be fire cured. Fire curing is typically achieved by hanging tobacco leaf in large barns where fires of hardwoods are kept on continuous or intermittent low smolder and usually takes between three days and ten weeks, depending on the process and the tobacco.

In another embodiment the tobacco leaf may be flue cured. Flue curing may comprise stringing tobacco leaves onto tobacco sticks and hanging them from tier-poles in curing barns. The barns usually have a flue which runs from externally fed fire boxes. Typically this results in tobacco that has been heat-cured without being exposed to smoke. Usually the temperature will be raised slowly over the course of the curing with the whole process taking approximately 1 week.

Suitably the tobacco leaf may be sun cured. This method typically involves exposure of uncovered tobacco to the sun.

Suitably the processed tobacco leaf may be processed by fermenting.

Fermentation can be carried out in any manner known in the art. Typically during fermentation, the tobacco leaves are piled into stacks (a bulk) of cured tobacco covered in e.g. burlap to retain moisture. The combination of the remaining water inside the leaf and the weight of the tobacco generates a natural heat which ripens the tobacco. The temperature in the centre of the bulk is monitored daily. In some methods every week, the entire bulk is opened. The leaves are then removed to be shaken and moistened and the bulk is rotated so that the inside leaves go outside and the bottom leaves are placed on the top of the bulk. This ensures even fermentation throughout the bulk. The additional moisture on the leaves, plus the actual rotation of the leaves themselves, generates heat, releasing the tobacco's natural ammonia and reducing nicotine, while also deepening the colour and improving the tobacco's aroma. Typically the fermentation process continues for up to 6 months, depending on the variety of tobacco, stalk position on the leaf, thickness and intended use of leaf.

Suitably the processed tobacco leaf may be processed by pasteurizing. Pasteurizing may be particularly preferred when the tobacco leaf will be used to make a smokeless tobacco industry product, most preferably snus.

Tobacco leaf pasteurisation may be carried out by any method known in the art. For example pasteurisation may be carried out as detailed in J Foulds, L Ramstrom, M Burke, K Fagerstrom. Effect of smokeless tobacco (snus) on smoking and public health in Sweden.

Tobacco Control (2003) 12: 349-359, the teaching of which is incorporated herein by reference. During the production of snus pasteurisation is typically carried out by a process in which the tobacco is heat treated with steam for 24-36 hours (reaching temperatures of approximately 100° C.). This results in an almost sterile product and without wishing to be bound by theory one of the consequences of this is believed to be a limitation of further TSNA formation.

In one embodiment the pasteurisation may be steam pasteurisation.

In some embodiments the processed tobacco leaf may be cut. The processed tobacco leaf may be cut before or after processing. Suitably, the processed tobacco leaf may be cut after processing.

In one embodiment, the use of the foregoing embodiment may provide reconstituted tobacco.

In one embodiment, there is provided reconstituted tobacco.

"Reconstituted" as used herein may also be referred to as recon, recycled or homogenized sheet tobacco and refers to tobacco material generated from remnants of tobacco leaf after processing. Reconstituted tobacco allows the production of a consistent, high quality blend and allows the adjustment of the ratio of individual components.

Reconstituted tobacco may be nano fibre recon (nanofibers can be extracted in solid or liquid form), paper making recon (which uses stems, scraps, and midribs, etc. as the raw material) or slurry type recon (which uses a mixture of fines and tobacco stems, ground to power, mixed with water and vegetable binding agent. The soluble residue is formed to sheets by extracting the water.)

Any method known in the art may be used for making reconstituted tobacco, for example see CORESTA Congress, Sapporo, 2012, Smoke Science/Product Technology Groups, SSPT 12 (incorporated herein by reference).

In some embodiments the tobacco plant, harvested leaf of a tobacco plant and/or processed tobacco leaf may be used to extract nicotine. The extraction of nicotine can be achieved using any method known in the art. For example a method for extracting nicotine from tobacco is taught in U.S. Pat. No. 2,162,738 which is incorporated herein by reference.

In one aspect, the present invention provides cured tobacco material made from a tobacco plant or part thereof according to the invention.

In another aspect, the present invention provides a tobacco blend comprising tobacco material made from a tobacco plant or part thereof according to the present invention, or from a tobacco cell culture according to the present invention. In one aspect, the present invention provides a tobacco blend comprising cured tobacco material according to the present invention.

Suitably, the tobacco blend according to the present invention may comprise approximately 10%, 20%, 30%, 40%, 50%, 60%, 70%, 80% or 90% tobacco from a tobacco plant or part thereof according to the present invention, or from a tobacco cell culture according to the present invention. Suitably, the tobacco blend may comprise approximately 10% tobacco from a tobacco plant or part thereof according to the present invention, or from a tobacco cell culture according to the present invention. Suitably, the tobacco blend may comprise approximately 20% tobacco from a tobacco plant or part thereof according to the present invention, or from a tobacco cell culture according to the present invention. Suitably, the tobacco blend may comprise approximately 30% tobacco from a tobacco plant or part thereof according to the present invention, or from a tobacco cell culture according to the present invention. Suitably, the tobacco blend may comprise approximately 40% tobacco from a tobacco plant or part thereof according to the present invention, or from a tobacco cell culture according to the present invention. Suitably, the tobacco blend may comprise approximately 50% tobacco from a tobacco plant or part thereof according to the present invention, or from a tobacco cell culture according to the present invention. Suitably, the tobacco blend may comprise approximately 60% tobacco from a tobacco plant or part thereof according to the present invention, or from a tobacco cell culture according to the present invention. Suitably, the tobacco blend may comprise approximately 70% tobacco from a tobacco plant or part thereof according to the present invention, or from a tobacco cell culture according to the present invention. Suitably, the tobacco blend may comprise approximately 80% tobacco from a tobacco plant or part thereof according to the present invention, or from a tobacco cell culture according to the present invention. Suitably, the tobacco blend may comprise approximately 90% tobacco from a tobacco plant or part thereof according to the present invention, or from a tobacco cell culture according to the present invention.

In one aspect, a tobacco blend product of the present invention comprises at least about 5, 10, 20, 30, 40, 50, 60, 70, 80, 90, or 95 percent by dry weight of tobacco cured from a tobacco plant or part thereof according to the present invention, or a tobacco cell culture according to the present invention.

Suitably, the cured tobacco material may be air cured. Suitably, the cured tobacco material may be flue cured. Suitably, the cured tobacco material may be sun cured. Suitably, the cured tobacco material may be fire cured.

A tobacco industry product or smoking article according to the present invention may comprise the tobacco material (e.g. cured tobacco material or reconstituted tobacco material) according to the present invention.

In another aspect the present invention provides a tobacco industry product.

In one embodiment the tobacco industry product according to the present invention may be a blended tobacco industry product. Suitably, the tobacco blend may comprise cured tobacco material according to the present invention.

In one embodiment the tobacco industry product may be prepared from a tobacco plant of the invention or a part thereof.

Suitably the tobacco plant or part thereof may be propagated from a tobacco plant propagation material according to the present invention.

The term "part thereof" as used herein in the context of a tobacco plant refers to a portion of the tobacco plant. Suitably, the "part thereof" may be a leaf, root or stem of a tobacco plant or the flowers. Suitably, the "part thereof" may be a leaf, root or stem of a tobacco plant.

Tobacco Industry Product

As used herein, the term "tobacco industry product" is intended to include combustible smoking articles such as cigarettes, cigarillos, cigars, tobacco for pipes or for roll-your-own cigarettes, (whether based on tobacco, tobacco derivatives, expanded tobacco, reconstituted tobacco, tobacco substitutes or other smokable material), non-combustible aerosol provision systems such as heating products that release compounds from substrate materials without burning such as electronic cigarettes, tobacco heating products, and hybrid systems to generate aerosol from a combination of substrate materials, for example hybrid systems containing a liquid or gel or solid substrate, as well as aerosolizable substrate materials used within these aerosol provision systems; and aerosol-free delivery articles such as lozenges, gums, patches, articles comprising breathable powders and smokeless tobacco industry products such as snus and snuff, which aerosol-free delivery articles may or may not deliver nicotine.

In one embodiment the tobacco industry product may be prepared from (e.g. may comprise) a tobacco plant of the invention or a part thereof.

Suitably the tobacco plant or part thereof may be propagated from a tobacco plant propagation material according to the present invention.

The term "part thereof" as used herein in the context of a tobacco plant refers to a portion of the tobacco plant. Preferably the "part thereof" is a leaf of a tobacco plant.

In another embodiment the tobacco industry product may be prepared from a harvested leaf of the invention.

In a further embodiment the tobacco industry product may be prepared from a processed tobacco leaf of the invention.

Suitably the tobacco industry product may be prepared from a tobacco leaf processed by one or more of: curing, fermenting and/or pasteurizing.

Suitably the tobacco industry product may comprise a cut tobacco leaf, optionally processed as per the foregoing embodiment.

In another embodiment, the tobacco industry product may be prepared from a tobacco cell culture according to the present invention.

In another embodiment, the tobacco industry product may be prepared from (e.g. may comprise) a cured tobacco material according to the present invention.

In another embodiment, the tobacco industry product may be prepared from (e.g. may comprise) a tobacco blend according to the present invention.

In one embodiment the tobacco industry product may be a smoking article.

As used herein, the term "smoking article" can include smokable products, such as rolling tobacco, cigarettes, cigars and cigarillos whether based on tobacco, tobacco derivatives, expanded tobacco, reconstituted tobacco or tobacco substitutes.

In another embodiment the tobacco industry product may be a smokeless tobacco industry product.

The term "smokeless tobacco industry product" as used herein refers to a tobacco industry product that is not intended to be smoked and/or subjected to combustion.

Smokeless tobacco industry products (including heat-not-burn materials) may contain tobacco in any form, including dried particles, shreds, granules, powders, or slurry, deposited on, mixed in, surrounded by, or combined with other ingredients in any format, such as flakes, films, tabs, foams, or beads.

In one embodiment a smokeless tobacco industry product may include snus, snuff, chewing tobacco or the like.

In one embodiment, the tobacco industry product is a combustible smoking article, selected from the group consisting of a cigarette, a cigarillo and a cigar.

In one embodiment, the tobacco industry product comprises one or more components of a combustible smoking article, such as a filter, a filter rod, a filter rod segments, tobacco, a tobacco rod, a tobacco rod segment, a spill, an additive release component such as a capsule, a thread, beads, a paper such as a plug wrap, a tipping paper or a cigarette paper.

In one embodiment, the tobacco industry product is a non-combustible aerosol provision system.

In one embodiment, the tobacco industry product comprises one or more components of a non-combustible aerosol provision system, such as a heater and an aerosolizable substrate.

In one embodiment, the aerosol provision system is an electronic cigarette also known as a vaping device.

In one embodiment the electronic cigarette comprises a heater, a power supply capable of supplying power to the heater, an aerosolizable substrate such as a liquid or gel, a housing and optionally a mouthpiece.

In one embodiment the aerosolizable substrate is contained in a substrate container. In one embodiment the substrate container is combined with or comprises the heater.

In one embodiment, the tobacco industry product is a heating product which releases one or more compounds by heating, but not burning, a substrate material. The substrate material is an aerosolizable material which may be for example tobacco or other non-tobacco products, which may or may not contain nicotine. In one embodiment, the heating product is a tobacco heating product.

In one embodiment, the heating product is an electronic device.

In one embodiment, the tobacco heating product comprises a heater, a power supply capable of supplying power to the heater, an aerosolizable substrate such as a solid or gel material.

In one embodiment the heating product is a non-electronic article.

In one embodiment the heating product comprises an aerosolizable substrate such as a solid or gel material and a heat source which is capable of supplying heat energy to the aerosolizable substrate without any electronic means, such as by burning a combustion material, such as charcoal.

In one embodiment the heating product also comprises a filter capable of filtering the aerosol generated by heating the aerosolizable substrate.

In some embodiments the aerosolizable substrate material may comprise a vapour or aerosol generating agent or a humectant, such as glycerol, propylene glycol, triacetin or diethylene glycol.

In one embodiment, the tobacco industry product is a hybrid system to generate aerosol by heating, but not burning, a combination of substrate materials. The substrate materials may comprise for example solid, liquid or gel which may or may not contain nicotine. In one embodiment, the hybrid system comprises a liquid or gel substrate and a solid substrate. The solid substrate may be for example tobacco or other non-tobacco products, which may or may not contain nicotine. In one embodiment, the hybrid system comprises a liquid or gel substrate and tobacco.

In a further embodiment the tobacco industry product may be a tobacco heating device or hybrid device or e-cigarette or the like.

Typically in tobacco heating devices or hybrid devices, an aerosol is generated by the transfer of heat from a heat source to a physically separate aerosol-forming substrate or material, which may be located within, around or downstream of the heat source. During smoking, volatile compounds are released from the aerosol-forming substrate by heat transfer from the heat source and entrained in air drawn through the smoking article. As the released compounds cool, they condense to form an aerosol that is inhaled by the user.

Aerosol-generating articles and devices for consuming or smoking tobacco heating devices are known in the art. They can include, for example, electrically heated aerosol-generating devices in which an aerosol is generated by the transfer of heat from one or more electrical heating elements of the aerosol-generating device to the aerosol-forming substrate of a tobacco heating device.

Suitably the tobacco heating device may be an aerosol-generating device.

Preferably the tobacco heating device may be a heat-not-burn device. Heat-not-burn devices are known in the art and release compounds by heating, but not burning, tobacco.

An example of a suitable, heat-not-burn device may be one taught in WO2013/034459 or GB2515502 which are incorporated herein by reference.

In one embodiment the aerosol-forming substrate of a tobacco heating device may be a tobacco industry product in accordance with the present invention.

In one embodiment the tobacco heating device may be a hybrid device.

Polynucleotides/Polypeptides/Constructs

In certain embodiments of the present invention, constructs which modulate expression or nucleic acid sequence of at least one armadillo repeat protein may be transformed into plant cells, suitably under the direction of a promoter.

In certain embodiments of the present invention, constructs which decrease (i.e. inhibit) the expression of or which modify the or nucleic acid sequence of at least one armadillo repeat protein may be transformed into plant cells under the direction of a promoter. For example, the genetic construct may be a gene editing construct or may comprise an RNAi molecule, which may comprise a small interfering RNA (siRNA) molecule, or a short hairpin loop (shRNA) molecule.

In certain embodiments of the present invention, constructs which increase expression of an armadillo repeat protein may be transformed into plant cells, suitably under the direction of a promoter e.g. constructs which encode a gene encoding an armadillo repeat protein such as an endogenous armadillo repeat protein.

Constructs may be introduced into plants according to the present invention by means of suitable vector, e.g. plant transformation vectors. A plant transformation vector may comprise an expression cassette comprising 5'-3' in the direction of transcription, a promoter sequence, a construct sequence targeting gene encoding an armadillo repeat protein and, optionally a 3' untranslated, terminator sequence including a stop signal for RNA polymerase and a polyadenylation signal for polyadenylase. The promoter sequence may be present in one or more copies, and such copies may be identical or variants of a promoter sequence as described above. The terminator sequence may be obtained from plant, bacterial or viral genes. Suitable terminator sequences are the pea rbcS E9 terminator sequence, the nos terminator sequence derived from the nopaline synthase gene of *Agrobacterium tumefaciens* and the 35S terminator sequence from cauliflower mosaic virus, for example. A person skilled in the art will be readily aware of other suitable terminator sequences.

The construct of the present invention may also comprise a gene expression enhancing mechanism to increase the strength of the promoter. An example of such an enhancer element is one derived from a portion of the promoter of the pea plastocyanin gene, and which is the subject of International Patent Application No. WO 97/20056 which is incorporated herein by reference. Suitable enhancer elements may be the nos enhancer element derived from the nopaline synthase gene of *Agrobacterium tumefaciens* and the 35S enhancer element from cauliflower mosaic virus, for example.

These regulatory regions may be derived from the same gene as the promoter DNA sequence or may be derived from different genes, from *Nicotiana tabacum* or other organisms, for example from a plant of the family Solanaceae, or from the subfamily Cestroideae. All of the regulatory regions should be capable of operating in cells of the tissue to be transformed.

The promoter DNA sequence may be derived from the same gene as the gene of interest, e.g. the gene the promoter is going to direct, for instance a gene encoding an armadillo repeat protein according to the invention, a coding sequence used in the present invention or may be derived from a different gene, from *Nicotiana tabacum*, or another organism, for example from a plant of the family Solanaceae, or from the subfamily Cestroideae.

The expression cassette may be incorporated into a basic plant transformation vector, such as pBIN 19 Plus, pBI 101, pKYLX71:35S2, pCAMBIA2300 or other suitable plant transformation vectors known in the art. In addition to the expression cassette, the plant transformation vector will contain such sequences as are necessary for the transformation process. These may include the *Agrobacterium* vir genes, one or more T-DNA border sequences, and a selectable marker or other means of identifying transgenic plant cells.

The term "expression vector or plant transformation vector" means a construct capable of in vivo or in vitro expression. Preferably, the expression vector is incorporated in the genome of the organism. In one embodiment the vector of the present invention expresses a protein e.g. an armadillo repeat protein as described herein. The term "incorporated" preferably covers stable incorporation into the genome.

Techniques for transforming plants are well known within the art and include *Agrobacterium*-mediated transformation, for example. The basic principle in the construction of genetically modified plants is to insert genetic information in the plant genome so as to obtain a stable maintenance of the inserted genetic material. A review of the general techniques may be found in articles by Potrykus (*Annu Rev Plant Physiol Plant Mol Biol* [1991] 42:205-225) and Christon (AgroFood-Industry Hi-Tech March/April 1994 17-27), which are incorporated herein by reference.

Typically, in *Agrobacterium*-mediated transformation a binary vector carrying a foreign DNA of interest, i.e. a construct according to the present invention, is transferred from an appropriate *Agrobacterium* strain to a target plant by the co-cultivation of the *Agrobacterium* with explants from the target plant. Transformed plant tissue is then regenerated on selection media, which selection media comprises a selectable marker and plant growth hormones. An alternative is the floral dip method (Clough & Bent, 1998 Plant J. 1998 December; 16(6):735-43, which is incorporated herein by reference) whereby floral buds of an intact plant are brought into contact with a suspension of the *Agrobacterium* strain containing the chimeric gene, and following seed set, transformed individuals are germinated and identified by growth on selective media. Direct infection of plant tissues by *Agrobacterium* is a simple technique which has been widely employed and which is described in Butcher D. N. et al., (1980), *Tissue Culture Methods for Plant Pathologists*, eds.: D. S. Ingrams and J. P. Helgeson, 203-208 which is incorporated herein by reference.

Further suitable transformation methods include direct gene transfer into protoplasts using polyethylene glycol or electroporation techniques, particle bombardment, microinjection and the use of silicon carbide fibres for example. Transforming plants using ballistic transformation, including the silicon carbide whisker technique are taught in Frame B R, Drayton P R, Bagnaall S V, Lewnau C J, Bullock W P, Wilson H M, Dunwell J M, Thompson J A & Wang K (1994) which is incorporated herein by reference. Production of fertile transgenic maize plants by silicon carbide whisker-mediated transformation is taught in *The Plant Journal* 6: 941-948, which is incorporated herein by reference) and viral transformation techniques is taught in for example Meyer P, Heidmann I & Niedenhof I (1992), which is incorporated herein by reference. The use of cassava mosaic virus as a vector system for plants is taught in *Gene* 110: 213-217, which is incorporated herein by reference. Further teachings on plant transformation may be found in EP-A-0449375, incorporated herein by reference.

In a further aspect, the present invention relates to a vector system which carries a construct and introducing it into the genome of an organism, such as a plant, suitably a tobacco plant. The vector system may comprise one vector, but it may comprise two vectors. In the case of two vectors, the vector system is normally referred to as a binary vector system. Binary vector systems are described in further detail in Gynheung Anetal, (1980), Binary Vectors, *Plant Molecular Biology Manual* A3, 1-19, which is incorporated herein by reference.

One extensively employed system for transformation of plant cells uses the Ti plasmid from *Agrobacterium tumefaciens* or a Ri plasmid from *Agrobacterium rhizogenes* described by An et al., (1986), *Plant Physiol.* 81, 301-305 and Butcher D. N. et al., (1980), *Tissue Culture Methods for Plant Pathologists*, eds.: D. S. Ingrams and J. P. Helgeson, 203-208 which are incorporated herein by reference. After each introduction method of the desired exogenous gene according to the present invention in the plants, the presence and/or insertion of further DNA sequences may be necessary. The use of T-DNA for the transformation of plant cells has been intensively studied and is described in EP-A-120516; Hoekema, in: The Binary Plant Vector System Offset-drukkerij Kanters B. B., Amsterdam, 1985, Chapter V; Fraley, et al, *Crit. Rev. Plant Sci.*, 4:1-46; and Anetal., *EMBO J* (1985) 4:277-284, incorporated herein by reference.

Plant cells transformed with construct(s) which modulate the expression of or which modify the nucleic acid sequence of at least one gene encoding an armadillo repeat protein may be grown and maintained in accordance with well-known tissue culturing methods such as by culturing the cells in a suitable culture medium supplied with the necessary growth factors such as amino acids, plant hormones, vitamins, etc.

The term "transgenic plant" in relation to the present invention includes any plant that comprises a construct which modulates the expression of or which modifies the nucleic acid sequence of at least one gene encoding an armadillo repeat protein according to the invention. Accordingly a transgenic plant is a plant which has been transformed with a construct according to the invention. Preferably the transgenic plant exhibits modulated alkaloid content and/or modulated TSNA content (or precursor thereof) according to the present invention. The term "transgenic plant" does not cover native nucleotide coding sequences in their natural environment when they are under the control of their native promoter which is also in its natural environment.

In one aspect, gene encoding an armadillo repeat protein, a construct, plant transformation vector or plant cell according to the present invention is in an isolated form. The term "isolated" means that the sequence is at least substantially free from at least one other component with which the sequence is naturally associated in nature and as found in nature.

In one aspect, gene encoding an armadillo repeat protein, a construct, plant transformation vector or plant cell according to the invention is in a purified form. The term "purified" means in a relatively pure state, e.g. at least about 90% pure, or at least about 95% pure or at least about 98% pure.

The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" in relation to the present invention includes genomic DNA, cDNA, synthetic DNA, and RNA. Preferably it means DNA, more preferably cDNA sequence coding for the present invention.

In a preferred embodiment, the nucleotide sequence when relating to and when encompassed by the per se scope of the present invention, i.e. the gene encoding an armadillo repeat protein, includes the native nucleotide sequence when in its natural environment and when it is linked to its naturally associated sequence(s) that is/are also in its/their natural environment. For ease of reference, we shall call this preferred embodiment the "native nucleotide sequence". In this regard, the term "native nucleotide sequence" means an entire nucleotide sequence that is in its native environment and when operatively linked to an entire promoter with which it is naturally associated, which promoter is also in its native environment.

The nucleotide sequence for use in the present invention may be present in a vector in which the nucleotide sequence is operably linked to regulatory sequences capable of providing for the expression of the nucleotide sequence by a suitable host organism. The constructs for use in the present invention may be transformed into a suitable host cell as described herein to provide for expression of a polypeptide of the present invention. The choice of vector e.g. a plasmid, cosmid, or phage vector will often depend on the host cell into which it is to be introduced. Vectors may be used in vitro, for example for the production of RNA or used to transfect, transform, transduce or infect a host cell.

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of gene encoding an armadillo repeat protein as described herein operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters and enhancers and other expression regulation signals. The term "promoter" is used in the normal sense of the art, e.g. an RNA polymerase binding site. The nucleotide sequence within a construct which encodes gene encoding an armadillo repeat protein may be operably linked to at least a promoter.

The term "construct"—which is synonymous with terms such as "cassette" or "vector"—includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment. The construct may even contain or express a marker, which allows for the selection of the genetic construct.

In some embodiments, a promoter may be operably linked to nucleotide sequence in a construct or vector which is used to modulate the concentration and/or total content of nicotine in a cell or cell culture or tobacco plant or part thereof.

In some embodiments the promoter may be selected from the group consisting of: a constitutive promoter, a tissue-specific promoter, a developmentally-regulated promoter and an inducible promoter.

In one embodiment the promoter may be a constitutive promoter.

A constitutive promoter directs the expression of a gene throughout the various parts of a plant continuously during plant development, although the gene may not be expressed at the same level in all cell types. Examples of known constitutive promoters include those associated with the cauliflower mosaic virus 35S transcript (Odell J T, Nagy F, Chua N H. (1985). Identification of DNA sequences required for activity of the cauliflower mosaic virus 35S promoter. Nature. 313 810-2), the rice actin 1 gene (Zhang W, McElroy D, Wu R. (1991). Analysis of rice Act1 5' region activity in transgenic rice plants. Plant Cell 3 1155-65) and the maize ubiquitin 1 gene (Cornejo M J, Luth D, Blankenship K M, Anderson O D, Blechl A E. (1993). Activity of a maize ubiquitin promoter in transgenic rice. Plant Molec. Biol. 23 567-81). Constitutive promoters such as the Carnation Etched Ring Virus (CERV) promoter (Hull R, Sadler J, Longstaff M (1986) (CaMV/35S), figwort mosaic virus 35S promoter. The sequence of carnation etched ring virus DNA: comparison with cauliflower mosaic virus and retroviruses. EMBO Journal, 5(2):3083-3090).

The constitutive promoter may be selected from a: a carnation etched ring virus (CERV) promoter, a cauliflower mosaic virus (CaMV 35S promoter), a promoter from the rice actin 1 gene or the maize ubiquitin 1 gene.

The promoter may be a tissue specific promoter. A tissue-specific promoter is one which directs the expression of a gene in one (or a few) parts of a plant, usually throughout the lifetime of those plant parts. The category of tissue-specific promoter commonly also includes promoters whose specificity is not absolute, i.e. they may also direct expression at a lower level in tissues other than the preferred tissue. Tissue specific promoters include the phaseolin-promoter, legumin b4-promoter, usp-promoter, sbp-promoter, ST-LS1 promoter, B33 (patatin class I promoter).

In another embodiment the promoter may be a developmentally-regulated promoter.

A developmentally-regulated promoter directs a change in the expression of a gene in one or more parts of a plant at a specific time during plant development. The gene may be expressed in that plant part at other times at a different (usually lower) level, and may also be expressed in other plant parts.

In one embodiment the promoter may be an inducible promoter.

An inducible promoter is capable of directing the expression of a gene in response to an inducer. In the absence of the inducer the gene will not be expressed. The inducer may act directly upon the promoter sequence, or may act by counteracting the effect of a repressor molecule. The inducer may be a chemical agent such as a metabolite, a protein, a growth regulator (such as auxin and salicylic acid which activate the OCS promoter), or a toxic element, a physiological stress such as heat, light (such as the soybean SSU promoter), wounding (e.g. the nos, nopaline synthase promoter), or osmotic pressure, or an indirect consequence of the action of a pathogen or pest. A developmentally-regulated promoter might be described as a specific type of inducible promoter responding to an endogenous inducer produced by the plant or to an environmental stimulus at a particular point in the life cycle of the plant. Examples of known inducible promoters include those associated with wound response, such as described by Warner S A, Scott R, Draper J. ((1993) Plant J. 3 191-201), temperature response as disclosed by Benfey & Chua (1989) (Benfey, P. N., and Chua, N-H. ((1989) Science 244 174-181), and chemically induced, as described by Gatz ((1995) Methods in Cell Biol. 50 411-424).

A nucleotide sequence encoding either a protein which has the specific properties as gene encoding an armadillo repeat protein as defined herein or a protein which is suitable for modification may be identified and/or isolated and/or purified from any cell or organism producing said protein. Various methods are well known within the art for the identification and/or isolation and/or purification of nucleotide sequences. By way of example, PCR amplification techniques to prepare more of a sequence may be used once a suitable sequence has been identified and/or isolated and/or purified.

In a yet further alternative, the nucleotide sequence encoding the armadillo repeat protein may be prepared synthetically by established standard methods, e.g. the phosphoroamidite method described by Beucage S. L. et al., (1981) *Tetrahedron Letters* 22, p 1859-1869 which is incorporated herein by reference, or the method described by Matthes et al., (1984) *EMBO J.* 3, p 801-805 which is incorporated herein by reference. In the phosphoroamidite method, oligonucleotides are synthesised, e.g. in an automatic DNA synthesiser, purified, annealed, ligated and cloned in appropriate vectors.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The present invention also encompasses the use of sequences having a degree of sequence identity or sequence homology with amino acid sequence(s) of a polypeptide having the specific properties defined herein or of any nucleotide sequence i.e. armadillo repeat protein gene encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence and/or fragments should provide and/or encode a polypeptide which retains the functional activity and/or enhances the activity of the armadillo repeat protein gene. Typically, the homologous sequences will comprise the same active sites etc. as the subject amino acid sequence for instance or will encode the same active sites. Although homology can also be considered in terms of similarity (i.e. amino acid residues having similar chemical properties/functions), in the context of the present invention it is preferred to express homology in terms of sequence identity. Homologous sequences typically retain functional domains or motifs. Suitably, homologues of armadillo repeat proteins may contain armadillo repeat protein domains and an active site comprising a conserved lysine residue.

In one embodiment, a homologous sequence is taken to include an amino acid sequence or nucleotide sequence which has one, two or several additions, deletions and/or substitutions compared with the subject sequence.

Sequence Identity

Sequence identity comparisons can be conducted by eye, or more usually, with the aid of readily available sequence comparison programs. These commercially available computer programs can calculate % homology between two or more sequences. % homology or % identity may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al. 1999 Short Protocols in Molecular Biology, 4th Ed—Chapter 18), BLAST 2 (see FEMS Microbiol Lett 1999 174(2): 247-50; FEMS Microbiol Lett 1999 177(1): 187-8 and tatiana@ncbi.nlm.nih.gov), FASTA (Altschul et al. 1990 J. Mol. Biol. 403-410) and AlignX for example. At least BLAST, BLAST 2 and FASTA are available for offline and online searching (see Ausubel et al. 1999, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins DG & Sharp PM (1988), Gene 73(1), 237-244). Once the software has produced an optimal alignment, it is possible to calculate % homology, preferably % sequence identity. The software typically does this as part of the sequence comparison and generates a numerical result.

Should gap penalties be used when determining sequence identity, then preferably the following parameters are used for pairwise alignment:

| FOR BLAST | |
| --- | --- |
| GAP OPEN | 0 |
| GAP EXTENSION | 0 |

| FOR CLUSTAL | DNA | PROTEIN | |
| --- | --- | --- | --- |
| WORD SIZE | 2 | 1 | K triple |
| GAP PENALTY | 15 | 10 | |
| GAP EXTENSION | 6.66 | 0.1 | |

In one embodiment, CLUSTAL may be used with the gap penalty and gap extension set as defined above. In some embodiments the gap penalties used for BLAST or CLUSTAL alignment may be different to those detailed above. The skilled person will appreciate that the standard parameters for performing BLAST and CLUSTAL alignments may change periodically and will be able to select appropriate parameters based on the standard parameters detailed for BLAST or CLUSTAL alignment algorithms at the time.

Suitably, the degree of identity with regard to a nucleotide sequence is determined over at least 50 contiguous nucleotides, preferably over at least 60 contiguous nucleotides, preferably over at least 70 contiguous nucleotides, preferably over at least 80 contiguous nucleotides, preferably over at least 90 contiguous nucleotides, preferably over at least 100 contiguous nucleotides, preferably over at least 150 contiguous nucleotides, preferably over at least 200 contiguous nucleotides, preferably over at least 250 contiguous nucleotides, preferably over at least 300 contiguous nucleotides, preferably over at least 350 contiguous nucleotides, preferably over at least 400 contiguous nucleotides, preferably over at least 450 contiguous nucleotides, preferably over at least 500 contiguous nucleotides, preferably over at least 550 contiguous nucleotides, preferably over at least 600 contiguous nucleotides, preferably over at least 650 contiguous nucleotides, or preferably over at least 700 contiguous nucleotides.

Suitably, the degree of identity with regard to a nucleotide, cDNA, cds or amino acid sequence may be determined over the whole sequence.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-1-phenylalanine*, L-allyl-glycine*, β-alanine*, L-α-amino butyric acid*, L-γ-amino butyric acid*, L-α-amino isobutyric acid*, L-ε-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid # and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, which will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol*. (1995) 13(4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

The present invention also encompasses sequences that are complementary to the nucleic acid sequences of the present invention or sequences that are capable of hybridising either to the sequences of the present invention or to sequences that are complementary thereto. The term "hybridisation" as used herein shall include "the process by which a strand of nucleic acid joins with a complementary strand through base pairing" as well as the process of amplification as carried out in polymerase chain reaction (PCR) technologies.

The present invention also relates to nucleotide sequences that can hybridise to the nucleotide sequences of the present invention (including complementary sequences of those presented herein). Preferably, hybridisation is determined under stringency conditions (e.g. 50° C. and 0.2×SSC {1×SSC=0.15 M NaCl, 0.015 M $Na_3$ citrate pH 7.0}). More preferably, hybridisation is determined under high stringency conditions (e.g. 65° C. and 0.1×SSC {1×SSC=0.15 M NaCl, 0.015 M $Na_3$ citrate pH 7.0}).

A review of the general techniques used for transforming plants may be found in articles by Potrykus (*Annu Rev Plant Physiol Plant Mol Biol* [1991] 42:205-225) and Christou (Agro-Food-Industry Hi-Tech March/April 1994 17-27), which are incorporated herein by reference. Further teachings on plant transformation may be found in EP-A-0449375, incorporated herein by reference.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation. The term "protein", as used herein, includes proteins, polypeptides, and peptides. As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an enzyme" or "a nitrate reductase" includes a plurality of such candidate agents and equivalents thereof known to those skilled in the art, and so forth.

Advantages

It has been surprisingly found that by modulating the expression of at least one armadillo repeat protein as taught herein which acts as a positive regulator of nicotine in tobacco, the alkaloid content (e.g. nicotine and/or nornicotine and/or PON content) and/or TSNA content of plants can be modulated (e.g. decreased). Thereby tobacco products with modulated alkaloid (e.g. nicotine and/or nornicotine and/or PON content) and/or TSNA content and commercially desirable traits sought after by consumers of tobacco products can be produced.

The present inventors have surprisingly determined a method for modulating (e.g. decreasing) the alkaloid content (e.g. nicotine and/or nornicotine and/or PON content content), and/or TSNA content of a plant (e.g. tobacco plant) by modulating (e.g. decreasing) the expression of an armadillo repeat protein. Alkaloid (e.g. nicotine content) or TSNA content of a plant (e.g. tobacco plant) may be decreased by decreasing or inhibiting the expression of gene encoding an armadillo repeat protein. Alkaloid (e.g. nicotine content) or TSNA content of a plant (e.g. tobacco plant) may be increased by increasing the expression of gene encoding an armadillo repeat protein. Prior to the present invention it had not been known that modulation of the expression of an armadillo repeat protein as described herein could be used to modulate alkaloid (e.g. nicotine and/or nornicotine and/or PON content) and/or TSNA content of a plant (e.g. a tobacco plant).

The present inventors have determined that the inhibition of the expression of a gene encoding an armadillo repeat protein can reduce the alkaloid content (e.g. nicotine content) of the modified plant to a surprisingly low level.

The publications discussed herein are provided solely for their disclosure prior to the filing date of the present application. Nothing herein is to be construed as an admission that such publications constitute prior art to the claims appended hereto.

EXAMPLES

Example 1—Transient Overexpression of an Armadillo Repeat Protein Increases Alkaloid Content in Leaves Methods and Materials
Cloning
Armadillo Repeat Protein Expression Vector The gene sequence (SEQ ID No. 3) was amplified from a Gateway™ compatible cDNA library using primers located outside restriction sites flanking the gene sequence. The gene sequence was then transferred to an expression vector.

The resulting plasmid was sequenced and transformed into *Agrobacterium tumefaciens* GV3101pMP90 by heat shock and transiently expressed in TN90 leaves.
Transient Gene Expression

*Agrobacterium tumefaciens* GV3101 strains carrying the construct of interest were grown overnight in Luria-Bertani (LB) medium supplemented with appropriate antibiotics. Cultures are spun down and re-suspended in buffer containing 10 mM MgCl2, 10 mM MES pH 5.6 and 100 μM acetosyringone to OD600=0.6 and incubated for one hour at room temperature. Infiltration is performed with a needleless syringe into TN90 leaves. Samples are taken 5 days post-infiltration.

Tests were performed in three biological replicates.
Alkaloid Measurement

Relative content of pyridine alkaloids was determined by reversed phase high performance liquid chromatography with tandem mass spectrometry (LC-MS/MS). Chromatographic separation is achieved using a Gemini-NX column (100 mm×3.0 mm, particle size 3 μm, Phenomenex) and gradient chromatographic separation using 6.5 mM ammonium acetate buffer (aq) (pH10) and Methanol.

Mass Spectrometer operates in electrospray (ESI) positive mode using scheduled MRM data acquisition. Two MRM transitions are monitored for each analyte and one for the isotope labelled internal standard.

| Analyte | Precursor Ion | Daughter Ion (quant/confirm) |
|---|---|---|
| Nicotine | 163.1 | 130/106 |
| Nicotine d4 | 167.1 | 134.1 |
| Anabasine | 163.1 | 80/120 |
| Anatabine | 161.1 | 144/80 |
| Nornicotine | 149.1 | 80/130 |
| Nornicotine d4 | 153.1 | 84.1 |
| PON | 176.1 | 106.0/148 |
| PON d4 | 183.1 | 110.0 |

Statistical Analysis

Statistical significances based on one-way ANOVA analyses is performed with Prism 5.01 software (GraphPad Software).

Results

Figure 1:
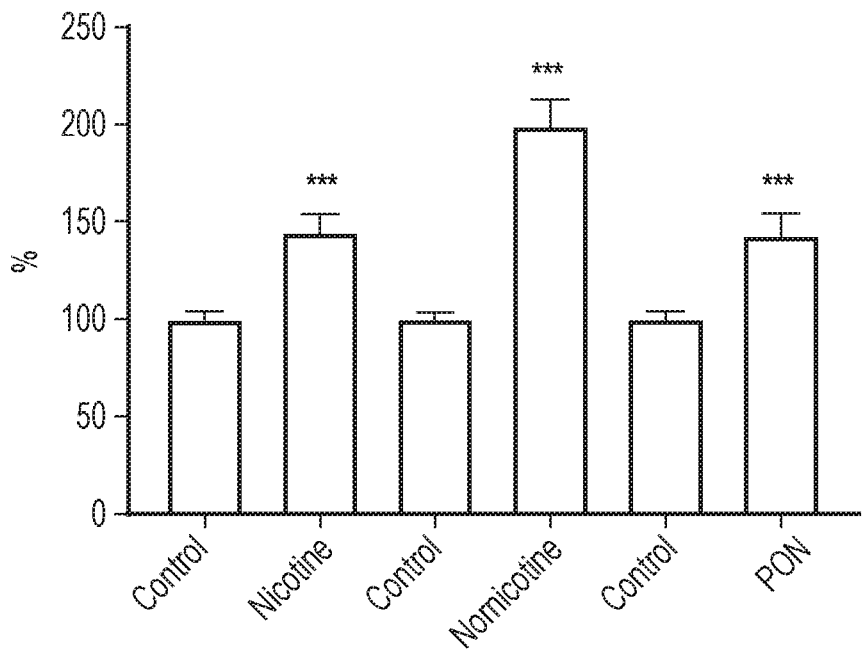
FIG. 1 shows the nicotine, nornicotine and PON content of 5-week-old TN90 leaves expressing Nitab4.5_0002810g0020.2 (SEQ ID No. 3). Nicotine, nornicotine and PON content is represented relative to control and comprises three biological replicates analysed by t-test. Values are shown as means±SEM. Asterisks indicate statistical significance of P value ≤0.001.

Alkaloid content of 5-week-old TN90 leaves expressing the Nitab4.5_0002810g0020.2 construct is shown in FIG. 1. Nicotine, Nornicotine and PON content is represented relative to control and comprises three biological replicates analysed by one-way ANOVA and Tukey's multiple-comparison post-test. Values are shown as means±SEM. Asterisks indicate statistical significance of P value ≤0.001.

Overexpression of Nitab4.5_0002810g0020.2 leads to a significant increase in nicotine, nornicotine and PON content in leaves.

Conclusions

Nitab4.5_0002810g0020.2 is a positive regulator of alkaloid content, in particular nicotine, nornicotine and PON content in leaves and is a regulator of pyridine alkaloids in tobacco.

Example 2—Virus-Induced Gene Silencing (VIGS) of an Armadillo Repeat Protein Decreases Alkaloid Content in Leaves Virus-Induced Gene Silencing (VIGS)

For virus induced gene silencing, a 300-nucleotide cDNA fragment was synthesized and cloned with In-Fusion cloning kit into pTV00 (between EcoRI and XhoI sites) using the following primers Nitab4.5_0002810g0020.2_InFusion 5' TGAGTAAGGTTACCGAATTC (SEQ ID No. 4); and Nitab4.5_0002810g0020.2_InFusion 3' CTCGAGGCCC-GGGCATGTCC (SEQ ID No. 5) to form TRV2-Nitab4.5_0002810g0020.2. The plasmid was then transformed into *A. tumefaciens* GV3101.

The TRV vector comprising both (TRV RNA1) and (TRV RNA2) comprising the targeted nucleotide sequence were separately propagated in *A. tumefaciens*. These cultures were mixed (1:1) and syringe-infiltration into 2-week-old TN90 plants. The silencing effect was assessed five weeks post-virus infection by assessing the expression level of the target gene.

Silencing

VIGS assays were performed as previously described (Ratcliff et al., 2001) Ratcliff, F., et al., (2001), The Plant Journal, 25: 237-245 (incorporated herein by reference). Briefly, independent cultures of *A. tumefaciens* GV3101 carrying TRV2 and TRV1 plasmids were propagated overnight in LB medium supplemented with appropriate antibiotics. Cultures were resuspended in VIGS buffer (10 mM morpholineethanesulfonic acid pH 5.6, 10 mM MgCL$_2$, and 100 μM acetocyringone) adjusting optical density to OD$_{600}$=1, and incubated overnight at room temperature in the dark. These cultures were mixed (1:1) and syringe-infiltrated into 2-week-old TN90 plants. The silencing effect was assessed two weeks post-virus infection by assessing the expression level of the target gene. TRV-Luciferase was used as a negative control and TRV-PDS (reduced chlorophyll content of the silenced leaves) was used as a phenotypic silencing control.

Results

Figure 2:
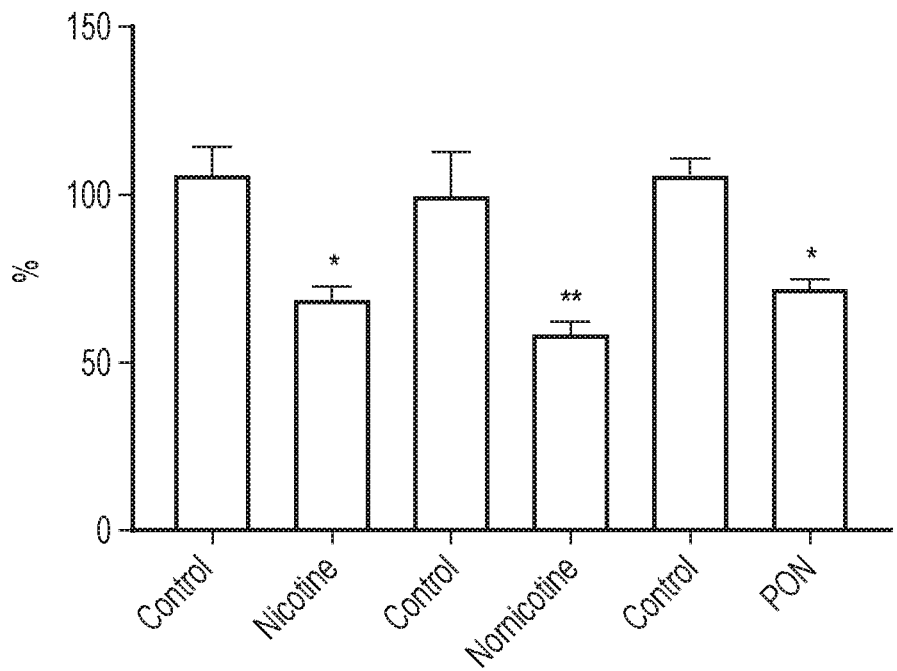
FIG. 2 shows the nicotine, nornicotine and PON content of 5-week-old TN90 leaves expressing a construct which silences Nitab4.5_0002810g0020.2 (SEQ ID No. 3) by virus-induced gene silencing. Nicotine, nornicotine and PON content is represented relative to control and comprises three biological replicates analysed by t-test. Values are shown as means±SEM. Asterisks indicate statistical significance of P value ≤0.001.

Nicotine, nornicotine and PON content of 5-week-old TN90 leaves expressing constructs which silence Nitab4.5_0002810g0020.2 are shown in FIG. 2. Content is represented relative to control and comprises three biological replicates analysed by t-test. Values are shown as means±SEM. Asterisks indicate statistical significance of P value ≤0.001.

Silencing Nitab4.5_0002810g0020.2 leads to a decrease in nicotine, nornicotine and PON content in leaves.

Conclusions

Nitab4.5_0002810g0020.2 is a positive regulator of alkaloid content, in particular nicotine, nornicotine and PON content in leaves and is a regulator of pyridine alkaloids in tobacco.

Example 3—Nitab4.5 0002810g0020.2-Mediated Regulation of Alkaloid Content Requires the Arm Domain In order to determine whether the Arm domain is required for regulation of alkaloid content, a construct was made in which the Arm domain of Nitab4.5_0002810g0020.2 was deleted (Delta-Arm).

The method for expressing this construct is as described in Example 1.

Results

Figure 3:
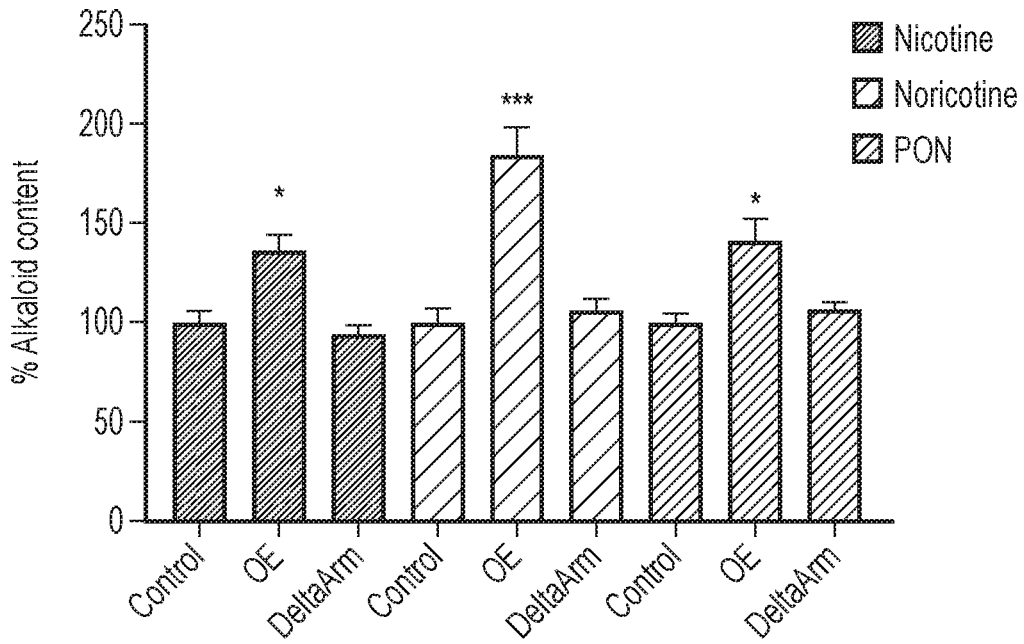
FIG. 3 shows the alkaloid content of 5-week-old TN90 leaves expressing the following constructs: OE=over expressing Nitab4.5_0002810g0020.2; DeltaArm= expressing a Nitab4.5_0002810g0020.2 sequence which has been modified to delete the armadillo repeat domain (Arm). Alkaloid content is represented relative to control and comprises three biological replicates analysed by one-way ANOVA and Tukey's multiple-comparison post-test. Values are shown as means±SEM. Asterisks indicate statistical significance of P value ≤0.001.

Alkaloid content of 5-week-old TN90 leaves expressing Nitab4.5_0002810g0020.2 and Nitab4.5_0002810g0020.2 Delta-Arm are shown in FIG. 3. Alkaloid content is represented relative to control and comprises three biological replicates analysed by one-way ANOVA and Tukey's multiple-comparison post-test. Values are shown as means±SEM. Asterisks indicate statistical significance of P value ≤0.001.

Leaves expressing the Nitab4.5_0002810g0020.2-DeltaArm construct contain less nicotine, nornicotine and PON compared to leaves which express the Nitab4.5_0002810g0020.2 construct.

Conclusion

Nitab4.5_0002810g0020.2-mediated regulation of alkaloid content requires the Arm domain.

Figure 4:
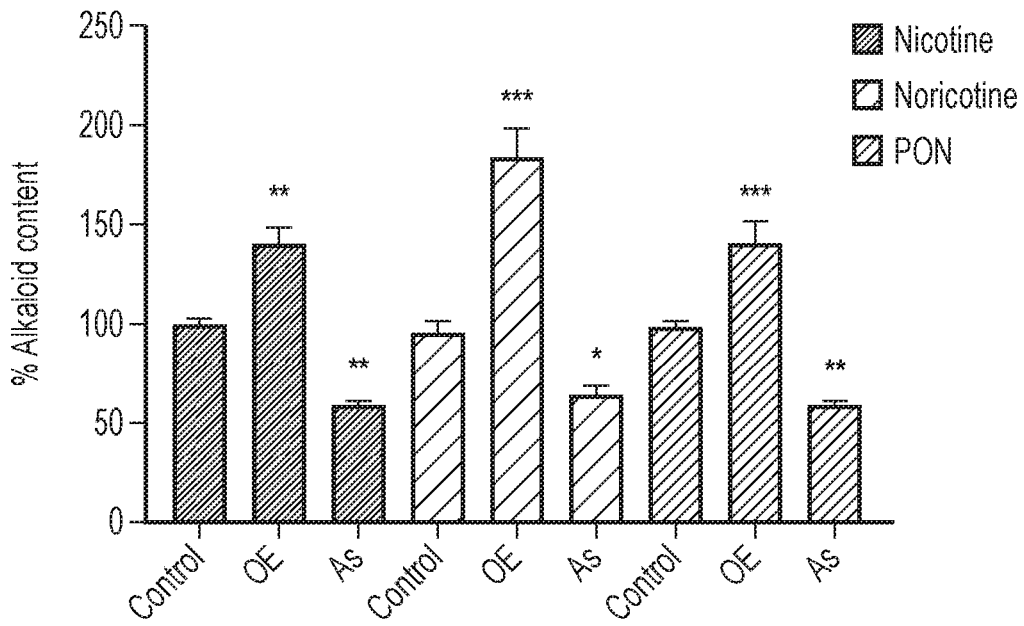
FIG. 4 shows the alkaloid content of 5-week-old TN90 leaves expressing the following constructs: OE=over expressing Nitab4.5_0002810g0020.2; As=Nitab4.5_0002810g0020.2 antisense. Alkaloid content is represented relative to control and comprises three biological replicates analysed by one-way ANOVA and Tukey's multiple-comparison post-test. Values are shown as means±SEM. Asterisks indicate statistical significance of P value ≤0.001.

Example 4—Transient Overexpression of Nitab4.5_0002810g0020.2 Antisense Leads to a Significant Reduction in Nicotine, Nornicotine and PON Alkaloid content of 5-week-old TN90 leaves expressing Nitab4.5_0002810g0020.2 and an antisense directed against Nitab4.5_0002810g0020.2 are shown in FIG. 4. Alkaloid content is represented relative to control and comprises three biological replicates analysed by one-way ANOVA and Tukey's multiple-comparison post-test. Values are shown as means±SEM. Asterisks indicate statistical significance of P value ≤0.001.

Leaves comprising the Nitab4.5_0002810g0020.2 antisense contain less nicotine, nornicotine and PON compared to leaves which express the Nitab4.5_0002810g0020.2 construct.

Conclusion

Transient overexpression of Nitab4.5_0002810g0020.2 antisense leads to a significant reduction in nicotine, nornicotine and PON.

Example 5—Transient Expression of Artificial miRNA Targeting Nitab4.5_0002810a0020.2 Leads to a Significant Reduction in Nicotine, Nornicotine and PON Alkaloid content of 5-week-old TN90 leaves expressing Nitab4.5_0002810g0020.2 and an artificial miRNA targeting Nitab4.5_0002810g0020.2 (SEQ ID No. 6) are shown in FIG. 5. Alkaloid content is represented relative to control and comprises three biological replicates analysed by one-way ANOVA and Tukey's multiple-comparison post-test. Values are shown as means±SEM. Asterisks indicate statistical significance of P value ≤0.001.

Conclusion

Transient expression of artificial miRNA targeting Nitab4.5_0002810g0020.2 leads to a significant reduction in nicotine, nornicotine and PON.

Figure 6:
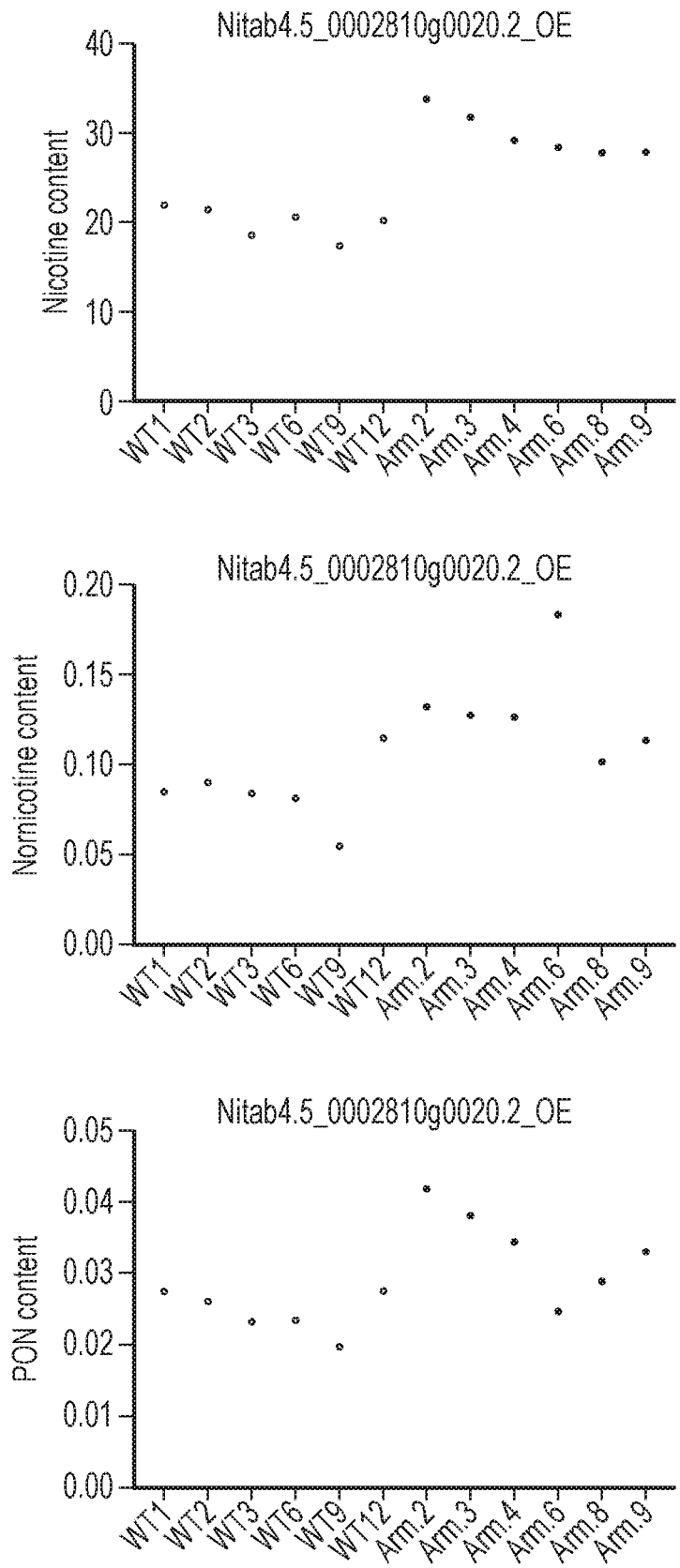
FIG. 6 shows the alkaloid content of greenhouse-grown TN90 plants at 12 leaf stage overexpressing Nitab4.5_0002810g0020.2 in stable T1 lines. Every point represents the mean of 24 measurements sampled from bottom to top leaf.

Example 6—Stable T1 Selected Lines Overexpressing Nitab4.5_0002810g020.2 have Increased Alkaloid Content Nicotine, nornicotine and PON content of greenhouse-grown TN90 plants at 12 leaf stage overexpressing Nitab4.5_0002810g0020.2 are shown in FIG. 6.

Every point represents the mean of 24 measurements sampled from bottom to top leaf.

FIG. 6 shows that stable T1 lines which overexpress the armadillo repeat protein have increased alkaloid content, in particular increased nicotine, nornicotine and PON content.

Example 7—Adult Plants Silenced for Nitab4.5_0002810g020.2 have Decreased Alkaloid Content Alkaloid content of greenhouse-grown TN90 plants silenced for Nitab4.5_0002810g0020.2 is shown in FIG. 7.

Alkaloid content is represented relative to control and comprises three measurements of 20 plants/genotype analysed by one-way ANOVA and Tukey's multiple-comparison post-test. Values are shown as means±SEM. Asterisks indicate statistical significance of P value ≤0.001.

FIG. 7 shows that adult plants which are silenced for the armadillo repeat protein have decreased alkaloid content, in particular decreased nicotine, nornicotine and PON content.

The invention claimed is:

1. A method of decreasing or increasing the nicotine, nornicotine, and/or pseudoxynicotine (PON) content of a *Nicotiana* plant or a part thereof, or a *Nicotiana* cell culture, in comparison to a control plant or control cell culture, wherein:

(A): the method of decreasing the nicotine, nornicotine, and/or PON content comprises modifying said plant or cell culture by reducing or preventing the expression of a gene encoding an ARMADILLO repeat protein in comparison to a control plant or control cell culture; and (B): the method of increasing the nicotine, nornicotine, and/or PON content comprises modifying said plant or cell culture by increasing the expression of a gene encoding an ARMADILLO repeat protein in comparison to a control plant or control cell culture, wherein the ARMADILLO repeat protein:

a) comprises an amino acid sequence as set out in: SEQ ID NO: 1 or a sequence which has at least 95% identity to SEQ ID NO: 1; or b) is encoded by a nucleotide sequence as set out in SEQ ID NO: 2 or 3_or a nucleotide sequence which has at least 95% identity to SEQ ID NO: 2 or 3.

2. The method according to claim 1, wherein reducing or preventing the expression of the gene encoding the ARMADILLO repeat protein comprises modifying the nucleotide sequence of the gene encoding the ARMADILLO repeat protein in an ARMADILLO repeat domain.

3. The method according to claim 1, wherein the nicotine, nornicotine, and/or PON content is decreased in comparison to a control plant or control cell culture.

4. A *Nicotiana* plant or part thereof or plant propagation material obtained therefrom or a *Nicotiana* cell culture which has been modified to achieve a decrease or increase in nicotine, nornicotine, and/or pseudoxynicotine (PON) content in comparison to a control plant or control cell culture, wherein:
   (A) the modification to decrease the nicotine, nornicotine, and/or PON content reduces or prevents the expression a gene encoding an ARMADILLO repeat protein in comparison to a control plant or control cell culture; and
   (B) the modification to increase the nicotine, nornicotine, and/or PON content increases the expression a gene encoding an ARMADILLO repeat protein in comparison to a control plant or control cell culture, wherein the ARMADILLO repeat protein:
      a) comprises an amino acid sequence as set out in SEQ ID NO: 1 or a sequence which has at least 95% identity to SEQ ID NO: 1; or
      b) is encoded by a nucleotide sequence as set out in SEQ ID NO: 2 or 3 or a nucleotide sequence which has at least 95% identity to SEQ ID NO: 2 or 3, wherein the plant propagation material is heterozygous or homozygous for the modification.

5. The *Nicotiana* plant or part thereof or plant propagation material obtained therefrom or *Nicotiana* cell culture according to claim 4, wherein the nicotine, nornicotine or PON content of the plant or cell culture is decreased in comparison to a control plant or control cell culture.

6. The *Nicotiana* plant or part thereof or plant propagation material obtained therefrom or *Nicotiana* cell culture according to claim 4, wherein the nicotine, nornicotine and PON content of the plant or cell culture is decreased in comparison to a control plant or control cell culture.

7. The *Nicotiana* plant or part thereof or plant propagation material obtained therefrom or *Nicotiana* cell culture according to claim 4, wherein the plant is a tobacco plant and nicotine content is decreased or increased in comparison to a control plant or control cell culture.

8. The tobacco plant or part thereof or plant propagation material obtained therefrom or tobacco cell culture according to claim 4, wherein the nicotine content is decreased in comparison to a control plant or control cell culture.

9. A harvested leaf or a cut harvested leaf of the plant according to claim 4 or obtained from a plant propagated from a propagation material according to claim 4, wherein the plant propagated from the propagation material is heterozygous or homozygous for the modification.

10. A processed leaf or a cut processed leaf obtained by processing the plant according to claim 4 or a plant propagated from a propagation material according to claim 4, wherein the plant propagated from the propagation material is heterozygous or homozygous for the modification.

11. The processed leaf according to claim 10, wherein the leaf is processed by curing, fermenting, pasteurizing or a combination thereof.

12. A cured tobacco material made from the plant or a part thereof according to claim 7 or a tobacco blend comprising a cured tobacco material made from the plant or a part thereof according to claim 7.

13. A *Nicotiana* plant carrying a heritable mutation in a nucleotide sequence which:
   a) encodes an amino acid sequence as set out in SEQ ID NO: 1 or a sequence which has at least 95% identity to SEQ ID NO: 1; or
   b) comprises a nucleotide sequence as set out in SEQ ID NO: 2 or 3 or a nucleotide sequence which has at least 95% identity to SEQ ID NO: 2 or 3,
   wherein said heritable mutation-reduces or prevents the expression of the nucleotide sequence encoding the ARMADILLO repeat protein and wherein the mutant plant has decreased nicotine, nornicotine and/or pseudoxynicotine (PON) content relative to a comparable plant which does not carry said heritable mutation.

14. Progeny or seed of a plant according to claim 13, wherein the progeny or seed carries the heritable mutation.

15. A harvested leaf, a processed leaf or cured tobacco material produced from the plant according to claim 13, wherein the harvested leaf, processed leaf or cured tobacco material carries the heritable mutation.

16. The processed leaf according to claim 10, wherein the leaf is a processed tobacco leaf.

17. The processed leaf according to claim 10, wherein the leaf is a non-viable processed tobacco leaf.

* * * * *

UNITED STATES PATENT AND TRADEMARK OFFICE
CERTIFICATE OF CORRECTION

PATENT NO. : 12,037,593 B2
APPLICATION NO. : 17/309285
DATED : July 16, 2024
INVENTOR(S) : Sara Ben Khaled and Francisco Anastacio De Abreu E Lima Page 1 of 1

It is certified that error appears in the above-identified patent and that said Letters Patent is hereby corrected as shown below:

In the Claims

Column 68, Claim 8, Line 1:
DELETE "claim 4," after "to"
INSERT --claim 7,-- after "to"

Signed and Sealed this
First Day of October, 2024

Katherine Kelly Vidal
*Director of the United States Patent and Trademark Office*